(12) United States Patent
Gillies et al.

(10) Patent No.: US 7,459,538 B2
(45) Date of Patent: Dec. 2, 2008

(54) RECOMBINANT TUMOR SPECIFIC ANTIBODY AND USE THEREOF

(75) Inventors: Stephen D. Gillies, Carlisle, MA (US); Kin-Ming Lo, Lexington, MA (US); Susan Xiuqi Qian, Concord, MA (US)

(73) Assignee: Merck Patent GmbH, Darmstadt (DE)

( * ) Notice: Subject to any disclaimer, the term of this patent is extended or adjusted under 35 U.S.C. 154(b) by 388 days.

(21) Appl. No.: 11/174,186

(22) Filed: Jul. 1, 2005

(65) Prior Publication Data

US 2005/0244418 A1   Nov. 3, 2005

Related U.S. Application Data

(62) Division of application No. 10/138,727, filed on May 3, 2002, now Pat. No. 6,969,517.

(60) Provisional application No. 60/288,564, filed on May 3, 2001.

(51) Int. Cl.
*C07K 16/00* (2006.01)

(52) U.S. Cl. .................. 530/387.3; 530/350; 530/387.7; 530/391.7

(58) Field of Classification Search .............. 530/387.3, 530/387.7, 391.7, 350
See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,522,811 A | 6/1985 | Eppstein et al. |
| 4,667,016 A | 5/1987 | Lai et al. |
| 4,676,980 A | 6/1987 | Segal et al. |
| 4,703,008 A | 10/1987 | Lin |
| 4,732,683 A | 3/1988 | Georgiades et al. |
| 4,737,462 A | 4/1988 | Mark et al. |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,589,466 A | 12/1996 | Felgner et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,641 A | 6/1997 | Pedersen et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |
| 5,733,876 A | 3/1998 | O'Reilly et al. |
| 5,738,852 A | 4/1998 | Robinson et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,795,779 A | 8/1998 | McCormick |
| 5,800,810 A | 9/1998 | Doyle et al. |
| 5,807,715 A | 9/1998 | Morrison et al. |
| 5,827,516 A | 10/1998 | Urban et al. |
| 5,827,703 A | 10/1998 | Debs et al. |
| 5,837,682 A | 11/1998 | Folkman et al. |
| 5,837,821 A | 11/1998 | Wu et al. |

(Continued)

FOREIGN PATENT DOCUMENTS

AU    21725/88    3/1989

(Continued)

OTHER PUBLICATIONS

U.S. Appl. No. 07/348,237, filed May 5, 1989, Rosenblum et al.

(Continued)

*Primary Examiner*—Stephen L Rawlings
(74) *Attorney, Agent, or Firm*—Goodwin Procter LLP

(57) ABSTRACT

The invention provides a family of antibodies that specifically bind the human epithelial cell adhesion molecule. The antibodies comprise modified variable regions, more specially, modified framework regions, which reduce their immunogenicity when administered to a human. The antibodies, when coupled to the appropriate moiety, may be used in the diagnosis, prognosis and treatment of cancer.

16 Claims, 3 Drawing Sheets

U.S. PATENT DOCUMENTS

| | | |
|---|---|---|
| 5,843,423 A | 12/1998 | Lyman et al. |
| 5,854,205 A | 12/1998 | O'Reilly et al. |
| 5,856,298 A | 1/1999 | Strickland |
| 5,858,347 A | 1/1999 | Bauer et al. |
| 5,885,795 A | 3/1999 | O'Reilly et al. |
| 5,886,178 A | 3/1999 | Allen et al. |
| 5,888,772 A | 3/1999 | Okasinski et al. |
| 5,888,773 A | 3/1999 | Jost et al. |
| 5,891,680 A | 4/1999 | Lieschke et al. |
| 5,908,626 A | 6/1999 | Chang et al. |
| 5,922,685 A | 7/1999 | Rakhmilevich et al. |
| 5,955,422 A | 9/1999 | Lin |
| 5,994,104 A | 11/1999 | Anderson et al. |
| 5,994,126 A | 11/1999 | Steinman et al. |
| 6,080,409 A | 6/2000 | Laus et al. |
| 6,086,875 A | 7/2000 | Blumberg et al. |
| 6,100,387 A | 8/2000 | Herrmann et al. |
| 6,169,070 B1 | 1/2001 | Chen et al. |
| 6,171,588 B1 | 1/2001 | Carron et al. |
| 6,231,536 B1 | 5/2001 | Lentz |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,335,176 B1 | 1/2002 | Inglese et al. |
| 6,340,742 B1 | 1/2002 | Burg et al. |
| 6,348,192 B1 | 2/2002 | Chan et al. |
| 6,406,689 B1 | 6/2002 | Falkenberg et al. |
| 6,429,199 B1 | 8/2002 | Krieg et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,506,405 B1 | 1/2003 | Desai et al. |
| 6,551,592 B2 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |
| 6,627,615 B1 | 9/2003 | Debs et al. |
| 6,646,113 B1 | 11/2003 | Dreyfuss et al. |
| 6,969,517 B2 | 11/2005 | Gillies et al. |
| 7,189,830 B2 | 3/2007 | Gillies et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies et al. |
| 2004/0180386 A1 | 9/2004 | Carr et al. |

FOREIGN PATENT DOCUMENTS

| | | |
|---|---|---|
| CN | 93100115.3 | 7/1993 |
| DE | 37 12985 | 11/1988 |
| DE | 37 12985 A1 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0338767 | 10/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 344 134 B1 | 1/1994 |
| EP | 0 601 043 B1 | 6/1994 |
| EP | 0 640 619 A1 | 3/1995 |
| EP | 0 668 353 A1 | 8/1995 |
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| EP | 0 699 755 B1 | 4/2004 |
| GB | 2 188 638 A | 10/1987 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 96/40792 | 12/1996 |
| WO | WO 97/00317 | 1/1997 |

| | | |
|---|---|---|
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO/98/46645 | 10/1998 |
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 A1 | 12/2000 |
| WO | WO 01/07081 A1 | 2/2001 |
| WO | WO 01/10912 A1 | 2/2001 |
| WO | WO 01/36489 A2 | 5/2001 |
| WO | WO 01/58957 A2 | 8/2001 |
| WO | WO 02/02143 A2 | 1/2002 |
| WO | WO/02/066514 | 8/2002 |
| WO | WO 02/066514 A2 | 8/2002 |
| WO | WO 02/072605 A2 | 9/2002 |
| WO | WO 02/074783 | 9/2002 |
| WO | WO 02/079232 A2 | 10/2002 |
| WO | WO 02/079415 A2 | 10/2002 |
| WO | WO 02/090566 A2 | 11/2002 |
| WO | WO 03/015697 A2 | 2/2003 |
| WO | WO 03/048334 A2 | 6/2003 |
| WO | WO 03/077834 A2 | 9/2003 |

OTHER PUBLICATIONS

Abaza et al., (1992), "Effects of Amino Acid Substitutions Outside an Antigenic Site on Protein Binding to Monoclonal Antibodies of Predetermined Specificity Obtained by Peptide Immunization," *Journal of Protein Chemistry*, 11:5:433-444.

Abstract XP-002116766, (1996), "Prostaglandins, their inhibitors and cancer," *Prostaglandins, Leukotrienes and Essential Fatty Acids*, 54:2:83-94.

Afonso et al., (1994), "The Adjuvant Effect of Interleukin-12 in a Vaccine Against Leishmania Major," *Science*, 263:235-237.

Arenberg et al. (1996), "Interferon-γ-inducible Protein 10 (IP-10) Is an Angiostatic Factor That Inhibits Human Non-small Cell Lung Cancer (NSCLC) Tumorigenesis and Spontaneous Metastases," *J. Exp. Med*, 184:981-992.

Bacha et al., (1998), "Interleukin 2 Receptor-Targeted Cytotoxicity Interleukin 2 Receptor-mediated Action of a Diphtheria Toxin-related Interleukin 2 Fusion Protein," *J. Experimental Medicine*, 167:612-622.

Bachelot et al., (Mar. 1998), "Retrovirus-Mediated Gene Transfer of an Angiostatin-Endostatin Fusion protein with Enhanced Anti-Tumor Properties In Vivo," *Proceedings of the Annual Meeting of the American Association for Cancer Research*, 39:271, Abstract #1856.

Barnett et al., (1994), "Purification, characterization and selective inhibition of human prostaglandin G/H synthase 1 and 2 expressed in the baculovirus system," *Biochimica et Biophysica Acta*, 1209:130-139.

Baselga, et al., (1998), "Recombinant Humanized Anti-HER2 Antibody (Herceptin™) Enhances the Antitumor activity of Paclitazel and Doxorubicin against HER3/neu Overexpressing Human Breast Cancer Xenografts," *Cancer Research*, 58:2825-2831.

Batova et al., (1999), "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Batra et al., (1993), "Insertion of Constant Region Domains of Human IgG1 into CD4-PE40 Increases Its Plasma Half-Life," *Mol. Immunol.*, 30:379-386.

Becker et al., (1996), "An Antibody-Interleukin 2 Fusion Protein Overcomes Tumor Heterogeneity by Induction of a Cellular Immune Response," *Proc. Natl. Acad. Sci.*, 93:7826-7831.

Becker et al., (1996), "Eradication of human hepatic and pulmonary melanoma metastases in SCID mice by antibody-interleukin 2 fusion proteins," *Proc. Natl. Acad. Sci. USA*, 93:2702-2707.

Beutler et al., (1988), "Tumor Necrosis, Cachexia, Shock, and Inflammation: A Common Mediator," *Ann. Rev. Biochem.*, 57:505-518.

Bissery et al., (1997), "The Taxoids," in *Cancer Therapeutics: Experimental and Clinical Agents*, Teicher, ed., 175-193.

Bjorn et al., (1985), "Evaluation of Monoclonal Antibodies for the Development of Breast Cancer Immunotoxins," *Cancer Research*, 45:1214-1221.

Boehm et al., (1997), "Antiangiogenic therapy of experimental cancer does not induce acquired drug resistance," *Nature*, 390:404-407.

Boehm et al., (1998), "Zinc-Binding of Endostatin Is Essential for Its Antiangiogenic Activity,"0 *Biochemical and Biophysical Research Communications*, 252:190-194.

Brooks et al., (1994), "Integrin $\alpha_v\beta_3$ Antagonists Promote Tumor Regression by Inducing Apoptosis of Angiogenic Blood Vessels," *Cell*, 79:1157-1164.

Buchli et al., (1993), "Structural and Biologic Properties of a Human Aspartic Acid-126 Interleukin-2 Analog," *Archives of Biochemistry and Biophysics*, 307:2:411-415.

Burgess et al., (1990), "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1483-1491.

Cao et al., (1996), "Kringle Domains of Human Angiostatin," *The Journal of Biological Chemistry*, 271:46:29461-29467.

Cao et al., (1997), "Kringle 5 of Plasminogen is a Novel Inhibitor of Endothelial Cell Growth," *The Journal of Biological Chemistry*, 272:36:22924-22928.

Capon et al., (1989), "Designing CD4 immunoadhesins for AIDS therapy," *Nature*, 337:525-531.

Caton et al., (1986), "Structural and functional implications of a restricted antibody response to a defined antigenic region on the influenza virus hemagglutinin," *The EMBO Journal*, 5:7:1577-1587.

Chan et al., (1991), "Induction of Interferon γ Production by Natural Killer Cell Stimulatory Factor: Characterization of the Responder Cells and Synergy with Other Inducers," *J. Exp Med.*, pp. 869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization," *Journal of Biological Chemistry*, 271:23:13349-13355.

Chaudhary et al., (1988), "Selective killing of HIV-infected cells by recombinant human CD4-Pseudomonas exotoxin hybrid protein," *Nature*, 335:370-372.

Chaudhary et al., (1989), "A recombinant immunotoxin consisting of two antibody variable domains fused to Pseudomonas exotoxin," *Nature*, 339:394-397.

Chen et al., (1997), "Eradication of Murine Bladder Carcinoma by Intratumor Injection of a Bicistronic Adenoviral Vector Carrying cDNAs for the IL-12 Heterodimer and Its Inhibition bu the IL-12 p40 Subunit Homodimer," *Journal of Immunology*, 159:1:351-358.

Cheon et al., (1994), "High-affinity binding sites for related fibroblast growth factor ligands reside within different receptor immunoglobulin-like domains," *Proc. Natl. Acad. Sci. USA*, 91: 989-993.

Chuang et al., (1993), "Effect of new investigational drug taxol on oncolytic activity and stimulation of human lymphocytes," *Gynecol. Oncol.*, 49:291-298.

Cohen, S. L. et al., (1996), "Human leptin characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 that Affect Binding to the 70-kDa Subunit (p70) of the Interleukin 2 Receptor," *Proc. Natl. Acad. Sci*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an inhibitor of angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Ding et al., (1988), "Zinc-Dependent Dimers Observed in Crystals of Human Endostatin," *Proceedings of the National Academy of Sciences of USA*, 95:10443-10448.

Earnest et al., (1992), "Piroxicam and Other Cyclooxygenase Inhibitors: Potential for Cancer Chemoprevention," *J. Cell. Biochem. Supp*, 161:156-166.

Eisenthal, (1990), "Indomethacin up-regulated the generation of lymphokine-activated killer-cell activity and antibody-dependent cellular cytotoxicity mediated by interleukin-2," *Cancer Immunol. Immunotherap.* 31:342-348.

Fell et al., (1991), "Genetic Construction and Characterization of Fusion Protein Consisting of a Chimeric F(ab') with Specificity for Carcinomas and Human IL-2," *The J. Immunology*, 146:7:2446-2452.

Fell et al., (1992), "Chimeric L6 antitumor antibody," *The J. Biol. Chem.*, 267:15552-15558.

Friedman, J. M. et al., (1998), "Leptin and the regulation of body weight in mammals," *Nature*, 395:763-770.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12 Receptor system: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen binding and biological activities of engineered mutant chimeric antibodies with human tumor specificities," *Hum. Antibod. Hybridomas*, 1:1:47-54.

Gillies et al., (1992), "Antibody-Targeted Interleukin 2 Stimulates T-Cell Killing of Autologous Tumor Cells," *Proc. Natl. Acad. Science*, 89:1428-1432.

Gillies et al., (1993), "Biological Activity and In Vivo Clearance of Antitumor Antibody/Cytokine Fusion Proteins," *Bioconjugate Chem.*, 4:230-235.

Gillies et al., (1998), "Antibody-IL-12 fusion proteins are effective in SCID mouse models of prostate and colon carcinoma matastases," *J. Immunology*, 160:2:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gilles et al., (1978), "T Cell Growth Factor: Parameters of Production And A Quantitative Microassay for Activity," *Journal of Immunology*, 120:6:2027-2032.

Goeddel et al., (1986), "Tumor Necrosis Factors: Gene Structure and Biological Activities," *Pharm. Sciences*, pp. 597-609.

Gren et al., (1983), "A New Type of Leukocytic Interferon," *Dokl. Biochem.*, 269:91-95.

Griffon-Etienne et al., (1999), "Taxane-induced apoptosis decompresses blood vessels and lowers interstitial fluid pressure in solid tumors: clinical implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73:8:2081-2805.

Guyre et al., (1997), "Increased potency of Fc-receptor-targeted antigens," *Cancer Immunol. Immunother.*, 45:146-148.

Harris et al., (1993), "Therapeutic Antibodies—the Coming of Age," *Tibtech*, 11:42-44.

Harvill et al., (1995), "An IgG3-IL2 Fusion Activates Complement, Binds FcYRI, Generates LAK Activity and Shows Enhanced Binding to the High Affinity IL-2R," *Immunotech.*, 1:95-105.

Harvill et al., (1996), "In vivo properties of an IgG3-IL-2 fusion protein: A general strategy for immune potentiation," *Journal of Immunology*, 157:7:3165-3170.

Hazama et al., (1993), "Adjuvant-Independent Enhanced Immune Responses to Recombinant Herpes Simplex Virus Type I Glycoprotein D by Fusion with Biologically Active Interleukin-2," *Vaccine*, 11:6:629-636.

He et al., (1998), "Humanization and Pharmacokinetics of Monoclonal Antibody with Specificity for Both E- and P-Selectin," *J. Immunol.*, 1029-1035.

Heijnen et al., (1996), "Antigen Targeting to Myeloid-specific Human FcYRI/CD64 Triggers Enhanced Antibody Responses in Transgenic Mice," *J. Clin. Invest.*, 97:2:331-338.

Heinzel et al., (1997), "In Vivo Production and Function of IL-12 p40 Homodimers," *J. Immunol.*, 158:4381-4388.

Hellstrom et al., (1986), "Antitumor effects of L6, an IgG2a antibody that reacts with most human carcinomas," *Proc. Natl. Acad. Sci.*, 83:18: 7059-7063.

Henkart, (1985), "Mechanism of Lymphocyte-Mediated Cytotoxicity," *Ann. Rev. Immuno.*, 3:31-58.

Herrmann et al., (1989), "Hematopoeitic Responses With Advanced Malignancy Treated With Recombinant Human Granulocyte-Macrophage Colony-Stimulating Factor," *Journal of Clinical Oncology*, 7:2:159-167.

Hohenester et al., (1998), "Crystal Structure of the Angiogenesis Inhibitor Endostatin at 1.5 Å Resolution," *EMBO Journal*, 17:6:1656-1664.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675.

Holden et al., (2001), "Augmentation of Antitumor activity of an Antibody-Interleukin 2 Immunocytokine with Chemotherapeutic Agents," *Clinical Cancer Research*, 7:2862-2869.

Hoogenboom et al., (1991), "Construction and expression of antibody-tumor necrosis factor fusion proteins," *Molecular Immunology*, 28:9:1027-1037.

Hoogenboom et al., (1991), "Targeting of Tumor Necrosis Factor to Tumor Cells Secretion by Myeloma Cells of a Gentically Engineered Antibody-Tumor Necrosis Factor Hybrid Molecule," *Biochem. and Biophys. Acta*, 1096:4:345-354 (Abstract).

Hornick et al, (1999), "Pretreatment with a monoclonal antibody/interleukin-2 fusion protein directed against DNA enhances the delivery of therapeutic molecules to solid tumors," *Clin. Cancer Res.*, 5:51-60.

Hu et al., (1996), "A Chimeric Lym-1/Interleukin 2 Fusion Protein for Increasing Tumor Vascular Permeability and Enhancing Antibody Uptake[1]," *Cancer Research*, 56:4998-5004.

Huck et al., (1986), "Sequence of a human immunoglobulin gamma 3 heavy chain constant region gene: comparison with the other human Cγ genes," *Nucleic Acids Research*, vol. 14:4:1779-1789.

Huse et al., (1989), "Generation of a Large Combinatorial Library of the Immunoglobulin Repertoire in Phage Lambda," *Science*, 246:1275-1281.

Ingber et al., (1990), "Synthetic analogues of fumagillin that inhibit angiogenesis and suppress tumour growth," *Nature*, 348:555-557.

Jones et al., (1986), "Replacing the complementarity-determining regions in a human antibody with those from a mouse," *Nature*, 321:6069:522-525.

Ju et al., (1987), "Structure-Function Analysis of Human Interleukin-2," *Journal of Biological Chemistry*, 262:12:5723-5731.

Jung et al., (1986), "Activation of human peripheral blood mononuclear cells by anti-T3: Killing of tumor target cells coated with anti-target-anti-T3 conjugates," *Proc. Natl. Acad. Sci.*, 83:4479-4483.

Junghans et al., (1996), "The protection receptor of IgG catabolism is the B2-micorgobulin-containing neonatal intestinal transport receptor," *Proc. Natl. Acad. Sci.*, 93:11:5512-5516.

Kang et al., (1991), "Antibody redesign by chain shuffling from random combinatorial immunoglobulin libraries," *Proc. Natl. Acad. Sci.*, 88:11120-11123.

Kappel et al., (1992), "Regulating gene expression in transgenic animals," *Current Opinion in Biotechnology* 3:548-553.

Karpovsky et al., (1984), "Production of Target-Specific Effector Cells using Hetero-Cross Linked Aggregate Containing Anti-Target Cell and AntiFcλ Receptor Antibodies," *Journal of Experimental Medicine*, 160:6:1686-1701.

Kendra et al., (1999), "Pharmacokinetics and Stability of the ch 14.18-Interleukin-2 Fusion Protein in Mice," *Cancer Immunol. Immunotherapy*, 48:219-229.

Kim et al., (1997), "An Ovalbumin-IL-12 fusion protein is more effective than ovalbumin plus free recombinant IL-12 in inducing a T helper cell type 1-dominated immune response and inhibiting antigen-specific IgE production," *Journal Immunology*, 158:9:4137-4144.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

Kranz et al., (1984), "Attachment of an anti-receptor antibody to non-target cells renders them susceptible to lysis by a clone of cytotoxic T lymphocytes," *Proc. Natl. Acad. Sci.*, 81:7922-7926.

Kuo et al., (2001), "Oligomerization-dependent Regulation of Motility and Morphogenesis by the Collagen XVIII NC1/Endostatin Domain," *Journal of Cell Biology*, 152:6:1233-1246.

LaVallie et al., (1993), "Cloning and Functional Expression of a cDNA Encoding the Catalytic Subunit of Bovine Enterokinase," *Journal of Biological Chemistry*, 268:31:23311-23317.

Lazar et al., (1988), "Transforming Growth Factor α: Mutation of Aspartic Acid 47 and Leucine 48 Results in Different Biological Activities," *Molecular and Cellular Biology*, 8:3:1247-1252.

LeBerthon et al., (1991), "Enhanced Tumor Uptake of Macromolecules Induced by a Novel Vasoactive Interleukin 2 Immunoconjugate," *Cancer Reseach*, 51:2694-2698.

Lieschke, et al., (1997), "Bioactive murine and human interleukin-12 fusion proteins which retain antitumor activity in vivo," *Nature Biotechnology*, 15:1:35-40.

Linsley et al., (1991), "CTLA-4 is a Second Receptor for B Cell Activation Antigen B7," *Journal of Experimental Medicine*, 174:3:561-569.

Liu et al., (1985), "Heteroantibody Duplexes Target Cells for Lysis by Cytotoxic T Lymphocytes," *Proc. Natl. Acad. Sci.*, 82:8648-8652.

Liu et al., (1988), "Hormone Conjugated with Antibody to CD3 Mediates Cytotoxic T Cell Lysis of Human Melanoma Cells," *Sciences*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92:10:3730-3736.

Lo et al., (1998), "High Level Expression and Secretion of Fc-X Fusion Proteins in Mammalian Cells," *Protein Engineering*, 11:6:495-500.

Lode et al., (1998), "Immunocytokines: a promising approach to cancer immunotherapy," *Pharmacol. Thera.*, 80:3:277-292.

Lode et al., (1998), "Natural Killer Cell-Mediated Eradication of Neuroblastoma Metastases to Bone Marrow by Targeted Interleukin-2 Therapy," *Blood*, 91:5:1706-1715.

Lode et al., (1999), "Synergy between an antiangiogenic integrin $α_v$ antagonist and an antibody-cytokine fusion protein eradicates spontaneous tumor metastases," *Proc. Natl. Acad. Sci.*, 96:1591-1596.

Lode et al., (1999), "Tumor-targeted IL-2 amplifies T cell-mediated immune response induced by gene therapy with single-chain IL-12," *Proc. Natl. Acad. Sci.*, 96:8591-8596.

Lode et al., (2000), "Amplification of T Cell Mediated Immune Responses by Antibody-Cytokine Fusion Proteins," *Immunological Investigations*, 29:2:117-120.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84:8:2457-2466.

Mark et al., (1992), "Expression and characterization of hepatocyte growth factor receptor-IgG fusion proteins," *Journal of Biological Chemistry*, 267:36:26166-26171.

Martinotti et al., (1995), "CD4 T Cells Inhibit in vivo the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1[1]," *J. Immunology*, 158:5:2211-2217.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 CELLS: Different Patterns of Lymphokine Secretion Lead to Different Functional Properties," *Ann. Rev. Immunol*, 7:145-173.

Mott et al., (1995), "The Solution Structure of the F42A Mutant of Human Interleukin 2," *J. Mol. Biol.*, 247:979-994.

Mullins et al., (1998), "Interleukin-12 overcomes paclitaxel-mediated suppression of T-cell proliferation," *Immunopharmacol. Immunotoxicol.*, 20:4:473-492.

Murphy et al., (1986), "Genetic construction, expression, and melanoma-selective cytotoxicity of a diphtheria toxin-related α-melanocyte-stimulating hormone fusion protein," *Proc. Natl. Acad. Sci.*, 83:8258-8262.

Murphy, (1988), "Diphtheria-related peptide hormone gene fusions: A molecular gene approach to chimeric toxin development," *Immunotoxins*, 123-140.

Nedwin et al., (1985), "Human Lymphotoxin and Tumor Necrosis Factor Genes: Structure, Homology and Chromosomal Localization," *Nucleic Acids Research*, 13:17:6361-6373.

Netti et al., (1995), "Time-dependent behavior of interstitial fluid pressure in solid tumors: implications for drug delivery," *Cancer Research*, 55:5451-5458.

Netti et al., (1999), "Enhancement of fluid filtration across tumor vessels: implication for delivery of macromolecules," *Proc. Nat. Acad. Sci*, 96:3137-3142.

Neuberger et al., (1984), "Recombinant Antibodies Possessing Novel Effector Functions," *Nature*, 312:604-608.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin induces and sustains dormancy of human primary tumors in mice," *Nature Medicine*, 2:6:689-692.

O'Reilly et al., (1997), "Endostatin: An Endogenous Inhibitor of Angiogenesis and Tumor Growth," *Cell*, 88:277-285.

Pastan et al., (1989), "Pseudomonas Exotoxin: Chimeric Toxins," *Journal of Biological Chemistry*, 264:26:15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target cell antibodies," *J. Exp. Medicine*, 163:166-178.

Perez et al., (1989), "Isolation and Characterization of a cDNA Encoding the KS1/4 Epithelial Carcinoma Marker," *Journal of Immunology*, 142:10:3662-3667.

Polizzi et al., (1999), "A novel taxane improved tolerability and therapeutic activity in a panel of human tumor xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Nat'l Acad. Sci.*, 94:20:10889-10894.

Reisfeld et al., (1996), "Recombinant antibody fusion proteins for cancer immunotherapy," *Current Topics in Microbiology and Immunology*, 27-53.

Reisfeld et al., (1997), "Immunocytokines: a new approach to immunotherapy of melanoma," *Melanoma Research*, 7:2:S99-S106.

Riethmuller et al., (1994), "Randomised trial of monoclonal antibody for adjuvant therapy of resected Dukes' C colorectal carcinoma," *The Lancet*, 343:1177-1183.

Roessler et al., (1994), "Cooperative interactions between the interleukin 2 receptor $\alpha$ and $\beta$ chains alter the interleukin 2-binding affinity of the receptor subunits," *Proc. Natl. Acad. Sci.*, 91:3344-3347.

Roitt et al., (1993), "The Role of TH Cells in the Selection of Effector Mechanisms Directed Against Target Antigens," *Immunology*, Third Edition, 8.3-8.4.

Rosenberg, (1988), "Immunotherapy of Cancer Using Interleukin 2: current status and future prospects," *Immunology Today*, 9:2:58-62.

Rozwarski et al., (1994), "Structural comparisons among the short-chain helical cytokines," *Structure*, 2:3:159-173.

Santon et al., (1986), "Effects of Epidermal Growth Factor Receptor Concentration on Tumorigenicity of A431 Cells in Nude Mice," *Cancer Research*, 46:4701-4705.

Sasaki et al., (1998), "Structure, function and tissue forms of the C-terminal globular domain of collagen XVII containing the angiogenesis inhibitor endostatin," *The EMBO Journal*, 17:15:4249-4256.

Sauve et al., (1991), "Localization in human interleukin 2 of the binding site of the $\alpha$ chain (p55) of the interleukin 2 receptor," *Proc. Natl. Acad. Sci.*, 88:4636-4640.

Schnee et al., (1987), "Construction and expression of a recombinant antibody-targeted plasminogen activator," *Proc. Natl. Acad. Sci.*, 84:6904-6908.

Schoenhaut et al., (1992), "Cloning and Expression of Murine IL-12," *Journal of Immunology*, 148:11:3433-3340.

Senter et al., (1988), "Anti-tumor effects of antibody-alkaline phosphatase conjugates in combination with etoposide phosphate," *Proc. Natl. Acad. Sci.*, 85:13:4842-4846.

Shanafelt et al., (2000), "A T-cell-selective interleukin 2 mutein exhibits potent antitumor activity and is well tolerated in vivo," *Nature Biotechnology*, 18:1197-1202.

Sharma et al., (1999), "T cell-derived IL-10 promotes lung cancer growth by suppressing both T cell and APC function," *Journal of Immunology*, 163:5020-5028.

Shen et al., (1986), "Heteroantibody-Mediated Cytotoxicity: Antibody to the high affinity Fc receptor for IgG mediates cytotoxicity by human monocytes that is enhanced by interferon-$\lambda$ and is not blocked by human IgG," *Journal of Immunology*, 137:11:3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and characterization of an antibody binding specificity joined to insulin-like growth factor 1: Potential applications for cellular targeting," *Proc. Natl. Acad. Sci.*, 87:5322-5326.

Sim et al., (1997), "A Recombinant Human Angiostatin Protein Inhibits Experimental Primary and Metastatic Cancer," *Cancer Research*, 57:1329-1334.

Stevenson et al., (1997), "Conjugation of Human Fc$\gamma$ in Closed-Hinge or Open-Hinge Configuration to Fab'$\gamma$ and Analogous Ligands," *Journal of Immunology*, 158:2242-2250.

Sulitzeanu et al., (1993), "Immunosuppressive factors in human cancer," *Adv. Cancer Research*, 60:247-267.

Taniguchi et al., (1983), "Structure and expression of a cloned cDNA for human interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *Journal of Immunology*, 143:8:2595-2601.

Tao et al., (1993), "Structural Features of Human Immunoglobulin G that Determine Isotype-Differences in Complement Activation," *Journal of Experimental Medicine*, 178:2:661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 990-993, 1278-1283 (17$^{th}$ ed. 1999).

Till et al., (1988), "An Assay that Predicts the Ability of Monoclonal Antibodies to Form Potent Ricin A Chain-containing Immunotoxins," *Cancer Research*, 48:5:1119-1123.

Till et al., (1988), "HIV-Infected Cells are Killed by rCD4-Ricin A Chain," *Science*, 242:1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," *Blood*, 84:4008-4027.

Vagliani et al., (1996), "Interleukin 12 Potentiates the Curative Effect of a Vaccine Based on Interleukin 2-transduced Tumor Cells," *Cancer Research*, 56:467-470.

Varki et al., (1984), "Antigens Associated with a human lung adenocarcinoma defined by monoclonal antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive expression of Fas (Apo-1/CD95) ligand on multiple myeloma cells: a potential mechanism of tumor-induced suppression of immune surveillance," *Blood*, 90:1:12-20.

Watanabe et al., (1997), "Long-term depletion of naive T cells in patients treated for Hodgkin's disease," *Blood*, 90:9:3662-3672.

Williams et al., (1986), "Production of antibody-tagged enzymes by myelanoma cells: application to DNA polymerase I Klenow fragment," *Gene*, 43:319-324.

Williams et al., (1987), "Diphtheria toxin receptor binding domain substitution with interleukin-2: genetic construction and properties of a diphtheria toxin-related interleukin-2 fusion protein," *Protein Engineering*, 1:6:493-498.

Wooley et al., (1993), "Influence of a Recombinant Human Soluble Tumor Necrosis Factor Receptor Fc Fusion Protein on Type II Collagen-Induced Arthritis in Mice," *Journal Immunology*, 151: 6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Zheng et al., (1995), "Administration of noncytolytic IL-10/Fc in muring models of lipopolysaccharide-induced septic shock and allogenic islet transplantation," *Journal of Immunology*, 154:5590-5600.

Xu et al., (1994), "Residue at Position 331 in the IgG1 and IgG4 CH2 Domains Contributes to Their Differential Ability to Bind and Activate Complement," *J. Biol. Chem.*, 269:3469-3474.

Angal et al. (1993), "A Single Amino Acid Substitution Abolishes the Heterogeneity of Chimeric Mouse/Human (IgG4) Antibody," *Molecular Immunology*, 30:105-108.

Becker et al., (1996), "Long-lived and transferable tumor immunity in mice after targeted interleukin-2 therapy," *J Clin Invest.*, 98(12):2801-4.

Becker et al., (1996), "T Cell-mediated eradication of murine metastatic melanoma induced by targeted interleukin 2 therapy," *J Exp Med.*, 183(50):2361-6.

Bitonti et al. (2002), "Transepithelial Absorption of an Erythropoietin-Fc Fusion Protein After Delivery to the Central Airways," *Respiratory Drug Delivery*, 8:309-312.

Boissel et al., (1993), "Erythropoietin Structure-Function Relationships: Mutant Protein that Test a Model of Tertiary Structure," *The Journal of Biological Chemistry*, 268(21):15983-15993.

Briggs et al., (1974), "Hepatic Clearance of Intact and desialylated Erythropoietin," *American Journal of Physiology*, 227:1385-1388.

Chuang et al. (1994), "Alteration of Lymphocyte Microtubule Assembly, Cytotoxicity, and Activation by the Anticancer Drug Taxol," *Cancer Research*, 54:1286-1291.

Cruse et al., (1995), Illustrated Dictionary of Immunology, CRC Press, NY, p. 156-7.

Darling et al. (2002), "Glycosylation of Erythropoietin Affects Receptor Binding Kinetics: Role of Electrostatic Interactions," *Biochemistry*, 41:14524-14531.

Davis et al. (2003), "Immunocytokines: amplification of anti-cancer immunity," *Cancer Immunol Immunother* 52:297-308.

Dolman et al., (1998), "Suppression of human prostate carcinoma metastases in severe combined immunodeficient mice by interleukin 2 immunocytokine therapy," *Clin Cancer Res.*, 4(10):2551-7.

Duncan et al., (1988), "The binding site for C1q and IgG," *Nature*, 332:738-740.

Egrie et al., (2001), "Development and characterization of novel erythropoiesis stimulating protein (NESP)," *Nephrol. Dial. Transplant.*, 16:3-13.

Elliott et al., (1997), "Mapping of the Active Site of Recombinant Human Erythropoietin," *Blood*, 89(2):493-502.

Fibi et al. (1995), "N- and O-Glycosylation Muteins of Recombinant Human Erythropoietin Secreted From BHK-21 Cells," *Blood*, 85:1229-1236.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific enzyme-linked immunosorbent assays for quantitation of antibody-cytokine fusion proteins," *Clin Diagn Lab Immunol.*, 6(2):236-42.

Gillies et al., (1991), "Expression of genetically engineered immunoconjugates of lymphotoxin and a chimeric anti-ganglioside GD2 antibody," *Hybridoma.*, 10(3):347-56.

Gillies et al., (2002), "Bi-functional cytokine fusion proteins for gene therapy and antibody-targeted treatment of cancer," *Cancer Immunol Immunother.*, 51(8):449-60.

Gillies et al., (2002), "Improved circulating half-life and efficacy of an antibody-interleukin 2 immunocytokine based on reduced intracellular proteolysis," *Clin. Cancer Res.*, 8(1):210-6.

Greene et al., (1975), "Neuronal Properties of Hybrid Neuroblastoma X Sympathetic Ganglion Cells," *Proc. Natl. Acad. Sci. USA*, 72(12):4923-4927.

Hammerling et al. (1996), "In vitro bioassay for human erythropoietin based on proliferative stimulation of an erythroid cell line and analysis of carbohydrate-dependent microheterogeneity," *Journal of Pharmaceutical and Biomedical Analysis*, 14:1455-1469.

Hank et al., (1996), "Activation of human effector cells by a tumor reactive recombinant anti-ganglioside GD2 interleukin-2 fusion protein (ch14.18-IL2)," *Clin Cancer Res.*, 2(12):1951-9.

Hank et al., (2003), "Determination of peak serum levels and immune response to the humanized anti-ganglioside antibody-interleukin-2 immunocytokine," *Methods Mol Med.*, 85:123-31.

Haraguchi, (1994), "Isolation of GD3 Synthase Gene by Expression Cloning of GM3 α-2,8-sialyltransferase cDNA Using Anti-GD2 Monoclonal Antibody," *Proc. Natl. Acad. Sci. USA*, 91(22):10455-10459.

Harris, (1995), "Processing of C-terminal lysine and arginine residues of proteins isolated from mammalian cell culture," *J. Chromatogr. A*, 705:129-134.

Hezareh et al, (2001), "Effector function activities of a panel of mutants of a broadly neutralizing antibody against human immunodeficiency virus type 1," *J. Virol.*, 75(24):12161-8.

Idusogie et al., (2000), "Mapping of the C1q binding site on rituxan, a chimeric antibody with a human IgG1 Fc" *J. Immunol.*, 164(8):4178-84.

Imboden et al., (2001), "The level of MHC class I expression on murine adenocarcinoma can change the antitumor effector mechanism of immunocytokinetherapy," *Cancer Res.*, 61(4):1500-7.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26:126-131.

Kitamura et al. (1989), "Establishment and Characterization of a Unique Human Cell Line that Proliferates Dependently on GM-CSF, IL-3, or Erythropoietin," *Journal of Cellular Physiology*, 140:323-334.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Locatelli et al. (2001), "Darbepoetin alfa Amgen," *Current Opinion in Investigational Drugs*, 2:1097-1104.

Lode et al., (1997), "Targeted interleukin-2 therapy for spontaneous neuroblastoma metastases to bone marrow," *J Natl Cancer Inst.*, 89(21):1586-94.

Lode et al., (2000), "What to do with targeted IL-2," *Drugs Today*, 36(5):321-36.

Lode et al., (2000), "Melanoma immunotherapy by targeted Il-2 depends on CD4(+) T-cell help mediated by CD40-CD40L interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17:66-70.

Metelitsa et al., (2002), "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis," *Blood*, 99(11):4166-73.

Mueller et al. (1997), "Humanized porcine VCAM-specific monoclonal antibodies with chimeric IgG2/G4 constant regions block human leukocyte binding to porcine endothelial cells," *Molecular Immunology*, 34(6):441-452.

Mullins et al. (1997), "Taxol-mediated changes in fibrosarcoma-induced immune ell function: modulation of antitumor activities," *Cancer Immunol Immunother*, 45:20-28.

Naramura et al., "Mechanisms of cellular cytotoxicity mediated by a recombinant antibody-IL2 fusion protein against human melanoma cells," *Immunol Lett.*, 39(1):91-9.

Neal et al. (2003), "NXS2 murine neuroblastomas express increased levels of MHC class I antigens upon recurrence following NK-dependent immunotherapy," *Cancer Immunol Immunother.*, Pub. Med ID: 14504825.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2001) "An oral DNA vaccine against human carinoembryonic antigen (CEA) prevent growth and dissemination of Lewis Lung carcinoma in CEA transgenic mice," *Vaccine*, 20(3-4):421-9.

Niethammer et al., (2001) "Targeted Interleukin 2 therapy enhances protective immunity induced by an autologous murine melanoma," *Cancer Res.*, 61(16):6178-84.

Nimtz et al., (1993) Structures of Sialylated Oligosaccharides of Human Erythropoietin Expressed in recombinant BHK-21 Cells, *Eur. J. Biochem.*, 213:39-56.

Pancook et al., (1996), "Eradication of established hepatic human neuroblastoma metastases in mice with severe combined immunodeficiency by antibody-targeted interleukin-2," *Cancer Immunol Immunother.*, 42(2):88-92.

Park et al., (2000), "Efficiency of promoter and cell line in high-level expression of erythropoietin," *Biotechnol. Appl. Biochem.*, 32:167-172.

Reisfeld et al., (1996), "Antibody-interleukin 2 fusion proteins: a new approach to cancer therapy," *J Clin Lab Anal.*, 10(3):160-6.

Reisfeld et al., (1996), "Involvement of B lymphocytes in the growth inhibition of human pulmonary melanoma metastases in athymic nu/nu mice by an antibody-lymphotoxin fusion protein," *Cancer Res.*, 56(8):1707-12.

Ruehlmann et al., (2001), "MIG (CIXCL9) chemokine gene therapy combines with antibody-cytokine fusion protein to suppress growth and dissemination of murine colon carcinoma," *Cancer Res.*, 61(23):8498-503.

Sabzevari et al., (1994), "A recombinant antibody-interleukin 2 fusion protein suppresses growth of hepatic human severe combined immunodeficiency mice," *Proc Natl Acad Sci USA*, 91(20):9626-30.

Seidenfeld et al., (2001), "Epoietin Treatment of Anemia Associated with Cancer Therapy: A Systematic Review and Meta-analysis of controlled Clinical Trials," *Journal of National Cancer Institute*, 93:1204-1214.

Shinkawa et al., (2003), "The Absence of Fucose But Not the Presence of Galactose or Bisecting N- Acetylglucosamine of Human IgG1 Complex-Type Oligosaccharides Shows the Critical Role of Enhancing Antibody-Dependent Cellular Cytotoxicity," *J. Biol. Chem.*, 278:3466-3473.

Spiekermann et al. (2002), "Receptor-mediated Immunoglobulin G Transport Across Mucosal Barriers in Adult Life: Functional Expression of FcRn in the Mammalian Lung," *J. Exp. Med.*, 196:303-310.

Strom et al., (1996), "Therapeutic Approach to Organ Transplantation," Chapter 36, pp. 451-456, in *Therapeutic Immunology*, Austen et al., (eds.), Blackwell Science.

Syed et al. (1998), "Efficiency of signaling through cytokine receptors depends critically on receptor orientation," *Nature*, 395:511-516.

Thommesen et al., (2000), "Lysine 322 in the Human IgG3 CH2 Domain is Crucial for Antibody Dependent Complement Activation," *Mol. Immunol.*, 37(16):995-1004.

Wells, (1990), "Additivity of Mutational Effect in Proteins," *Biochemistry*, 29(37):8509-8517.

Wen et al., (1993), "Erythropoietin Structure-Function Relationships: High Degree of Sequence Homology Among Mammals," *Blood*, 82:1507-1516.

Xiang et al., (1998), "Induction of persistent tumor-protective immunity in mice cured of established colon carcinoma metastases," *Cancer Res.*, 58(17)3918-25.

Xiang et al., (1999) "T Cell memory against colon carcinoma is long-lived in the absence of antigen," *J Immunol.*, 163(7):3676-83.

Xiang et al., (2001), "A dual function DNA vaccine encoding carcinoembryonic antigen and CD40 ligand trimer induces T cell-mediated protective immunity against colon cancer in carcinoembryonic antigen-transgenic mice," *J Immunol.*, 167(8):4560-5.

Xiang et al., (2001), "Protective immunity against human carcinoembryonic antigen (CEA) induced by an oral DNA vaccine in CEA-transgenic mice," *Clin Cancer Res.*, 7(3 Suppl):856s-864s.

Yu et al., (1998), "Phase I Trial of a Human-Mouse Chimeric Anti-Disialoganglioside Monoclonal Antibody ch14.18 in Patients with Refractory Neuroblastoma and Osteosarcoma," *J. Clinical Oncology*, 16(6):2169-80.

Zagozdzon et al. (1999), "Potentiation of antitumor effect of IL-12 in combination with paclitaxel in murine melanoma model in vivo," *International Journal of Molecular Medicine*, 4:645-648.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Cruse et al., (eds.), (1995), *Illustrated Dictionary of Immunology*, p. 158, CRC Press, NY.

de la Salle et al., (1996), "FcγR on Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et al., (1995), "A Phase I Study of Human/Mouse Chimeric Anti-ganglioside GD2 Antibody ch14.18 in Patients with Neuroblastoma," *European J. Cancer*, 31A(2):261-267.

Hurn et al., (1980), "Production of Reagent Antibodies," *Methods in Enzymology*, 70: 104-142.

*Investigator's Brochure*, (2004), pp. 6-8, 28, 29, 41, and 43.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Ko et al., (2004), "Safety Pharmacokinetics, and Biological Pharmacodynamics of the Immunocytokine EMD 273066 (huKS-IL2)," *J. Immunotherapy*, 27: 232-239.

Lo et al., (1992), "Expression and Secretion of an Assembled Tetrameric CH2-deleted Antibody in *E. coli.*," *Hum. Antibod. Hybridomas*, 3:123-128.

Maecker et al., (1997), "DNA Vaccination with Cytokine Fusion Constructs Biases the Immune Response to Ovalbumin," *Vaccine*, 15(15):1687-1696.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Reisfeld et al., (1994), "Potential of Genetically Engineered Anti-Ganglioside GD2 Antibodies for Cancer Immunotherapy," *Prog. Brain Res.*, 101:201-212.

Saleh et al., (1992), "Phase I Trial of the Chimeric Anti-GD2 Monoclonal Antibody ch14.18 in Patients With Malignant Melanoma," *Hum. Antibod. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Schlom (1991), "Monoclonal Antibodies: They're More and Less Than You Think," in *Molecular Foundations of Oncology*, pp. 95-133.

Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wen et al., (1994), "Erythropoietin Structure-Function Relationships: Identification of Functionally Important Domains," *J. Biological Chemistry*, 269(36):22839-22846.

Aichele et al., (1994), "Peptide-Induced T-Cell Tolerance to Prevent Autoimmune Diabetes in a Transgenic Mouse Model," *Proc. Natl. Acad. Sci. USA*, 91:444-448.

Altschul et al., (1990), "Basic Local Alignment Search Tool," *J. Mol. Biol.*, 215:403-10.

Altschul et al., (1997), "Gapped BLAST and PSI-BLAST: A New Generation of Protein Database Search Programs," *Nucleic Acids Res.*, 25(17):3389-3402.

Anderson et al., (1980), "Characterization of the Fc Receptor for IgG on a Human Macrophage Cell Line U937," *J. Immunol.*, 125(6):2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et al., (1998), "IL-12 and IL-18 Differentially Regulate the Transcriptional Activity of the Human IFN-γ Promoter in Primary CD4+ T Lymphocytes," *J. Immunol.*, 160:3642-7.

Bednarek et al., (1991), "Soluble HLA-A2.1 Restricted Peptides that are Recognized by Influenza Virus Specific Cytotoxic T Lymphocytes," *J. Immunol. Methods*, 139:41-47.

Benacerraf et al., (1959), "The Clearance of Antigen Antibody Complexes from the Blood by the Reticulo-Endothelial System," *J. Immunol.*, 82:131-7.

Böhm, (1994), "On the Use of LUDI to Search the Fine Chemicals Directory for Ligands of Proteins of Known Three-Dimensional Structure," *J. Comput. Aided Mol. Des.*, 8:623-32.

Böhm, (1994), "The Development of a Simple Empirical Scoring Function to Estimate the Binding Constant for a Protein-Ligand Complex of Known Three-Dimensional Structure," *J. Comput. Aided Mol. Des.*, 8(3):243-56.

Böhm, (1998), "Prediction of Binding Constants of Protein Ligands: A Fast Method for the Prioritization of Hits Obtained from De Novo Design or 3D Database Search Programs," *J. Comput. Aided Mol. Des.*, 12(4):309-23.

Boshart et al., (1985), "A Very Strong Enhancer is Located Upstream of an Immediate Early Gene of Human Cytomegalovirus," *Cell*, 41:521-530.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-35.

Brambell et al., (1964), "A Theoretical Model of γ-Globulin Catabolism," *Nature*, 203:1352-55.

Brazolot Millan et al., (1998), "Cpg DNA Can Induce Strong TH1 Humoral and Cell-Mediated Immune Responses against Hepatitis B Surface Antigen in Young Mice," *Proc. Natl. Acad. Sci. USA*, 95:15553-8.

Brekke et al., (1994), "Human IgG Isotype-Specific Amino Acid Residues Affecting Complement-Mediated Cell Lysis and Phagocytosis," *Eur. J. Immunol.*, 24:2542-2547.

Brem et al., (1993), "The Combination of Antiangiogenic Agents to Inhibit Primary Tumor Growth and Metastasis," *J. Pediatr. Surg.*, 28(10):1253-7.

Brocklebank et al., (2001), "Enumeration of CD34+ Cells in Cord Blood: A Variation on a Single-Platform Flow Cytometric Method Based on the ISHAGE Gating Strategy," *Cytometry*,46(4):254-61.

Brooks et al., (1983), "CHARMM: A Program for Macromolecular Energy Minimization and Dynamics Calculations," *J. Comput. Chemistry*, 4:187-217.

Broudy et al., (1988), "Recombinant Human Erythropoietin: Purification and Analysis of Carbohydrate Linkage," *Arch. Biochem. Biophys.*, 265:329-36.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Bumol et al., (1982), "Unique Glycoprotein-Proteoglycan Complex Defined by Monoclonal Antibody on Human Melanoma Cells," *Proc. Natl. Acad. Sci. USA*, 79:1245-9.

Carnemolla et al., (1989), "A Tumor-Associated Fibronectin Isoform Generated by Alternative Splicing of Messenger RNA Precursors," *J. Cell. Biol.*, 108:1139-1148.

Carnemolla et al., (1992), "The Inclusion of the Type III Repeat ED-B in the Fibronectin Molecule Generates Conformational Modifications that Unmask a Cryptic Sequence," *J. Biol. Chem.*, 267(34):24689-24692.

Casadevall et al., (2002), "Pure Red-Cell Aplasia and Antierythropoietin Antibodies in Patients Treated with Recombinant Erythropoietin," *N. Engl. J. Med.*, 346(7):469-75.

Cazzola et al., (1998), "Red Blood Cell Precursor Mass as an Independent Determinant of Serum Erythropoietin Level," *Blood*, 91:2139-45.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cheetham, (1998), "NMR Structure of Human Erythropoietin and a Comparison with its Receptor Bound Conformation," *Nat. Struct. Biol.*, 5:861-6.

Ciardiello et al., (1996), "Antitumor Activity of Combined Blockade of Epidermal Growth Factor Receptor and Protein Kinase A," *J. Natl. Cancer Inst.*, 88:1770-6.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Congote et al., (1984), The Erthrotropins, New Erythroid Cell Stimulate Factors Extracted From Human and Bovine Fetal Tissues, Abstract 364, "Proceedings 7th Intl. Congress of Endocrinology," Quebec City, Quebec, Jul. 1-7, 1984.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et al., (1989), "High-Resolution Epitope Mapping of hGH-Receptor Interactions by Alanine-Scanning Mutagenesis," *Science*, 244:1081-85.

Curiel et al., (1991), "Adenovirus Enhancement of Transferrin-Polylysine-Mediated Gene Delivery," *Proc. Natl. Acad. Sci. USA*, 88:8850-4.

Dauber-Osguthorpe et al., (1988), "Structure and Energetics of Ligand Binding to Proteins: *Escherichia coli* Dihydrofolate Reductase-Trimethoprim, A Drug-Receptor System," *Proteins*, 4:31-47.

Daugherty et al., (1991), "Polymerase Chain Reaction Facilities the Cloning, CDR-Grafting, and Rapid Expression of a Murine Monoclonal Antibody Directed Against the CD18 Component of Leukocyte Integrins," *Nucleic Acid Res.*, 19:2471-2476.

De Bruijn et al., (1995), "Phagocyte-Induced Antigen-Specific Activation of Unprimed CD8+ T Cells in Vitro," *Eur. J. Immunol.*, 25:1274-85.

Delorme et al., (1992), "Role of Glycosylation on the Secretion and Biological Activity of Erythropoietin," *Biochemistry*, 31:9871-6.

Desai et al., (1992), "IL-12 Receptor. II. Distribution and Regulation of Receptor Expression," *J. Immunol.*, 148:3125-32.

Donnelly et al., (1993), "Targeted Delivery of Peptide Epitopes to Class I Major Histocompatibility Molecules by a Modified Pseudomonas Exotoxin," *Proc. Natl. Acad. Sci. USA*, 90:3530-4.

Donnelly et al., (1997), "DNA Vaccines," *Annu. Rev. Immunol.*, 15:617-48.

Dube et al., (1988), "Glycosylation at Specific Sites of Erythropoietin is Essential for Biosynthesis, Secretion, and Biological Function," *J. Biol. Chem.*, 263:17516-21.

Ellison et al., (1982), "The Nucleotide Sequence of a Human Immunoglobulin C $\gamma_1$ Gene," *Nucleic Acids Res.*, 10:4071-9.

Faas et al., (1993), "Phenotypically Diverse Mouse Thymic Stromal Cell Lines which Induce Proliferation and Differentiation Of Hematopoietic Cells," *Eur. J. Immunol.*, 23:1201-14.

Farner et al., (1995), "Distinction Between $\gamma_c$ C Detection and Function in YT Lymphoid Cells and in the Granulocyte-Macrophage Colony-Stimulating Factor-Responsive Human Myeloid Cell Line, Tf-1," *Blood*, 86:4568-78.

Fawell et al., (1994), "Tat-Mediated Delivery of Heterologous Proteins into Cells," *Proc. Natl. Acad. Sci. USA*, 91:664-8.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gainsford et al., (1996), "Leptin Can Induce Proliferation, Differentiation, and Functional Activation of Hemopoietic Cells," *Proc. Natl. Acad. Sci. USA*, 93:14564-14568.

Gammon et al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et al., (1990), "Disseminated or Localized Growth of a Human B-Cell Tumor (Daudi) in SCID Mice," *Intl. J. Cancer*, 45:485.

Ghetie et al., (1997), "FcRn: The MHC Class I-Related Receptor that is More Than an IgG Transporter," *Immunology Today*, 18(12):592-598.

Goldwasser et al., (1971), "Purification of Erythropoietin," *Proc. Natl. Acad. Sci. USA*, 68:697-8.

Goldwasser et al., (1975), "Erythropoeitin: Assay and Study of its Mode of Action," *Methods Enzymol.*, 37(PtB):109-21.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Halin et al., (2002), "Enhancement of the Antitumor Activity of Interleukin-12 by Targeted Delivery to Neovasculature," *Nature Biotechnology*, 20:264-269.

Handgretinger et al., (2001), "Immunological Aspects of Haploidentical Stem Cell Transplantation in Children," *Ann. NY Acad. Sci.*, 938:340-57.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Henikoff et al., (1992), "Amino Acid Substitution Matrices from Protein Blocks," *Proc. Natl. Acad. Sci. USA*, 89:10915-10919.

Hilgers et al., (1999), "Sulfolipo-Cyclodextrin in Squalane-In-Water as a Novel and Safe Vaccine Adjuvant," *Vaccine*, 17:219-28.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hulett et al., (1994), "Molecular Basis of Fc Receptor Function," *Adv. Immunol.*, 57:1127.

Huston et al., (1988), "Protein Engineering of Antibody Binding Sites: Recovery of Specific Activity in an Anti-Digoxin Single-Chain Fv Analogue Produced In *Escherichia coli*," *Proc. Natl. Acad. Sci. USA*, 85:5879-5883.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Jacobs et al., (1985), "Isolation and Characterization of Genomic And cDNA Clones of Human Erythropoietin," *Nature*, 313:806-10.

Jefferis et al., (1990), "Molcular Definition of Interaction Sites on Human IgG for Fc Receptors huFcγR," *Mol. Immunol.*, 27(12):1237-1240.

Karlin et al., (1990), "Methods for Assessing the Statistical Significance of Molecular Sequence Features by Using General Scoring Schemes," *Proc. Natl. Acad. Sci. USA*, 87:2264-8.

Karlin et al., (1993), "Applications and Statistics for Multiple High-Scoring Segments in Molecular Sequences," *Proc. Natl. Acad. Sci. USA*, 90:5873-7.

Karpusas et al., (1997), "The Crystal Structure of Human Interferon β at 2.2-A Resolution," *Proc. Acad. Sci. USA*, 94:11813-11818.

Kelner et al., (1994), "Lymphotactin: A Cytokine that Represents a New Class of Chemokine," *Science*, 266:1395-9.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

Klinman et al., (1997), "Contribution of CpG Motifs to the Immunogenicity of DNA Vaccines," *J. Immunol.*, 158:3635-9.

Kuntz et al., (1982), "A Geometric Approach to Macromolecule-Ligand Interactions," *J. Mol. Biol.*, 161:269-88.

Kurtz, (1982), "A New Candidate for the Regulation of Erythropoiesis. Insulin-Like Growth Factor I," *FEBLAL.*, 149(1):105-8.

Lai et al., (1986), "Structural Characterization of Human Erythropoietin," *J. Biol. Chem.*, 261:3116-21.

Lai et al., (1998), "DNA Vaccines," *Crit. Rev. Immunol.*, 18:449-84.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et al., (1981), "DNA Sequence of a Major Human Leukocyte Interferon Gene," *Proc. Natl. Acad. Sci. USA*, 78:5435-9.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et al., (1996), "Cytokine Gene Therapy of Cancer Using Interleukin-12: Murine and Clinical Trials," *Ann. NY Acad, Sci.*, 795:440-54.

Macdougall et al., (1999), "Pharmacokinetics of Novel Erythropoiesis Stimulating Protein Compared with Epoetin Alfa in Dialysis Patients," *J. Am. Soc. Nephrol.*, 10:2392-5.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.

Maloy et al., (2001), "Regulatory T Cells in the Control of Immune Pathology," *Nature Immunol.*, 2:816-22.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et al., (1994), "Role of the Polymorphic Residues in HLA-DR Molecules in Allele-Specific Binding of Peptide Ligands," *J. Immunol.*, 152:4946-57.

Marshall et al., (1995), "Prediction of Peptide Affinity to HLA-DR Molecules," *Biomed. Pept. Proteins Nucleic Acids*, 1(3):157-62.

Martin et al., (2001), "Crystal Structure at 2.8 Å of an FcRn/Heterodimeric Fc Complex: Mechanism of pH-Dependent Binding," *Mol. Cell.*, 7(4):867-77.

McDonald, (1986), "Cloning, Sequencing, and Evolutionary Analysis of the Mouse Erythropoietin Gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-1 Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Mehrotra et al., (1993), "Effects of IL-12 on the Generation of Cytotoxic Activity in Human CD8+ T Lymphocytes," *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1977), "Purification of Human Erythropoietin," *J. Biol. Chem.*, 252:5558-64.

Miyake et al., (1988), "Synthesis of Recombinant Human Single-Chain Urokinase-Type Plasminogen Activator Variants Resistant to Plasmin and Thrombin," *J. Biochem.*, 104:643-647.

Morrison et al., (1984), "Chimeric Human Antibody Molecules: Mouse Antigen-Binding Domains with Human Constant Region Domains," *Proc. Natl. Acad. Sci. USA*, 81:6851-5.

Nagao et al., (1992), "Nucleotide Sequence of Rat Erythropoietin," *Biochem. Biophys. Acta*, 1171(1):99-102.

Nastala et al., (1994), "Recombinant IL-12 Administration Induces Tumor Regression in Association with IFN-γ Production," *J. Immunol.*, 153:1697-706.

Naughton et al., (1983), "Evidence for an Erythropoietin-Stimulating Factor in Patients with Renal and Hepatic Disease," *Acta. Haemat.*, 69:171-9.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Noguchi et al., (1994), "A Mouse Mutant P53 Product Recognized by CD4+ and CD8+ T Cells," *Proc. Natl. Acad. Sci. USA*, 91:3171-5.

Orlandi et al., (1989), "Cloning Immunoglobulin Variable Domains for Expression by the Polymerase Chain Reaction," *Proc. Natl. Acad. Sci. USA*, 86:3833-7.

Palmer et al., (2001), "Phase I Study of the BLP 25 (MUC1 Peptide) Liposomal Vaccine for Active Specific Immunotherapy in Stage IIIB/IV Non-Small-Cell Lung Cancer," *Clinical Lung Cancer*, 3(1):49-57.

Palucka et al., (1998), "Dendritic Cells as the Terminal Stage of Monocyte Differentiation," *J. Immunol.*, 160:4587-95.

Panina-Bordignon et al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlović-Kentera et al., (1980), "Effects of Prostaglandin Synthetase Inhibitors, Salt Overload and Renomedullary Dissection on the Hypoxia Stimulated Erythropoietin Production in Rats," *Exp. Hematol.*, 8(Supp. 8):283-92.

Pedley et al. (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferation of TCR-αβ+, TCR-γδ+ T Lymphocytes, and NK Cells," *J. Immunol.*, 149:3495-502.

Pluschke et al., (1996), "Molecular Cloning of a Human Melanoma-Associated Chondroitin Sulfate Proteoglycan," *Proc. Natl. Acad. Sci. USA*, 93:9710-5.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Radhakrishnan et al., (1996), "Zinc Mediated Dimer of Human Interferon-$\alpha_{2b}$ Revealed by X-Ray Crystallography," *Structure* 4(12):1453-63.

Ramachandran et al., (1968)"Conformation of Polypeptides and Proteins," *Adv. Prot. Chem.*, 23:283-299.

Rarey et al., (1995), "Time-Efficient Docking of Flexible Ligands into Active Sites Of Proteins," *Proc. Int. Conf. Intell. Syst. Mol. Biol.* 3:300-8.

Resegotti et al., (1981), "Treatment of Aplastic Anaemia with Methenolone, Stanozolol and Nandrolone. A Report of 130 Cases," *Pan. Med.*, 23:243-8.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Rothmann et al., (1982), "Erythropoietin-Dependent Erythrocytosis associated with Hepatic Angiosarcoma," *J. Surg. Oncol.*, 20:105-8.

Runkel et al., (1998), "Structural and Functional Differences Between Glycosylated and Non-Glycosylated Forms of Human Interferon-β (IFN-β)," *Pharmaceutical Res.*, 15:641-649.

Sakano et al., (1980), "Two Types of Somatic Recombination are Necessary for the Generation of Complete Immunoglobulin Heavy-Chain Genes," *Nature*, 286:676-683.

Säli et al., (1993), "Comparative Protein Modelling by Satisfaction of Spatial Restraints," *J. Mol. Biol.*, 234:779-815.

Schecter et al., (1997), "Tissue Factor is Induced by Monocyte Chemoattractant Protein-1 in Human Aortic Smooth Muscle And THP-1 Cells," *J. Biol. Chem.*, 272:28568-73.

Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Consdierable Within-Species Diversity," *Nucleic Acids Res.*, 16(17):8207-8211.

Simonsen et al., (1983), "Isolation and Expression of an Altered Mouse Dihydrofolate Reductase cDNA," *Proc. Natl. Acad. Sci. USA*, 80:2495-2499.

Smith et al., (1981), "Identification of Common Molecular Subsequences," *J. Mol. Biol.*, 147:195-197.

Soligo et al., (1998), "Expansion of Dendritic Cells Derived from Human CD34+ Cells in Static And Continuous Perfusion Cultures," *Br. J. Haematol.*, 101:352-63.

Spivak et al., (1989), "The In Vivo Metabolism of Recombinant Human Erythropoietin in The Rat," *Blood*, 73:90-9.

Sturniolo et al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a cDNA Encoding Bovine Erythropoietin and Analysis of Its Transcription in Selected Tissues," *Gene*, 171:275-80.

Takahashi et al., (2000), "Immunologic Self-Tolerance Maintained by CD25+ CD4+ Regulatory T Cells Constitutively Expressing Cytotoxic T Lymphocyte-Associated Antigen 4," *J. Exp. Med.*, 192(2):303-309.

Takai, (2002), "Roles of Fc Receptors in Autoimmunity," *Nat. Rev. Immunol.*, 2(8):580-92.

Taniguchi et al., (1980), "Expression of the Human Fibroblast Interferon Gene in *Escherichia coli*," *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Natl. Acad. Sci. USA*, 93:250-4.

Van Den Eynde et al., (1989), "Presence on a Human Melanoma of Multiple Antigens Recognized By Autologous CTL," *Int. J. Cancer*, 44:634-40.

Van Der Bruggen et al., (1991), "A Gene Encoding an Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:5145-5164.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL_2) Variant, demonstrates Selective Activation of Human and Chimpanzee T Cells Relative to NK Cells but Shows Less Selectivity for T Cells from Monkeys and Rodents," *ASCO Annual Meeting*, Abstract 1051.

Woof et al., (1986), "Localisation of the Monocyte-Binding Region on Human Immunoglobulin G," *Mol. Immunol.*, 23:319-30.

Wyatt et al., (1998), "The Antigenic Structure of the HIV gp120 Envelope Glycoprotein," *Nature*, 393:705-11.

Wysocka et al., (1995), "Interleukin-12 is Required for Interferon-γ Production and Lethality in Lipopolysaccharide-Induced Shock in Mice," *Eur. J. Immuno.*, 25:672-6.

Yan et al., (1996), "Characterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-I) by Mutagenesis," *J. Biol. Chem.*, 269:15918-24.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

Adkins et al., (1998), "Edrecolomab (Monoclonal Antibody 17-1A)," *Drugs*, 56(4): 619-626.

Connor et al., (2004), "Ex Vivo Evaluation of Anti-EpCAM Immunocytokine huKS-IL2 in Ovarian Cancer," *J. Immunother.*, 27(3):211-219.

Mateo et al., (2000), "Removal of Amphipathic Epitopes from Genetically Engineered Antibodies: Production of Modified immunoglobulins with Reduced Immunogenicity," *Hybridoma*, 19(6):463-471.

Schwartzberg, (2001), "Clinical Experience with Edrecolomab: A Monoclonal Antibody Therapy for Colorectal Carcinoma," *Critical Reviews in Oncology/Hematology*, 40:17-24.

Went et al., (2004), "Frequent EpCam Protein Expression in Human Carcinomas," *Human Pathology*, 35(1):122-128.

Balzar, M. et al., "The biology of the 17-1A antigen (Ep-CAM)," *J. Molecular Medicine* (1999) 77:699-712.

Beiboer, S. H. W. et al., "Guided Selection of a Pan Carcinoma Specific Antibody Reveals Similar Binding Characteristics Yet Structural Divergence Between The Original Murine Antibody and Its Human Equivalent," *Journal Of Molecular Biology*, (2000), 296(3):833-849.

Roovers, R. C. et al., "High-Affinity Recombinant Phage Antibodies to the Pan-Carcinoma Marker Epithelial Glycoprotein-2 for Tumour Targeting," *British Journal Of Cancer*, (1998), 78 (11):1407-1416.

Simon, B. et al., "Epithelial Glycoprotein is a Member of a Family of Epithelial Cell Surface Antigens Homologous to Nidogen, a Matrix Adhesion Protein," *Proc. Natl. Acad. Sci.* (1990) 87:2755-2759.

RECOMBINANT TUMOR SPECIFIC ANTIBODY AND USE THEREOF

RELATED APPLICATIONS

This application is a divisional application of U.S. Ser. No. 10/138,727, filed May 3, 2002 now U.S. Pat. No. 6,969,517, which claims the benefit of and priority to U.S. Ser. No. 60/288,564, filed May 3, 2001, the disclosures of each of which are incorporated by reference herein.

FIELD OF THE INVENTION

The invention relates generally to recombinant antibodies. More particulary, the invention relates to recombinant antibodies that specifically bind human Epithelial Cell Adhesion Molecule, and to their use as diagnostic, prognostic and therapeutic agents.

BACKGROUND OF THE INVENTION

There has been significant progress in the development of antibody-based therapies over the years. For example, investigators have identified not only a variety of cancer-specific markers but also a variety of antibodies that bind specifically to those markers. Antibodies can be used to deliver certain molecules, for example, a toxin or an immune stimulatory moiety, for example, a cytokine, to a cancer cell expressing the marker so as to selectively kill the cancer cell (see, e.g., U.S. Pat. Nos. 5,541,087; and 5,650,150).

The KS-¼ antibody is a mouse-derived monoclonal antibody directed against human epithelial cell adhesion molecule (EpCAM). EpCAM is expressed at very low levels on the apical surface of certain epithelial cells. For example, EpCAM is expressed on intestinal cells on the cell surface facing toward ingested food and away from the circulation, where it would not be accessible to most proteins and cells of the immune system (Balzar et al. [1999] J. Mol. Med. 77:699-712).

Under certain circumstances, however, EpCAM is highly expressed on certain cells, for example, tumor cells of epithelial origin. Typically, these tumor cells have lose their polarity with the result that EpCAM is expressed over the entire surface of the cell. Thus, EpCAM is a convenient tumor-specific marker for directing antibody-based immune-stimulatory moieties to tumor cells (Simon et al. [1990] Proc. Nat. Acad. Sci. USA 78:2755-2759; Perez et al. [1989] J. Immunol. 142:3662-3667).

However, antibodies can have an associated immunogenicity in the host mammal. This is more likely to occur when the antibodies are not autologous. Consequently, the effectiveness of antibody-based therapies often is by an immunogenic response directed against the antibody. The immunogenic response typically is increased when the antibody is derived in whole or in part from a mammal different than the host mammal, e.g., when the antibody is derived from a mouse and the recipient is a human. Accordingly, it may be helpful to modify mouse-derived antibodies to more closely resemble human antibodies, so as to reduce or minimize the immunogenicity of the mouse-derived antibody.

Although a variety of approaches have been developed, including, for example, chimeric antibodies, antibody humanization and antibody veneering, Accordingly, there is a need in the art for antibodies that bind to cancer specific markers and that have reduced immunogenicity when administered to a human. Further, there is a need in the art for antibodies that deliver toxins or immune stimulatory moieties, for example, as fusion proteins or immune conjugates to a cancer specific marker to selectively kill the tumor cell.

SUMMARY OF THE INVENTION

The present invention is based, in part, upon the identification of recombinant antibodies that specifically bind human EpCAM but are less immunogenic in humans than the template, murine anti-EpCAM antibodies. In particular, the invention provides recombinant KS antibodies in which the amino acid sequences defining one or more framework regions and/or complementarity determining regions have been modified to reduce their immunogenicity in humans.

As used herein, the terms "antibody" and "immunoglobulin" are understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof.

As used herein, the terms "bind specifically," "specifically bind" and "specific binding" are understood to mean that the antibody has a binding affinity for a particular antigen of at least about $10^6$ M$^{-1}$, more preferably, at least about $10^7$ M$^{-1}$, more preferably at least about $10^8$ M$^{-1}$, and most preferably at least about $10^{10}$ M$^{-1}$.

As used herein, the terms "Complementarity-Determining Regions" and "CDRs" are understood to mean the hypervariable regions or loops of an immunoglobulin variable region that interact primarily with an antigen. The immunoglobulin heavy chain variable region ($V_H$) and immunoglobulin light chain variable region ($V_L$) both contain three CDRs interposed between framework regions, as shown in FIG. 1. For example, with reference to the amino acid sequence defining the immunoglobulin light chain variable of the KS-¼ antibody as shown in SEQ ID NO: 1, the CDRs are defined by the amino acid sequences from Ser24 to Leu33 (CDR1), from Asp49 to Ser55 (CDR2), and from His88 to Thr96 (CDR3). With reference to the amino acid sequence defining the immunoglobulin heavy chain variable region of the KS-¼ antibody as shown in SEQ ID NO: 2, the CDRs are defined by the amino acid sequences from Gly26 to Asn35 (CDR1), from Trp50 to Gly66 (CDR2), and from Phe99 to Tyr105 (CDR3). The corresponding CDRs of the other antibodies described herein are shown in FIGS. 1A-1C after alignment with the corresponding KS-¼ heavy or light chain sequence.

As used herein, the terms "Framework Regions" and "FRs" are understood to mean the regions an immunoglobulin variable region adjacent to the Complementarity-Determining Regions. The immunoglobulin heavy chain variable region ($V_H$) and immunoglobulin light chain variable region ($V_L$) both contain four FRs, as shown in FIG. 1. For example, with reference to the amino acid sequence defining the immunoglobulin light chain variable of the of the KS-¼ antibody as shown in SEQ ID NO: 1, the FRs are defined by the amino acid sequences from Gln1 to Cys23 (FR1), from Trp34 to Phe 48 (FR2), from Gly56 to Cys87 (FR3), and from Phe97 to Lys106 (FR4). With reference to the amino acid sequence defining the immunoglobulin heavy chain variable region of the KS-¼ antibody as shown in SEQ ID NO: 2, the FRs are defined by the amino acid sequences from Gln1 to Ser25 (FR1), from Trp36 to Gly49 (FR2), from Arg67 to Arg98 (FR3), and from Trp 106 to Ser 116 (FR4). The FRs of the other antibodies described herein are shown in FIGS. 1A-1C after alignment with the corresponding KS-¼ heavy or light chain sequence.

As used herein, the term "KS antibody" is understood to mean an antibody that binds specifically to the same human EpCAM antigen bound by murine antibody KS-¼ expressed by a hybridoma (see, for example, Cancer Res. 1984, 44 ((2):681-7). The KS antibody preferably comprises (i) an amino acid sequence of SASSSVSY (amino acids 24-31 of SEQ ID NO: 1) defining at least a portion of an immunoglobulin light chain CDR1 sequence, (ii) an amino acid sequence of DTSNLAS (amino acids 49-55 of SEQ ID NO: 1) defining at least a portion of an immunoglobulin light chain CDR2 sequence, (iii) an amino acid sequence of HQRSGYPYT (amino acids 88-96 of SEQ ID NO: 1) defining at least a portion of an immunoglobulin light chain CDR3 sequence, (iv) an amino acid sequence of GYTFTNYGMN (amino acids 26-35 of SEQ ID NO: 2) defining at least a portion of an immunoglobulin heavy chain CDR1 sequence, (v) an amino acid sequence of WINTYTGEPTYAD (amino acids 50-62 of SEQ ID NO: 2) defining at least a portion of an immunoglobulin heavy chain CDR2 sequence, or (vi) an amino acid sequence of SKGDY (amino acids 101-105 of SEQ ID NO: 2) defining at least a portion of an immunoglobulin heavy chain CDR3 sequence, or any combination of the foregoing.

In one aspect, the invention provides a recombinant antibody that specifically binds EpCAM, wherein the antibody comprises an amino acid sequence, a portion of which defines a framework region in an immunoglobulin $V_L$ domain. In one embodiment, the framework region (FR1) is defined by amino acid residues 1-23 of SEQ ID NO: 5, wherein Xaa1 is Q or E, Xaa3 is L or V, Xaa10 is I or T, Xaa11 is M or L, Xaa13 is A or L, Xaa18 is K or R, or Xaa21 is M or L, provided that at least one of the amino acid residues at positions Xaa1, Xaa3, Xaa10, Xaa11, Xaa13, Xaa18, or Xaa21 is not the same as the amino acid at the corresponding position in SEQ ID NO: 1. The amino acids at each of the positions are denoted by the standard single letter code.

In another embodiment, the framework region (FR2) is defined by amino acid residues 34-48 of SEQ ID NO: 5, wherein Xaa41 is S or Q, Xaa42 is S or A, Xaa45 is P or L, or Xaa46 is W or L, provided that at least one of the amino acid residues at positions Xaa41, Xaa42, Xaa45, or Xaa46 is not the same as the amino acid at the corresponding position in SEQ ID NO: 1.

In another embodiment, the framework region (FR3) is defined by amino acid residues 56-87 of SEQ ID NO: 5, wherein Xaa57 is F or I, Xaa69 is S or D, Xaa71 is S or T, Xaa73 is I or T, Xaa77 is M or L, Xaa79 is A or P, Xaa82 is A or F, or Xaa84 is T or V, provided that at least one of the amino acid residues at positions Xaa57, Xaa69, Xaa71, Xaa73, Xaa77, Xaa79, Xaa82, or Xaa84 is not the same as the amino acid at the corresponding position in SEQ ID NO: 1.

In another aspect, the invention provides a recombinant antibody that specifically binds EpCAM, wherein the antibody comprises an amino acid sequence, a portion of which defines a framework region in an immunoglobulin $V_L$ domain. In one embodiment, the framework region (FR1) is defined by amino acid residues 1-25 of SEQ ID NO: 6, wherein Xaa2 is I or V, Xaa9 is P or A, Xaa11 is L or V, or Xaa17 is T or S, provided that at least one of the amino acid residues at positions Xaa2, Xaa9, Xaa11 or Xaa17 is not the same as the amino acid at the corresponding position in SEQ ID NO: 2.

In another embodiment, the framework region (FR2) is defined by amino acid residues 36-49 of SEQ ID NO: 6, wherein Xaa38 is K or R, Xaa40 is T or A, or Xaa46 is K or E, provided that at least one of the amino acid residues at positions Xaa38, Xaa40, Xaa46 is not the same as the amino acid at the corresponding position in SEQ ID NO: 2.

In another embodiment, the framework region (FR3) is defined by amino acid residues 67-98 of SEQ ID NO: 6, wherein Xaa68 is F or V, Xaa69 is A or T, Xaa70 is F or I, Xaa73 is E or D, Xaa76 is A or T, Xaa80 is F or Y, Xaa83 is I or L, Xaa84 is N or S, Xaa85 is N or S, Xaa88 is N, A or S, Xaa91 is M or T, or Xaa93 is T or V, provided that at least one of the amino acid residues at positions Xaa68, Xaa69, Xaa70, Xaa73, Xaa76, Xaa80, Xaa83, Xaa84, Xaa85, Xaa88, Xaa91 or Xaa93 is not the same as the amino acid at the corresponding position in SEQ ID NO: 2. In another embodiment, the framework region (FR4) is defined by amino acid residues 106-116 of SEQ ID NO: 6, wherein Xaa108 is Q or T.

In another embodiment, the immunoglobulin $V_L$ domain comprises an FR1 sequence selected from the group consisting of: (i) amino acid residues 1-23 of SEQ ID NO: 9; and (ii) amino acid residues 1-23 of SEQ ID NO: 8. In another embodiment, the immonoglobulin $V_H$ domains comprises an FR sequence defined by amino acid residues 1-25 of SEQ ID NO: 18 and or an FR sequence defined by amino acid residues 67-98 of SEQ ID NO: 18. More preferably, the $V_L$ domain comprises an amino acid sequence defined by amino acids 1-106 of SEQ ID NO: 9 and/or the $V_H$ domain comprises an amino acid sequence defined by amino acids 1-116 of SEQ ID NO: 18.

Furthermore, the antibody optionally may include an amino acid sequence defining at least a portion of a CDR sequence including, for example, (i) amino acid residues 24-31 of SEQ ID NO: 1; (ii) amino acid residues 49-55 of SEQ ID NO: 1; and/or (iii) amino acid residues 88-96 of SEQ ID NO: 1. Similarly, the antibody optionally may include an amino acid sequence defining at least a portion of a CDR sequence including, for example, (i) amino acid residues 26-35 of SEQ ID NO: 2; (ii) amino acid residues 50-62 of SEQ ID NO: 2; and/or iii) amino acid residues 101-105 of SEQ ID NO: 2.

In another embodiment, the antibody comprises the antigen targeting portion of an antibody-cytokine fusion protein. The cytokine preferably is an interleukin and more preferably is interleukin-2.

In another aspect, the invention provides an expression vector encoding at least a portion of the antibody of the invention. In a preferred embodiment, the expression vector comprises the nucleotide sequence set forth in SEQ ID NO: 40.

In another aspect, the invention provides a method of diagnosing, prognosing and/or treating a human patient having a disease associated with over-expression of EpCAM (for example, a disease in which EpCAM is present at a higher level in diseased tissue relative to tissue without that disease). The method comprises administering one of the antibodies of the invention to an individual in need of such diagnosis, prognosis or treatment.

The antibody optionally includes a diagnostic and/or therapeutic agent attached thereto. The agent may be fused to the antibody to produce a fusion protein. Alternatively, the agent may be chemically coupled to the antibody to produce an immuno-conjugate. It is contemplated that the agent may include, for example, a toxin, radiolabel, cytokine, imaging agent or the like. In a preferred embodiment, the antibody of the invention is fused as a fusion protein to a cytokine. Preferred cytokines preferably include interleukins such as interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM- CSF), granulocyte colony stimulating factor (G-CSF) and erythropoeitin, tumor necrosis factors (TNF) such as TNFα, lymphokines such as lymphotoxin, regulators of metabolic processes such as leptin, interferons such as interferon α, interferon β, and interferon γ, and chemokines. Preferably, the antibody-cytokine fusion protein displays cytokine biological activity.

DESCRIPTION OF THE DRAWINGS

Figure 1A:
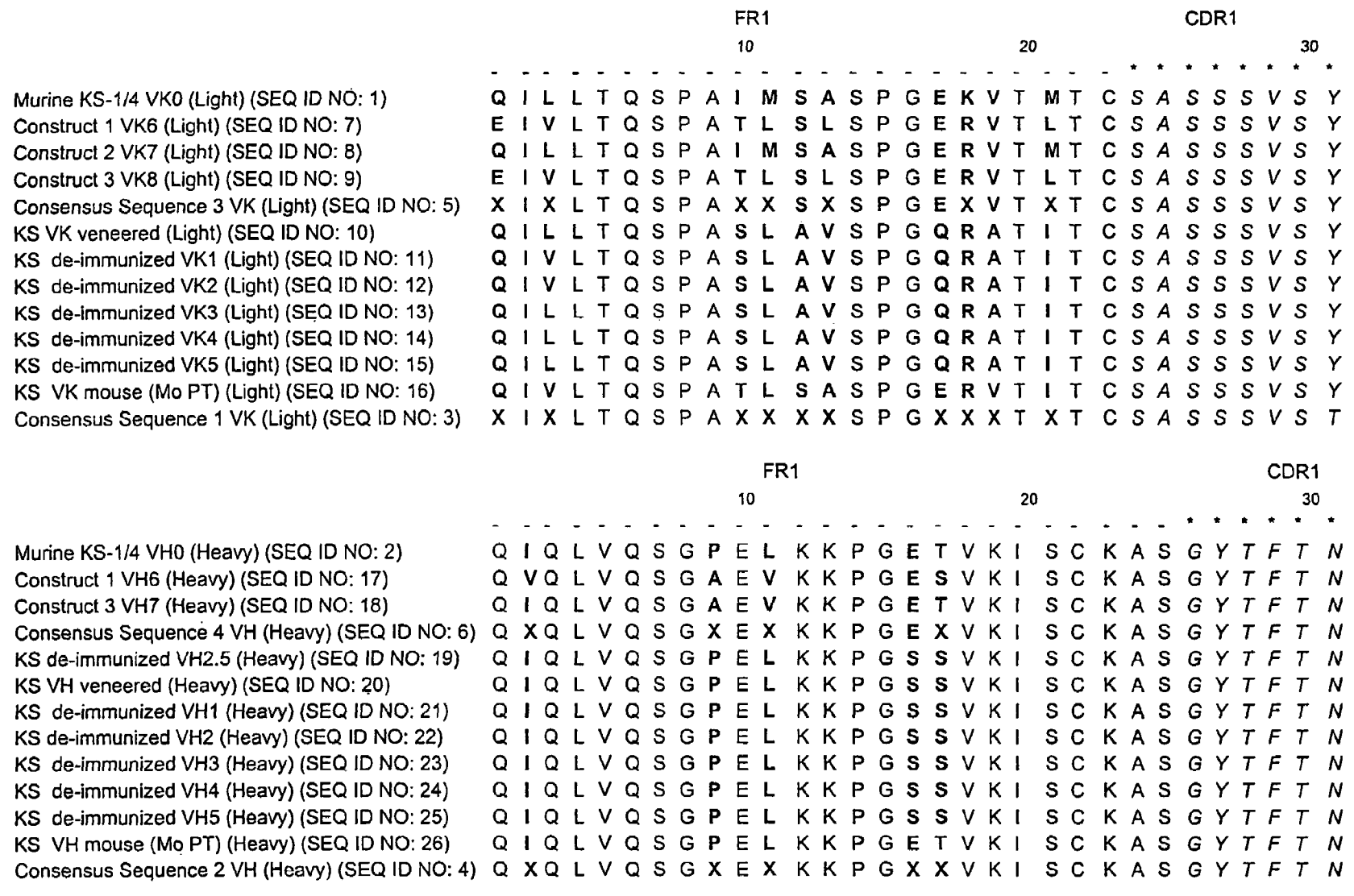
Figure 1C:
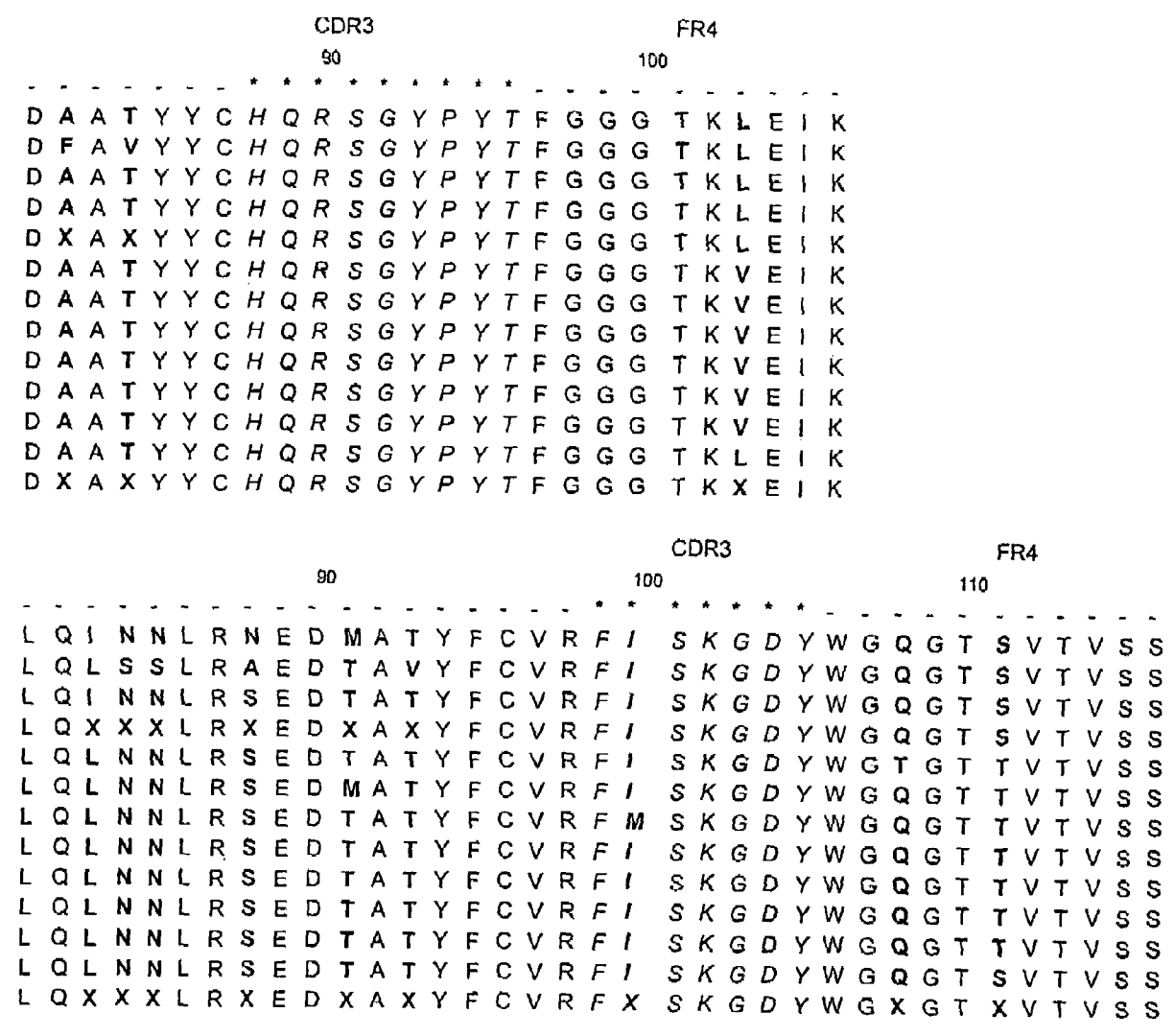

FIGS. 1A, 1B and 1C show an alignment of light and heavy chain variants and consensus sequences of KS antibodies. The immunoglobulin Framework Regions (FR1-FR4) are denoted by -. The immunoglobulin Complementarity Determining Regions (CDR1-CDR3) are denoted by *. Individual KS antibody light chain V region segments are referred to as "VK," wherein K refers to the fact that the light chain is a kappa chain. Individual KS antibody heavy chain V region segments are referred to as "$V_H$." Substitutable amino acids are denoted by "X" in the consensus sequences.

DETAILED DESCRIPTION OF THE INVENTION

Figure 1B:
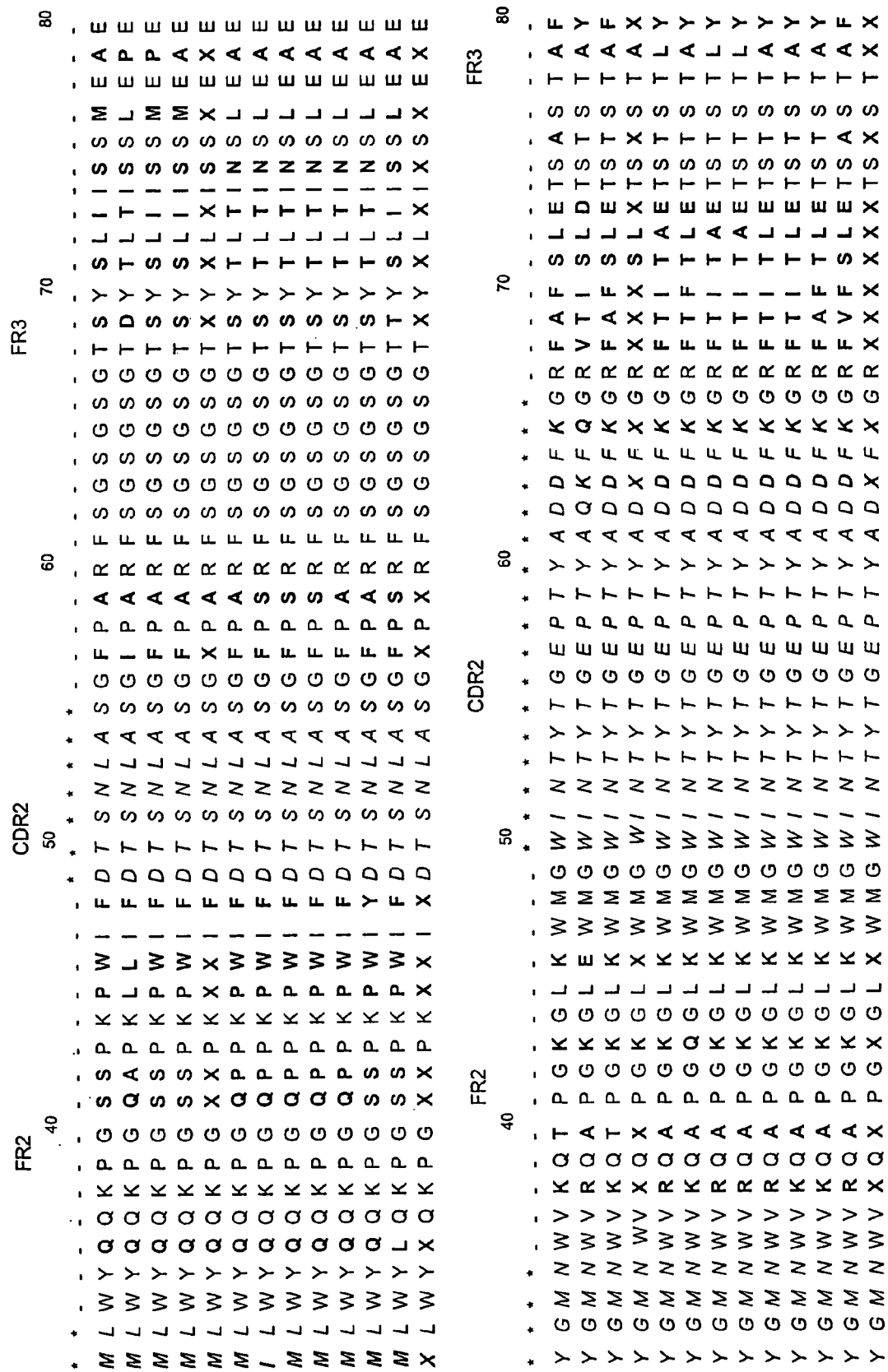

The present invention provides recombinant antibodies that specifically bind human Epithelial Cell Adhesion Molecule (EpCAM). Preferred antibodies of the invention have altered variable regions that result in reduced immunogenicity in humans. Antibody variable regions of the invention are particularly useful to target antibodies and antibody fusion proteins to tumor tissues that over-express EpCAM in human patients. In preferred embodiments, an antibody of the invention is fused to a cytokine to produce an immuno-cytokine.

Protein Sequences of the Invention

The present invention discloses a family of antibody variable region or V region sequences that, when appropriately heterodimerized, bind to human epithelial cell adhesion molecule (EpCAM) also known as KS antigen or KSA. Preferred proteins of the invention are useful for treating human patients as described herein. Accordingly, preferred KS antibody variants are humanized, deimmunized, or both, in order to reduce their immunogenicity when administered to a human. According to the invention, murine KS antibodies can be deimmunized or humanized, for example, by using deimmunization methods in which potential T cell epitopes are eliminated or weakened by introduction of mutations that reduce binding of a peptide epitope to an MHC Class II molecule (see, for example WO98/52976, and WO00/34317), or by using methods in which non-human T cell epitopes are mutated so that they correspond to human self epitopes that are present in human antibodies (see, for example, U.S. Pat. No. 5,712,120).

I. Variable Light Chain

The recombinant anti-EpCAM antibody has an immunoglobulin variable light chain sequence having the following amino acid sequence:

```
                                              (SEQ ID NO: 3)
X-I-X-L-T-Q-S-P-A-X-X-X-X-S-P-G-X-X-X-T-X-T-C-S-A-

S-S-S-V-S-T-X-L-W-Y-X-Q-K-P-G-X-X-P-K-X-X-I-X-D-T-

S-N-L-A-S-G-X-P-X-R-F-S-G-S-G-T-X-Y-X-L-X-I-X-S-X-

E-X-E-D-X-A-X-Y-Y-C-H-Q-R-S-G-Y-P-Y-T-F-G-G-G-T-K-

X-E-I-K.
```

In a preferred embodiment, the recombinant anti-EpCAM antibody has an amino acid sequence defining an immunoglobulin light chain FR1, which is represented by residues 1 to 23 of SEQ ID NO: 3, namely, X-I-X-L-T-Q-S-P-A-X-X-X-X-S-P-G-X-X-X-T-X-T-C. More particularly, the recombinant anti-EpCAM antibody has at least one of the following amino acids in the FR1 region: Q or E at position Xaa1; L or V at position Xaa3; I, T or S at position Xaa10; M or L at position Xaa11; S or A at position Xaa12; A, L or V at position Xaa13; E or Q at position Xaa17, K or R at position Xaa18, V or A at position Xaa19; and, M, L or I at position Xaa21. More preferably, the recombinant anti-EpCAM antibody has at least one of the following amino acid substitutions in the FR1 region: E at position Xaa1; V at position Xaa3; T or S at position Xaa10; L at position Xaa11; A at position Xaa12; L or V at position Xaa13; Q at position Xaa17, R at position Xaa18, A at position Xaa19; and, L or I at position Xaa21.

In another embodiment, the recombinant anti-EpCAM antibody of the invention has an amino acid sequence defining an immunoglobulin light chain CDR1, which is represented by residues 24 to 33 of SEQ ID NO: 3, namely S-A-S-S-S-V-S-T-X-L. More particularly, the recombinant anti-EpCAM antibody of the invention has one of the following amino acids in the CDR1 region: M or I at position Xaa32. More preferably, the recombinant anti-EpCAM antibody has an amino acid substitution in the CDR1 region, for example, I at position Xaa32.

In another embodiment, the recombinant anti-EpCAM antibody has an amino acid sequence defining an immunoglobulin light chain FR2, which is represented by residues 34 to 48 of SEQ ID NO: 3, namely W-Y-X-Q-K-P-G-X-X-P-K-X-X-I-X. More particularly, the recombinant anti-EpCAM antibody has at least one of the following amino acids in the FR2 region: Q or L at position Xaa36; S or Q at position Xaa41; S, A or P at position Xaa42; P or L at position Xaa45; W or L at position Xaa46; and, F or Y at position Xaa48. More preferably, the recombinant anti-EpCAM antibody has at least one of the following amino acid substitutions in the FR2 region: L at position Xaa36; Q at position Xaa41; A or P at position Xaa42; L at position Xaa45; L at position Xaa46; and, Y at position Xaa48.

In another embodiment, the recombinant anti-EpCAM antibody has an amino acid sequence defining an immunoglobulin light chain FR3, which is represented by residues 56 to 87 of SEQ ID NO: 3, namely, G-X-P-X-R-F-S-G-S-G-S-G-T-X-Y-X-L-X-I-X-S-X-E-X-E-D-X-A-X-Y-Y-C. More particularly, the recombinant anti-EpCAM antibody has at least one of the following amino acids in the FR3 region: F or I at position Xaa57; A or S at position Xaa59; S, D or T at position Xaa69; I or T at position Xaa71; I or T at position Xaa73; S or N at position Xaa75; M or L at position Xaa77; A or P at position Xaa79; A or F at position Xaa82; and, T or V at position Xaa84. More preferably, the recombinant anti-EpCAM antibody has at least one of the following amino acid substitution in the FR3 region: I at position Xaa57; S at position Xaa59; D or T at position Xaa69; T at position Xaa71; T at position Xaa73; N at position Xaa75; L at position Xaa77; P at position Xaa79; F at position Xaa82; and, V at position Xaa84.

In another embodiment, the recombinant anti-EpCAM antibody has an amino acid sequence defining an immunoglobulin light chain FR4, which is represented by residues 97 to 106 of SEQ ID NO: 3, namely, F-G-G-G-T-K-X-E-I-K. More particularly, the recombinant anti-EpCAM antibody of the invention has at least one of the following amino acids in the FR4 region, for example, L or V at position Xaa103. Accordingly, the recombinant anti-EpCAM antibody of the invention has an amino acid substitution in the FR4 region, for example, V at position Xaa103.

II. Variable Heavy Chain

The recombinant anti-EpCAM antibody has an immunoglobulin variable heavy chain sequence having the following amino acid sequence:

(SEQ ID NO: 4)
Q-X-Q-L-V-Q-S-G-X-E-X-K-K-P-G-X-X-V-K-I-S-C-K-A-S-
G-Y-T-F-T-N-Y-G-M-N-W-V-X-Q-X-P-G-X-G-L-X-W-M-G-W-
I-N-T-Y-T-G-E-P-T-Y-A-D-X-F-X-G-R-X-X-X-X-X-T-S-
X-S-T-X-X-L-Q-X-X-X-L-R-X-E-D-X-A-X-Y-F-C-V-R-F-X-
S-K-G-D-Y-W-G-X-G-T-X-V-T-V-S-S

In a preferred embodiment, the recombinant anti-EpCAM antibody has an amino acid sequence defining an immunoglobulin heavy chain FR1, which is represented by residues 1 to 25 of SEQ ID NO: 4, namely Q-X-Q-L-V-Q-S-G-X-E-X-K-K-P-G-X-X-V-K-I-S-C-K-A-S. More particularly, the recombinant anti-EpCAM antibody has at least one of the following amino acids in the FR1 region: I or V at position Xaa2; P or A at position Xaa9; L or V at position Xaa11; E or S at position Xaa16; and, T or S at position Xaa17. More preferably, the recombinant anti-EpCAM antibody has at least one of the following amino acid substitutions in the FR1 region: V at position Xaa2; A at position Xaa9; V at position Xaa11; S at position Xaa16; and, S at position Xaa17.

In a preferred embodiment, the recombinant anti-EpCAM antibody has an amino acid sequence defining an immunoglobulin heavy chain FR2, which is represented by residues 36 to 49 of SEQ ID NO: 4, W-V-X-Q-X-P-G-X-G-L-X-W-M-G. More particularly, the recombinant anti-EpCAM antibody has at least one of the following amino acids in the FR2 region: K or R at position Xaa38; T or A at position Xaa40; K or Q at position Xaa43; and, K or E at position Xaa46. More preferably, the recombinant anti-EpCAM antibody has at least one of the following amino acid substitutions in the FR2 region: R at position Xaa38; A at position Xaa40; Q at position Xaa43; and, E at position Xaa46.

In a preferred embodiment, the recombinant anti-EpCAM antibody has an amino acid sequence defining an immunoglobulin heavy chain CDR2, which is represented by residues 50 to 66 of SEQ ID NO: 4, namely W-I-N-T-Y-T-G-E-P-T-Y-A-D-X-F-X-G. More particularly, the recombinant anti-EpCAM antibody has at least one of the following amino acids in the CDR2 region: D or K at position Xaa63; and, K or Q at position Xaa65. More preferably, the recombinant anti-EpCAM antibody has at least one of the following amino acid substitutions in the CDR2 region: K at position Xaa63; and, Q at position Xaa65.

In a preferred embodiment, the recombinant anti-EpCAM antibody has an amino acid sequence defining an immunoglobulin heavy chain FR3, which is represented by residues 67 to 98 of SEQ ID NO: 4, namely R-X-X-X-X-X-X-T-S-X-S-T-X-X-L-Q-X-X-X-L-R-X-E-D-X-A-X-Y-F-C-V-R. More particularly, the recombinant anti-EpCAM antibody of the invention has at least one of the following amino acids in the FR3 region: F or V at position Xaa68, A, T or V at position Xaa69; F or I at position Xaa70; S or T at position Xaa71; L or A at position Xaa72; E or D at position Xaa73; A or T at position Xaa76; A or L at position Xaa79; F or Y at position Xaa80; I or L at position Xaa83; N or S at position Xaa84; N or S at position Xaa85; N, A or S at position Xaa88; M or T at position Xaa91; and, T or V at position Xaa93. More preferably, the recombinant anti-EpCAM antibody has at least one of the following amino acid substitutions in the FR3 region: V at position Xaa68, T or V at position Xaa69; I at position Xaa70; T at position Xaa71; A at position Xaa72; D at position Xaa73; T at position Xaa76; L at position Xaa79; Y at position Xaa80; L at position Xaa83; S at position Xaa84; S at position Xaa85; A or S at position Xaa88; T at position Xaa91; and, V at position Xaa93.

In a preferred embodiment, the recombinant anti-EpCAM antibody has an amino acid sequence defining an immunoglobulin heavy chain CDR3, which is represented by residues 99 to 105 of SEQ ID NO: 4, namely F-X-S-K-G-D-Y. More particularly, the recombinant anti-EpCAM antibody has at least one of the following amino acids in the CDR3 region, for example, I or M at position Xaa100. More preferably, the recombinant anti-EpCAM antibody has an amino acid substitution in the CDR3 region, for example, M at position Xaa100.

In a preferred embodiment, the recombinant anti-EpCAM antibody has an amino acid sequence defining an immunoglobulin heavy chain FR4, which is represented by residues 106 to 116 of SEQ ID NO: 4, namely W-G-X-G-T-X-V-T-V-S-S. More particularly, the recombinant anti-EpCAM antibody has at least one of the following amino acids in the FR4 region: Q or T at position Xaa108; and, S or T at position X111. More preferably, the recombinant anti-EpCAM antibody has at least one of the following amino acid substitutions in the FR4 region: T at position Xaa108; and, T at position X111.

III. Refined Variable Light Chain

In another embodiment, the recombinant anti-EpCAM antibody has an immunoglobulin variable light chain sequence having the following amino acid sequence:

(SEQ ID NO: 5)
X-I-X-L-T-Q-S-P-A-X-X-S-X-S-P-G-E-X-V-T-X-T-C-S-A-
S-S-S-V-S-Y-M-L-W-Y-Q-Q-K-P-G-X-X-P-K-X-X-I-F-D-T-
S-N-L-A-S-G-X-P-A-R-F-S-G-S-G-S-G-T-X-Y-X-L-X-I-S-
S-X-E-X-E-D-X-A-X-Y-Y-C-H-Q-R-S-G-Y-P-Y-T-F-G-G-G-
T-K-L-E-I-K

In a preferred embodiment, the recombinant anti-EpCAM antibody has an amino acid sequence defining an immunoglobulin light chain FR1, which is represented by residues 1 to 23 of SEQ ID NO: 5, namely X-I-X-L-T-Q-S-P-A-X-X-S-X-S-P-G-E-X-V-T-X-T-C. More particularly, the recombinant anti-EpCAM antibody has at least one of the following amino acids in the FR1 region: Q or E at position Xaa1; L or V at position Xaa3; I or T at position Xaa10; M or L at position Xaa11; A or L at position Xaa13; K or R at position Xaa18; and, M or L at position Xaa2 1. More preferably, the recombinant anti-EpCAM antibody has at least one of the following amino acid substitutions in the FR1 region: E at position Xaa1; V at position Xaa3; T at position Xaa10; L at position Xaa11; L at position Xaa13; R at position Xaa18; and, L at position Xaa21.

In another preferred embodiment, the recombinant anti-EpCAM antibody has an amino acid sequence defining an immunoglobulin light FR1 having at least one of the following amino acids in the FR1 region: Q or E at position Xaa1; A or L at position Xaa11; and, M or L at position Xaa21. More preferably, the recombinant anti-EpCAM antibody has an amino acid sequence defining an immunoglobulin light FR1 having at least one of the following substitutions in the FR1 region: E at position Xaa1; L at position Xaa11; and, L at position Xaa21.

In a preferred embodiment, the recombinant anti-EpCAM antibody has an amino acid sequence defining an immunoglobulin light chain FR2, which is represented by residues 34 to 48 of SEQ ID NO: 5, namely W-Y-Q-Q-K-P-G-X-X-P-K-X-X-I-F. More preferably, the recombinant anti-EpCAM antibody has at least one of the following amino acids in the FR2 region: S or Q at position Xaa41; S or A at position Xaa42; P or L at position Xaa45; and, W or L at position Xaa46. More preferably, the recombinant anti-EpCAM antibody has at least one of the following amino acid substitutions in the FR2 region: Q at position Xaa41; A at position Xaa42; L at position Xaa45; and, L at position Xaa46.

In another preferred embodiment, the recombinant anti-EpCAM antibody of the invention has an amino acid sequence defining an immunoglobulin light FR2 having at least one of the following amino acids in the FR2 region: S or A at position Xaa42; P or L at position Xaa45; and, W or L at position Xaa46. More preferably, the recombinant anti-EpCAM antibody has an amino acid sequence defining an immunoglobulin light FR2 having at least one of the following substitutions in the FR2 region: A at position Xaa42; L at position Xaa45; and, L at position Xaa46.

In a preferred embodiment, the recombinant anti-EpCAM antibody has an amino acid sequence defining an immunoglobulin light chain FR3, which is represented by residues 56 to 87 of SEQ ID NO: 5, namely G-X-P-A-R-F-S-G-S-G-S-G-T-X-Y-X-L-X-I-S-S-X-E-X-E-D-X-A-X-Y-Y-C. More particularly, the recombinant anti-EpCAM antibody has at least one of the following amino acids in the FR3 region: F or I at position Xaa57; S or D at position Xaa69; S or T at position Xaa71; I or T at position Xaa73; M or L at position Xaa77; A or P at position Xaa79; A or F at position Xaa82; and, T or V at position Xaa84. More preferably, the recombinant anti-EpCAM antibody has at least one of the following amino acid substitution in the FR3 region: I at position Xaa57; D at position Xaa69; T at position Xaa71; T at position Xaa73; L at position Xaa77; P at position Xaa79; F at position Xaa82; and, V at position Xaa84.

In another preferred embodiment, the recombinant anti-EpCAM antibody of the invention has an amino acid sequence defining an immunoglobulin light FR3 having at least one of the following amino acids in the FR3 region: F or I at position Xaa57; S or D at position Xaa69; A or P at position Xaa79; A or F at position Xaa82; and, T or V at position Xaa84. More preferably, the recombinant anti-EpCAM antibody has an amino acid sequence defining an immunoglobulin light FR3 having at least one of the following substitutions in the FR3 region: I at position Xaa57; D at position Xaa69; P at position Xaa79; F at position Xaa82; and, V at position Xaa84.

IV. Refined Variable Heavy Chain

The recombinant anti-EpCAM antibody has an immunoglobulin variable heavy chain sequence having the following amino acid sequence:

```
                                         (SEQ ID NO: 6)
Q-X-Q-L-V-Q-S-G-X-E-X-K-K-P-G-E-X-V-K-I-S-C-K-A-S-

G-Y-T-F-T-N-Y-G-M-N-W-V-X-Q-X-P-G-K-G-L-X-W-M-G-W-

I-N-T-Y-T-G-E-P-T-Y-A-D-X-F-X-G-R-X-X-X-S-L-X-T-S-

X-S-T-A-X-L-Q-X-X-X-L-R-X-E-D-X-A-X-Y-F-C-V-R-F-I-

S-K-G-D-Y-W-G-Q-G-T-S-V-T-V-S-S
```

In a preferred embodiment, the recombinant anti-EpCAM antibody has an amino acid sequence defining an immunoglobulin heavy chain FR1, which is represented by residues 1 to 25 of SEQ ID NO: 6, namely Q-X-Q-L-V-Q-S-G-X-E-X-K-K-P-G-E-X-V-K-I-S-C-K-A-S. More preferably, the recombinant anti-EpCAM antibody has at least one of the following amino acids in the FR1 region: I or V at position Xaa2; P or A at position Xaa9; L or V at position Xaa11; and, T or S at position Xaa17. Accordingly, a recombinant anti-EpCAM antibody of the invention has at least one of the following amino acid substitution in the FR1 region: V at position Xaa2; A at position Xaa9; V at position Xaa11; and, S at position Xaa17.

In a preferred embodiment, the recombinant anti-EpCAM antibody has an amino acid sequence defining an immunoglobulin heavy FR1 having at least one of the following amino acids in the FR1 region: I or V at position Xaa2; P or A at position Xaa9; and, L or V at position Xaa11. Accordingly, a recombinant anti-EpCAM antibody of the invention has an amino acid sequence defining an immunoglobulin heavy FR1 having at least one of the following substitutions in the FR1 region: V at position Xaa2; A at position Xaa9; and, V at position Xaa11.

In another embodiment, a recombinant anti-EpCAM antibody of the invention has an amino acid sequence defining an immunoglobulin heavy chain FR2, which is represented by residues 36 to 49 of SEQ ID NO: 6, namely W-V-X-Q-X-P-G-K-G-L-X-W-M-G. More particularly, the recombinant anti-EpCAM antibody has at least one of the following amino acid substitution in the FR2 region: K or R at position Xaa38; T or A at position Xaa40; and, K or E at position Xaa46. More preferably, the recombinant anti-EpCAM antibody has at least one of the following amino acid substitution in the FR2 region: R at position Xaa38; A at position Xaa40; and, E at position Xaa46.

In another preferred embodiment, the recombinant anti-EpCAM antibody has an amino acid sequence defining an immunoglobulin heavy FR2 having the following amino acids in the FR1 region, for example, K or E at position Xaa46. More preferably, the recombinant anti-EpCAM antibody has an amino acid sequence defining an immunoglobulin heavy FR2 having an amino acid substitution in the FR1 region, for example, E at position Xaa46.

In a preferred embodiment, the recombinant anti-EpCAM antibody has an amino acid sequence defining an immunoglobulin heavy chain CDR2, which is represented by residues 50 to 66 of SEQ ID NO: 6, namely W-I-N-T-Y-T-G-E-P-T-Y-A-D-X-F-X-G. More particularly, the recombinant anti-EpCAM antibody has at least one of the following amino acids in the CDR2 region: D or K at position Xaa63; and, K or Q at position Xaa65. More preferably, the recombinant anti-EpCAM antibody has at least one of the following amino acid substitutions in the CDR2 region: K at position Xaa63; and, Q at position Xaa65.

In a preferred embodiment, the recombinant anti-EpCAM antibody has an amino acid sequence defining an immunoglobulin heavy chain FR3, which is represented by residues 67 to 98 of SEQ ID NO: 6, namely R-X-X-X-S-L-X-T-S-X-S-T-A-X-L-Q-X-X-X-L-R-X-E-D-X-A-X-Y-F-C-V-R.

More particularly, the recombinant anti-EpCAM antibody of the invention has at least one of the following amino acids in the FR3 region: F or V at position Xaa68; A or T at position Xaa69; F or I at position Xaa70; E or D at position Xaa73; A or T at position Xaa76; F or Y at position Xaa80; I or L at position Xaa83; N or S at position Xaa84; N or S at position Xaa85; N, A or S at position Xaa88; M or T at position Xaa91; and, T or V at position Xaa93. More preferably, the recombinant anti-EpCAM antibody has at least one of the following amino acid substitutions in the FR3 region: V at position Xaa68; T at position Xaa69; I at position Xaa70; D at position Xaa73; T at position Xaa76; Y at position Xaa80; L at position Xaa83; S at position Xaa84; S at position Xaa85; A or S at position Xaa88; T at position Xaa91; and, V at position Xaa93.

In another preferred embodiment, the recombinant anti-EpCAM antibody of the invention has an amino acid sequence defining an immunoglobulin heavy chain FR3 having at least one of the following amino acids in the FR3 region: F or V at position Xaa68; E or D at position Xaa73; N or S at position Xaa84; N or S at position Xaa85; N or A at position Xaa88; and, T or V at position Xaa93. More preferably, the recombinant anti-EpCAM antibody has an amino acid sequence defining an immunoglobulin heavy FR3 having at least one of the following substitutions in the FR3 region: V at position Xaa68; D at position Xaa73; S at position Xaa84; S at position Xaa85; A at position Xaa88; and, V at position Xaa93.

In a preferred embodiment, the recombinant anti-EpCAM antibody has an amino acid sequence defining an immunoglobulin heavy chain FR4, which is represented by residues 106 to 116 of SEQ ID NO: 6, namely W-G-X-G-T-S-V-T-V-S-S. More particularly, the recombinant anti-EpCAM antibody has at least one of the following amino acids in the FR4 region, for example, Q or T at position Xaa108. More preferably, the recombinant anti-EpCAM antibody has an amino acid substitution in the FR4 region, for example, T at position Xaa108.

Accordingly, preferred V regions contain substitutions in FR domains of $V_H$ and/or VK regions corresponding to murine KS-¼ variable regions. In addition, preferred V regions of the invention do not include insertions or deletions of amino acids relative to the murine KS-¼ variable regions.

Preferred variants include proteins having variable regions with greater than 80% identity/homology murine KS-¼. The amino acid sequence of murine KS variable region or a portion thereof may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to a murine KS variable heavy or light chain FR or CDR.

To determine whether a candidate peptide region has the requisite percentage similarity or identity to a murine KS sequence, the candidate amino acid sequence and murine KS sequence are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *PNAS* 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art. Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

The invention also discloses methods for assaying the expression of KS antibodies from cells such as mammalian cells, insect cells, plant cells, yeast cells, other eukaryotic cells or prokaryotic cells (see Example 1). In a preferred method, KS antibody V regions are expressed as components of an intact human antibody, and the expression of the antibody from a eukaryotic cell line assayed by an ELISA that detects the human Fc region. To precisely quantify binding of a KS antibody to EpCAM, a Biacore assay may be used.

Treatment of Human Disease with KS Antibody Fusion Proteins

The invention also discloses the sequences of KS antibody-IL2 fusion proteins that are useful in treating human disease, such as cancer. Certain KS antibody-IL2 fusion proteins, such as KS-¼-IL2 (see, for example, Construct 3 in Example X), may be used to treat human patients with cancer, with surprisingly little immune response against the antibody.

It is found that, during treatment of human cancers with KS-¼(VH2/VK1)-IL2, even less immunogenicity is seen than with KS-¼(Construct 3)-IL2. Specifically, during a clinical trial, patients with anti-idiotypic antibodies and antibody directed against the antibody-IL2 junction or against the IL-2 moiety are seen at an even lower frequency than with KS-¼(Construct 3)-IL2. Antibody variable regions of the invention can also be fused to other cytokines, for example, interleukins 1, 2, 6, 10, or 12; interferons alpha and beta; TNF, and INF gamma. The invention may be more fully understood by reference to the following non-limiting examples

EXAMPLES

Example 1

Methods and Reagents for Expressing KS Antibodies and Assaying Their Antigen-Binding Activity 1A. Cell Culture and Transfection The following general techniques were used in the subsequent Examples. For transient transfection, plasmid DNA was introduced into human kidney 293 cells by co-precipitation of plasmid DNA with calcium phosphate [Sambrook et al. (1989) *Molecular Cloning: A Laboratory Manual*, Cold Spring Harbor, N.Y.].

In order to obtain stably transfected clones, plasmid DNA was introduced into the mouse myeloma NS/O cells by electroporation. NS/O cells were grown in Dulbecco's modified Eagle's medium supplemented with 10% fetal bovine serum. About $5\times10^6$ cells were washed once with PBS and resuspended in 0.5 ml phosphate buffer solution (PBS). Ten µg of linearized plasmid DNA was then incubated with the cells in a Gene Pulser™ Cuvette (0.4 cm electrode gap, BioRad) for 10 minutes on ice. Electroporation was performed using a Gene Pulser™ (BioRad) with settings at 0.25 V and 500 µF. Cells were allowed to recover for 10 minutes on ice, after which they were resuspended in growth medium and then plated onto two 96-well plates. Stably transfected clones were selected by growth in the presence of 100 nM methotrexate (MTX), which was introduced two days post-transfection. The cells were fed every 3 days for two to three more times, and MTX-resistant clones appeared in 2 to 3 weeks. Supernatants from clones were assayed by anti-human Fc ELISA to identify high producers [Gillies et al. (1989) J. Immunol. Methods 125:191]. High producing clones were isolated and propagated in growth medium containing 100 1 nM MTX.

1B. ELISAs

Three different ELISAs were used to determine the concentrations of protein products in the supernatants of MTX-resistant clones and other test samples. The anti-huFc ELISA was used to measure the amount of human Fc-containing proteins, e.g., chimeric antibodies. The anti-hu kappa ELISA was used to measure the amount of kappa light chain (of chimeric or human immunoglobulins). The anti-muFc ELISA was used to measure the amount of muFc-containing proteins in test samples (see Example 1C below).

The anti-huFc ELISA is described in detail below.

A. Coating Plates

ELISA plates were coated with AffiniPure goat anti-human IgG (H+L) (Jackson Immuno Research) at 5 µg/ml in PBS, and 100 µl/well in 96-well plates (Nunc-Immuno plate Maxisorp). Coated plates were covered and incubated at 4° C. overnight. Plates were then washed 4 times with 0.05% Tween™ (Tween™ 20) in PBS, and blocked with 1% BSA/1% goat senlm in PBS, 200 µl/well. After incubation with the blocking buffer at 37° C. for 2 hours, the plates were washed 4 times with 0.05% Tween™ in PBS and tapped dry on paper towels.

B. Incubation with Test Samples and Secondary Antibody

Test samples were diluted to the proper concentrations in sample buffer, which contained 1% BSA/1% goat serum/0.05% Tween™ in PBS. A standard curve was prepared with a chimeric antibody (with a human Fc), the concentration of which was known. To prepare a standard curve, serial dilutions are made in the sample buffer to give a standard curve ranging from 125 ng/ml to 3.9 ng/ml. The diluted samples and standards were added to the plate, 100 µd/well, and the plate incubated at 37° C. for 2 hours.

After incubation, the plate was washed 8 times with 0.05% Tween™ in PBS. To each well was then added 100 µl of the secondary antibody, the horse radish peroxidase (HRP)-conjugated anti-human IgG (Jackson Immuno Research), diluted around 1:120,000 in the sample buffer. The exact dilution of the secondary antibody had to be determined for each lot of the HRP-conjugated anti-human IgG. After incubation at 37° C. for 2 hours, the plate was washed 8 times with 0.05% Tween™ in PBS.

C. Development

The substrate solution was added to the plate at 100 µl/well. The substrate solution was prepared by dissolving 30 mg of o-phenylenediamine dihydrochloride (OPD) (1 tablet) into 15 ml of 0.025 M citric acid/0.05M $Na_2HPO_4$ buffer, pH 5, which contained 0.03% of freshly added $H_2O_2$. The color was allowed to develop for 30 minutes at room temperature in the dark. The developing time was subject to change, depending on lot to lot variability of the coated plates, the secondary antibody, etc. The color development in the standard curve was observed to determine when to stop the reaction. The reaction was stopped by adding 4N $H_2SO_4$, 100 µl/well. The plate was read by a plate reader, which was set at both 490 nm and 650 nm and programmed to subtract off the background OD at 650 nm from the OD at 490 nm.

The anti-hu kappa ELISA followed the same procedure as described above, except that the secondary antibody used was horse radish peroxidase-conjugated goat anti-hu kappa (Southern Biotechnology Assoc. Inc., Birmingham, Ala.), used at 1:4000 dilution.

The procedure for the anti-muFc ELISA was also similar, except that ELISA plates were coated with AffiniPure goat anti-murine IgG (H+L) (Jackson Immuno Research) at 5 µg/ml in PBS, and 100 µl/well; and the secondary antibody was horse radish peroxidase-conjugated goat anti-muIgG, Fcγ (Jackson ImmunoResearch), used at 1:5000 dilution.

1C. Cloning of the KS Antigen (KSA, EpCAM) and Expression of the Soluble Form as Human EpCAM-Murine Fc Messenger RNA (MRNA) was prepared from LnCAP cells using Dynabeads™ mRNA Direct Kit (Dynal, Inc., Lake Success, N.Y.) according to the manufacturer's instructions. After first strand CDNA synthesis with oligo(dT)) and reverse transcriptase, full length CDNA encoding epithelial cell adhesion molecule (also known as KS antigen or KSA), was cloned by polymerase chain reaction (PCR). The sequences of the PCR primers were based on the published sequence described in Perez and Walker (1989) J. Immunol. 142:3662-3667. The sequence of the sense primer is TCTA-GAGCAGCATGGCGCCCCCGCA (SEQ ID NO: 27), and the sequence of the nonsense prime: is CTCGAGTTATG-CATTGAGTTCCCT (SEQ ID NO: 28), where the translation initiation codon and the anti-codon of the translation stop codon are denoted in bold, and the restriction sites XbaI (TCTAGA) and XhoI (CTCGAG) are underlined. The PCR product was cloned and the correct KSA sequence was confirmed by sequencing several independent clones. The CDNA sequence of the KSA from LnCAP was essentially identical to the published sequence of KSA from UCLA-P3 cells (Perez and Walker, 1989). However, at amino acid residue number 115, the nucleotide sequence from LnCAP was ATG rather than ACG (Met instead of Thr, and at amino acid residue number 277, the nucleotide sequence from LnCAP was ATA rather than ATG (Ile instead of Met).

Binding of KS-¼ antibody to recombinant KSA was demonstrated by immunostaining. Surface expression of KSA was obtained by transfecting cells, e.g., CT26, B16, etc., with full length KSA in a suitable mammalian expression vector (pdCs, as described in U.S. Pat. No. 5,541,087), followed by immunostaining with the KS-¼ antibody. For the expression of KSA as a soluble antigen, the portion of the cDNA encoding the transmembrane domain of the KSA was deleted. To facilitate expression, detection, and purification, the soluble KSA was expressed as a KSA-muFc, the construction of which is described as follows. The 780 bp XbaI-EcoRI restriction fragment encoding the soluble KSA was ligated to the AflII-XhoI fragment encoding the muFc (U.S. Pat. No. 5,726,044) via a linker-adaptor:

```
                                             (SEQ ID NO: 29)
    5'  AA TTC TCA ATG CAG GGC          3'

(SEQ ID NO: 30)
    3'          G AGT TAC GTC CCG AAT T 5'
```

The XbaI-XhoI fragment encoding soluble KSA-muFc was ligated to the pdCs vector. The resultant expression vector, pdCs-KSA-muFc, was used to transfect cells and stable clones expressing KSA-muFc were identified by anti-muFc ELISA.

1D. Measurement of Antigen Binding

KSA-muFc in conditioned medium was first purified by Protein A chromatography according to supplier's protocol (Repligen, Cambridge, Mass.). Purified KSA-muFc was used to coat 96-well plates (Nunc-Immuno plate, Maxisorp) at 5 µg/ml in PBS, and 100 µl/well. The assay was similar to the ELISA procedure described in Example 1B. Briefly, coated plates were covered and incubated at 4° C. overnight. Plates then were washed and blocked. Test samples were diluted to the proper concentrations in the sample buffer, added to the plate at 100 µl/well, and the plate was incubated at 37° C. for 1 hour. After incubation, the plate was washed 8 times with 0.05% Tween in PBS. To each well was then added 100 µl of the secondary antibody, the horse radish peroxidase-conjugated anti-human IgG (Jackson Immuno Research), diluted around 1:120,000 in the sample buffer. The plate was then developed and read as described in Example 1B.

1E. Measurement of On-Rates and Off-Rates of KS-1/4 Antibodies from EpCAM using a Biacore Assay.

The affinity of KS-1/4 and KS-IL2 molecules for the antigen EpCAM were measured by surface plasmon resonance analysis of the antibody-antigen interaction, using a Biacore™ machine (Biacore International AR, Uppsala, Sweden). EpCAM-murineFc was coupled to a CM5 sensor chip using an nmine coupling protocol supplied by the manufacturer. KS-1/4 and KS-IL2 at concentrations varying between 25 nm and 200 nM were then passed over the chip, whereby binding to the chip was observed. Using the built-in curve-fitting routines of the Biacore™ software, the on-rate, off-rate, association and dissociation constants were calculated.

1F. Measurement of Binding Affinities of KS-1/4 Antibodies Using Cell Lines Expressing EpCAM Purified KS-1/4 antibodies were iodinated with $^{125}$I using standard techniques, and increasing concentrations of labeled protein were incubated with the EpCAM-positive cell line PC-3. Saturation binding curves were generated and the dissociation constants were determined by Scatchard analysis.

Example 2

Cloning of cDNAs Encoding $V_H$ and $V_K$ of Mouse KS-1/4 and Construction of Vector for the Expression of KS-1/4 Hybridoma-Derived Antibody Messenger RNA prepared from the mouse KS-1/4-expressing hybridoma (obtained from R. Reisfeld, Scripps Research Institute) was reverse transcribed with oligo(dT) and then used as templates for PCR to amplify the sequences encoding the variable region of the heavy chain ($V_H$) and the variable region of the light chain ($V_K$). The PCR primers were designed based on published sequences (Beavers et al., ibid.). The PCR primers for $V_H$ had the following sequences:

```
                                              (SEQ ID NO: 31)
V_H forward primer (5') GACTCGAGCCCAAGTCTTAGACATC
(3')
                                              (SEQ ID NO: 32)
V_H reverse primer (5') CAAGCTTACCTGAGGAGACGGTGACTG
ACGTTC (3'),
``` where the CTCGAG and AAGCTT sequences represent the XhoI and HindIII restriction sites, respectively, used for ligating the $V_H$ into the expression vector (see below); and the TAC in the reverse primer would introduce GTA, the splice donor consensus sequence, in the sense strand of the PCR product.

The PCR primers for $V_K$ had the following sequences:

```
                                              (SEQ ID NO: 33)
V_K forward primer (5') GATCTAGACAAGATGGATTTTCAAGTG
(3')
                                              (SEQ ID NO: 34)
V_K reverse primer (5') GAAGATCTTACGTTTTATTTCCAGCTT
GG (3')
``` where the TCTAGA and AGATCT sequences represent the XbaI and BglII restriction sites, respectively, used for ligating the $V_K$ into the expression vector (see below); ATG is the translation initiation codon of the light chain; and the TAC in the reverse primer would introduce GTA, the splice donor consensus sequence, in the sense strand of the PCR product.

The PCR products encoding the $V_H$ and $V_K$ of the mouse KS-1/4 antibody were cloned into pCRII vector (Invitrogen, Carlsbad, Calif.). Several $V_H$ and $V_K$ clones were sequenced and the consensus sequence of each determined. The $V_H$ and $V_K$ sequences were inserted in a stepwise fashion into the expression vector pdHL7. The ligations took advantage of the unique XhoI and HindIII sites for the $V_H$, and the unique XbaI and BglII/BamHI sites for the $V_K$ (the unique BglII in the $V_K$ insert and the unique BamHI in the vector have compatible overhangs). The resultant construct is called pdHL7-hybridoma chKS-1/4, which already contained transcription regulatory elements and human Ig constant region sequences for the expression of chimeric antibodies (Gillies et al. (1989) J. Immunol. Methods 125:191).

The expression vector pdHL7 was derived from pdHL2 [Gillies et al. (1991) Hybridoma 10:347-356], with the following modifications: in the expression vector pdHL2, the transcriptional units for the light chain and the heavy chain-cytokine consisted of the enhancer of the heavy chain immunoglobulin gene and the metallothionein promoter. In pdHL7, these two transcriptional units consisted of the CMV enhancer-promoter [Boshart et al. (1985) Cell 41:521-530]. The DNA encoding the CMV enhancer-promoter was derived from the AflIII-HindIII fragment of the commercially available pcDNAI (Invitrogen Corp., San Diego, Calif.).

Example 3

Expression Studies of Murine KS-1/4 Antibodies

This example discusses expression studies performed using an antibody expression plasmid encoding the V region sequences disclosed in U.S. Pat. No. 4,975,369.

3A. Plasmid Construction

To directly compare the chimeric antibodies encoded by the Hybridoma KS-1/4 sequence and those sequences described in U.S. Pat. No. 4,975,369, the cDNA encoding the VH sequence described in U.S. Pat. No. 4,975,369 was synthesized. This was then ligated into the pdHL7 expression vector already containing the $V_K$ of KS-¼.

In order to construct the $V_H$ sequence described in U.S. Pat. No. 4,975,369, an NdeI-HindIII fragment encoding part of the $V_H$ sequence was obtained by total chemical synthesis. Overlapping oligonucleotides were chemically synthesized and ligated. The ligated duplex was then subcloned into a XbaI-HindIII pBluescript vector (Stratagene, LaJolla, Calif.).

This DNA encodes the protein sequence IQQPQNMRTM (residues 83-92 of SEQ ID NO:35) of U.S. Pat. No. 4,975,369. Immediately 3' to the coding sequence is the splice donor site beginning with gta. The ctag at the 5' end of the top strand is the overhang for the XbaI cloning site. The XbaI site was created only for cloning into the polylinker of the pBluescript vector. It was followed immediately by the NdeI restriction site (CATATG). The agct at the 5' end of the bottom strand is the overhang of the HindIII cloning site. This HindIII sticky end is later ligated to the HindIII site in the intron preceding the Cγ1 gene [Gillies et al. (1991) Hybridoma 10:347-356].

After sequence verification, the NdeI-HindIII restriction fragment was isolated. This, together with the XhoI-NdeI fragment encoding the N-terminal half of $V_H$, was then ligated to the XhoI-HindIII digested pdHL7 expression vector containing the $V_K$ of KS-¼. The resultant construct, pdHL7-'369 chKS-¼, contained the $V_K$ and $V_H$ described in U.S. Pat. No. 4,975,369 (referred to as U.S. Pat. No. 4,975,369 chKS-¼).

3B. Comparison of Hybridoma chKS-¼ and U.S. Pat. No. 4,975,369 chKS-¼ Antibodies The plasmid DNAs pdHL7-hybridoma chKS-¼ and pdHL7-'369 chKS-¼ were introduced in parallel into human kidney 293 cells by the calcium phosphate coprecipitation procedure mentioned above. Five days post-transfection, the conditioned media were assayed by anti-huFc ELISA and kappa ELISA (see Example 1 for ELISA procedures) and the results are summmarized in Table 1.

TABLE 1

| Antibody | huFc ELISA | Kappa ELISA |
|---|---|---|
| Hybridoma chKS-1/4 | 254 ng/mL | 200 ng/mL |
| U.S. Pat. No. 4,975,369 chKS-1/4 | 14 ng/mL | 0 ng/mL |

The results indicated that hybridoma chKS-¼ was expressed and secreted normally, and that the secreted antibody consisted of roughly equimolar amounts of heavy and light chains, within the accuracies of the two different ELISAs. On the other hand, only a low level of heavy chain was detected in the conditioned medium for the U.S. Pat. No. 4,975,369 chKS-¼ antibody, and no kappa light chain was associated with it.

Western blot analysis was performed on the total cell lysates and the conditioned media of the two transiently transfected cell lines. The procedures for Western blot analysis were as described in (Sambrook et al. (1989), supra). In order to analyze the total cell lysates, the transfected cells were lysed, centrifuged to remove the debris, and the lysate from the equivalent of $5 \times 10^5$ cells applied per lane. To analyze the conditioned media, the protein product from 300 μL of the conditioned medium was first purified by Protein A Sepharose chromatography prior to SDS-PAGE under reducing conditions. After Western blot transfer, the blot was hybridized with a horseradish peroxidase-conjugated goat anti-human IgG, Fcγ (Jackson ImmunoResearch), used at 1:2000 dilution.

The Western blot transfer showed that under the conditions used, the heavy chain was detected in both the conditioned media and the lysed cells of the transfection with pdHL7-hybridoma chKS-¼. This result indicates that the heavy chain of the chKS-¼ antibody was produced in the cells and secreted efficiently (together with the light chain). On the other hand, the heavy chain from the transfection with pdHL7-'369 chKS-¼ was detected only in the cell lysate but not in the conditioned media. This result indicated that although a comparable level of heavy chain was produced inside the cell, it was not secreted. This finding was consistent with the ELISA data, which showed that there was no kappa light chain associated with the small amount of secreted heavy chain in the U.S. Pat. No. 4,975,369 chKS-¼ antibody. It is understood that immunoglobulin heavy chains typically are not normally secreted in the absence of immunoglobulin light chains [Hendershot et al. (1987) Immunology Today 8:111].

In addition to the foregoing, NS/0 cells were transfected by electroporation with the plasmids pdHL7-Hybridoma chKS-¼ and pdHL7-U.S. Pat. No. 4,975,369 chKS-¼ in parallel. Stable clones were selected in the presence of 100 nM MTX, as described in Example 1, and the conditioned media of the MTX-resistant clones in 96-well plates was assayed by anti-huFc ELISA, as described in Example 1. The results are summarized in Table 2.

TABLE 2

| Antibody | Total number of clones screened | Mode* | Highest level of expression* |
|---|---|---|---|
| Hybridoma chKS-1/4 | 80 | 0.1-0.5 μg/mL (41) | 10-50 μg/mL (4) |
| U.S. Pat. No. 4,975,369 chKS-1/4 | 47 | 0-10 ng/mL (36) | 0.1-0.4 μg/mL (4) |

(*The numbers in parentheses denote the number of clones in the mode or the number expressing the highest levels of product, as determined by anti-Fc ELISA.)

When screened at the 96-well stage, the majority of the clones obtained with the pdHL7-hybridoma chKS-¼ construct produced about 100 ng/mL to 500 ng/mL of antibody, with the best clones producing about 10-50 μg/mL. On the other hand, the majority of the clones obtained with the pdHL7-'369 chKS-¼ construct produced about 0 ng/mL to 10 ng/mL of antibody, with the best producing about 300-400 ng/mL. To examine the composition and binding properties of the U.S. Pat. No. 4,975,369 chKS-¼ antibody, it was necessary to grow up the clones that produced at 300-400 ng/mL. Two of these clones were chosen for expansion. However, their expression levels were found to be very unstable. By the time the cultures were grown up to 200 mL, the expression levels of both clones had dropped to about 20 ng/mL, as assayed by anti-Fc ELISA. When the same conditioned media were assayed by the anti-kappa ELISA, no kappa light chain was detected, as was the case in transient expression in 293 cells.

The following experiment indicated that no detectable kappa light chain was associated with the U.S. Pat. No. 4,975,369 chKS-¼ heavy chain. Briefly, 50 mL each of the conditioned media from each of the clones was concentrated by Protein A chromatography. The eluate were assayed by anti- Fc ELISA and anti-kappa ELISA. As a control, conditioned medium from a hybridoma chKS-¼-producing clone was treated the same way and assayed at the same time. The ELISA results are summarized in Table 3.

TABLE 3

| Antibody | huFc ELISA | Kappa ELISA |
| --- | --- | --- |
| Hybridoma chKS-1/4 | 42 µg/mL | 44 µg/mL |
| U.S. Pat. No. 4,975,369 chKS-1/4-clone 1 | 253 ng/mL | 0 ng/mL |
| U.S. Pat. No. 4,975,369 chKS-1/4-clone 21 | 313 ng/mL | 0 ng/mL |

The results showed that there was indeed no detectable kappa light chain associated with the U.S. Pat. No. 4,975,369 chKS-¼ heavy chain. Furthermore, the hybridoma chKS-¼ antibody was shown to bind KS antigen at 10-20 ng/mL, whereas the U.S. Pat. No. 4,975,369 antibody from both clones and concentrated to 253 and 313 ng/mL, still did not bind KS antigen (see Example 9 for measurement of binding to KS antigen.)

Example 4

Expression and Characterization of Variant KS Antibodies

Mutations that significantly lower the expression or the affinity of an antibody for a target molecule are expected to be less effective for therapeutic purposes in humans. Some approaches to reducing immunogenicity, such as "veneering," "humanization," and "deimmunization" involve the introduction of many amino acid substitutions, and may disrupt binding of an antibody to an antigen (see, e.g., U.S. Pat. Nos. 5,639,641; and 5,585,089; and PCT Publication Nos. WO 98/52976; WO 00/34317). There is a need in the art for classes of antibody sequences that will bind to epithelial cell adhesion molecule, but which are distinct from the original mouse monoclonal antibodies that recognize this antigen.

Various combinations of KS-¼ heavy and light chain variable ("V") regions were tested for their ability to be expressed, and for their ability to bind to EpCAM. These results are summarized in Tables 4-6 and described below.

TABLE 4

Sequences of KS-1/4 antibody heavy and light chain V regions.

Light chains:

```
                 10        20        30        40        50        60
                  |         |         |         |         |         |
    VK0    QILLTQSPAIMSASPGEKVTMTCSASSSVSYMLWYQQKPGSSPKPWIFDTSNLASGFPAR
    VK1    QIVLTQSPASLAVSPGQRATITCSASSSVSYILWYQQKPGQPPKPWIFDTSNLASGFPSR
    VK6    EIVLTQSPATLSLSPGERVTLTCSASSSVSYMLWYQQKPGQAPKLLIFDTSNLASGIPAR
    VK7    QILLTQSPAIMSASPGERVTMTCSASSSVSYMLWYQQKPGSSPKPWIFDTSNLASGFPAR
    VK8    EIVLTQSPATLSLSPGERVTLTCSASSSVSYMLWYQQKPGSSPKPWIFDTSNLASGFPAR 70        80        90       100
                  |         |         |         |
    VK0    FSGSGSGTSYSLIISSMEAEDAATYYCHQRSGYPYTFGGGTKLEIK    (SEQ ID NO: 1)
    VK1    FSGSGSGTSYTLTINSLEAEDAATYYCHQRSGYPYTFGGGTKVEIK    (SEQ ID NO: 11)
    VK6    FSGSGSGTDYTLTISSLEPEDFAVYYCHQRSGYPYTFGGGTKLEIK    (SEQ ID NO: 7)
    VK7    FSGSGSGTSYSLIISSMEPEDAATYYCHQRSGYPYTFGGGTKLEIK    (SEQ ID NO: 8)
    VK8    FSGSGSGTSYSLIISSMEAEDAATYYCHQRSGYPYTFGGGTKLEIK    (SEQ ID NO: 9)
```

Heavy chains:

```
                 10        20        30        40        50        60
                  |         |         |         |         |         |
    VH0    QIQLVQSGPELKKPGETVKISCKASGYTFTNYGMNWVKQTPGKGLKWMGWINTYTGEPTY
    VH1    QIQLVQSGPELKKPGSSVKISCKASGYTFTNYGMNWVRQAPGKGLKWMGWINTYTGEPTY
    VH2    QIQLVQSGPELKKPGSSVKISCKASGYTFTNYGMNWVRQAPGKGLKWMGWINTYTGEPTY
    VH2.5  QIQLVQSGPELKKPGSSVKISCKASGYTFTNYGMNWVRQAPGKGLKWMGWINTYTGEPTY
    VH6    QVQLVQSGAEVKKPGESVKISCKASGYTFTNYGMNWVRQAPGKGLEWMGWINTYTGEPTY
    VH7    QIQLVQSGAEVKKPGETVKISCKASGYTFTNYGMNWVKQTPGKGLKWMGWINTYTGEPTY
    VH369  QIQLVQSGPELKKPGETVKISCKASGYTFTNYGMNWVKQTPGKGLKWMGWINTYTGEPTY 70        80        90       100       110
                  |         |         |         |         |
    VH0    ADDFKGRFAFSLETSASTAFLQINNLRNE.DMATYFCVRFISKGDYWGQGTSVTVSS   (SEQ ID NO: 2)
    VH1    ADDFKGRFTITAETSTSTLYLQLNNLRSE.DTATYFCVRFMSKGDYWGQGTTVTVSS   (SEQ ID NO: 21)
    VH2    ADDFKGRFTITAETSTSTLYLQLNNLRSE.DTATYFCVRFISKGDYWGQGTTVTVSS   (SEQ ID NO: 22)
    VH2.5  ADDFKGRFTITAETSTSTLYLQLNNLRSE.DTATYFCVRFISKGDYWGTGTTVTVSS   (SEQ ID NO: 19)
    VH6    AQKFQGRVTISLDTSTSTAYLQLSSLRAE.DTAVYFCVRFISKGDYWGQGTSVTVSS   (SEQ ID NO: 17)
    VH7    ADDFKGRFAFSLETSTSTAFLQINNLRSE.DTATYFCVRFISKGDYWGQGTSVTVSS   (SEQ ID NO: 18)
    VH369  ADDFKGRFAFSLETSASTAFLQIqqpqnmrtMATYFCVRFISKGDYWGQGTSVTVSS   (SEQ ID NO: 35)
```

TABLE 5

Sequences of KS-1/4 antibody variants and CDR3 heavy chain variants with single amino acid insertions.

| | | |
|---|---|---|
| VH2 partial seq.: 92-109 of SEQ ID NO: 22) | . . . ATYFCVRF I S K GDYWGQG. . . | (amino acid residues |
| VH2.1: | . . . ATYFCVRF IIS K GDYWGQG. . . | (SEQ ID NO: 36) |
| VH2.2: | . . . ATYFCVRF IVS K GDYWGQG. . . | (SEQ ID NO: 37) |
| VH2.3: | . . . ATYFCVRF I SAK GDYWGQG. . . | (SEQ ID NO: 38) |
| VH2.4: | . . . ATYFCVRF I S KTGDYWGQG. . . | (SEQ ID NO: 39) |

TABLE 6

Expression levels and binding activity of variant KS-1/4 antibodies.

| | Expression | | EpCAM affinity | |
|---|---|---|---|---|
| Contruct | Transient (*) (in ng/mL) | Stable (*) (in µg/mL) | Relative binding (**) | Kd (nM) |
| Group 1 | | | | |
| VK0/VH0 (Hybridoma chKS-1/4) | | 10-50 | 1x | $1.0 \times 10^{-9}$ |
| VK0/VH'369 ('369 chKS-1/4) | | 0.1-0.4 (***) | >>30x | |
| VK8/VH7 (Construct 3) | | 10-50 | | $1.0 \times 10^{-9}$ |
| VK6/VH6 (Construct 1) | 300 | | n.d. | |
| VK7/VH7 (Construct 2) | 30 | | | |
| VK8/VH7-IL2 | | 10-50 | | $1.0 \times 10^{-9}$ |
| VK1/VH1-IL2 | | 10-50 | | $7.9 \times 10^{-9}$ |
| VK1/VH2-IL2 | | 10-50 | | $3.1 \times 10^{-9}$ |
| Group 2 | | | | |
| VK8/VH7 (Construct 3; control) | 1500 | | 1x | |
| VK0/VH1 | 1500 | | 8x | |
| VK1/VH7 | 1500 | | 1x | |
| VK1/VH1 | 1500 | | 2x | |
| VK1/VH2 | 1500 | | 1x-2x | |
| VK1/VH1-IL2 | 1500 | | 5x | |
| VK1/VH2-IL2 | 1500 | | 1.5x | |
| VK1/VH2.5-IL2 | 1500 | | 3x-4x | |
| Group 3 | | | | |
| VK8/VH7-IL2 (control) | 760 | | 1x | |
| VK1/VH1-IL2 | 350 | | 2x | |
| VK1/VH2.1-IL2 | 290 | | >10x | |
| VK1/VH2.2-IL2 | 270 | | >10x | |
| VK1/VH2.3-IL2 | 190 | | 7x | |
| VK1/VH2.4-IL2 | 210 | | 3x | |

(*) Routinely achievable levels.
(**) "Relative Binding" is expressed as the fold-increase in protein concentration required to reach an equivalent level of binding. Thus, a larger number reflects a lower affinity for EpCAM.
(***) Kappa light chain was not detectable by ELISA (equivalent to background); therefore, functional antibodies were not expressed.
(**) n.d. = not detectable
In Group 2 and Group 3, the relative binding activity of each protein was normalized to the control shown in the first line for that group. The ELISA assay is primarily a reflection of off-rates, based on amount of protein bound after several rounds of washes. It is used as a rapid screen to rule out poor binders, but is not a precise measure of affinity. In Group 3, VH2 variants VH2.1-VH2.4 were compared with VH1 to determine if amino acid insertions might result in improved relative binding.

The sequences are related as follows. As described in the examples, the VH0 and VK0 sequences were derived from PCR amplification from a hybridoma cell line that expresses the original mouse-derived KS-1/4 (SEQ ID NO: 1 and SEQ ID NO: 2). VH-'369 is the VH sequence disclosed in U.S. Pat. No. 4,975,369. Sequences VH1, VH2, VH2.1-2.4 VK1, and VK2 were derived either using deimmunization technology where potential T cell epitopes are eliminated or weakened by introduction of mutations that reduce binding of a peptide epitope to an MHC Class II molecule, or by changing non-human T cell epitopes so that they correspond to human self-epitopes that are present in human antibodies. The design of these constructs is further described and analyzed below. Constructs of Table 6 were generated by transfecting mammalian cells with combinations of nucleic acids that expressed the corresponding heavy and light chain V regions. Sequences VH6, VH7, VK6, VK7, and VK8 were generated by changing surface residues of the hybridoma KS-¼ to human counterparts as described below, with the purpose of removing potential human B cell epitopes. Constructs 1 through 3 were generated by transfecting mammalian cells with combinations of nucleic acids that expressed heavy and light chain V regions VH6, VH7, VK6, VK7, and VK8 as described in Table 4 and below.

4A. Characterization of KS Antibodies with Fewer Human T Cell Epitopes

Sequences VH2.1-VH2.5 were made to test whether certain amino acid insertions and substitutions in the region of the KS-1/4 heavy chain CDR3 could be tolerated. Expression vectors for the light and heavy chain combinations VK0/VH1, VK1/VH7, VK1/VH1, VK1/VH2, VK1/VH1-IL2, VK1/VH2-IL2, and VK1/VH2.5-IL2 were constructed and the corresponding antibodies and antibody-IL2 fusion proteins expressed and tested according to methods described in the preceding examples.

Specifically, sequences VH1, VH2, VK1, and VK2 were obtained by total chemical synthesis. For each of these sequences, a series of overlapping oligonucleotides that span the entire coding and complementary strands of these regions were chemically synthesized, phosphorylated, and ligated. The ligated duplex molecules were then amplified by PCR with appropriate primers to the fragment ends, introduced into pCRII vector (Invitrogen, Carlsbad, Calif.) and the sequences verified. These DNA fragments were then introduced into the expression vector pdHL7 at appropriate sites to generate the complete heavy ("H") chain and light ("L") chain, respectively.

Sequence VH2.5 was derived from VH2 by the modification of a single codon to obtain a Thr rather than a Gln at position 108 (Table 4), using standard molecular biology techniques.

The antibodies were tested by ELISA (Table 6) and using surface plasmon resonance (Biacore™ machine and software) to compare their ability to bind to EpCAM. Results of the ELISA experiments were considered to reflect primarily off-rate and not on-rate, and to be generally less precise, such that a poor ELISA result was generally used to exclude certain constructs from further consideration. However, antibodies that showed good binding by the ELISA test needed to be characterized further.

Results of the surface plasmon resonance analysis were as follows:

| Fusion Protein | $k_{on}$ (M$^{-1}$ s$^{-1}$) | $k_{off}$ (s$^{-1}$) | $K_D$ (M) |
|---|---|---|---|
| VK8/VH7-IL2 | $3.1 \times 10^5$ | $3.2 \times 10^{-4}$ | $1.0 \times 10^{-9}$ |
| VK1/VH2-IL2 | $1.7 \times 10^5$ | $5.3 \times 10^{-4}$ | $3.1 \times 10^{-9}$ |
| VK1/VH1-IL2 | $2.8 \times 10^5$ | $2.2 \times 10^{-3}$ | $7.9 \times 10^{-9}$ |

Because the off-rate of VK1/VH1-IL2 was much faster than for VK1/V2-IL2 or VK8/VH7-IL2, VK1/VH1-IL2 was considered to be a less useful fusion protein.

Considering that VK1/VH1-IL2 and VK1/VH1-IL2 differ only by the methionine/isoleucine difference at $V_H$ position 100 in CDR3, the enhanced off-rate of VK1/VH1-IL2 compared to VK1/VH2-IL2 suggests that this position makes a hydrophobic contact with EpCAM, and that the slightly longer methionine side-chain makes a less effective contact. In the field of protein-protein interactions, it is generally thought that hydrophobic interactions play a major role in determining off-rates but a much less significant role in determining on-rates.

4B. Characterization of KS-1/4 Variants with Single Amino Acid Insertions

The importance of the CDR3 sequence in the heavy chain V region for the affinity of the KS antibody to EpCAM was determined with a series of variants that contained an amino acid insertion or substitution in this region. Sequences VH2.1, VH2.2, VH2.3, and VH2.4 were generated by manipulation of an expression vector encoding VH2 and VK1 using standard recombinant DNA techniques. The resulting expression vectors were transfected into NS/0 cells and secreted antibody proteins purified as described in preceding examples.

It was found that the VH1 variant was suboptimal compared to the VH2 variant, indicating that the isoleucine in CDR3 could not be substituted with methionine. The next goal was to test whether insertion of an amino acid in CDR3 could yield a KS-1/4 heavy chain V region with better binding characteristics than VH1. The data in Table 6 compare the binding of VK1/VH2.1, VK1/VH2.2, VK1/VH2.3, and VK1/VH2.4, with VK1/VH1. It was found that none of the constructs with an amino acid insertion in the KS-1/4 $V_H$ CDR3 showed improved antigen binding compared to VH1, rather, antigen binding activity of the insertion mutants was either somewhat decreased or profoundly decreased.

These results indicate that insertion of amino acids in CDR3 generally is deleterious to the antigen binding activity of KS-1/4 heavy chain V regions. When this data is analyzed, some general conclusions emerge. Specifically, the segment of KS-1/4 $V_H$ amino acid at positions 84 to 108, consisting of the amino acids Asn-Asn-Leu-Arg-Asn-Glu-Asp-Met-Ala-Thr-Tyr-Phe-Cys-Val-Arg-Phe-Ile-Ser-Lys-Gly-Asp-Tyr-Trp-Gly-Gln (residues 84 to 108 of SEQ ID NO:2), is important for KS-1/4 antigen binding. This segment includes a framework segment, Asn-Asn-Leu-Arg-Asn-Glu-Asp-Met-Ala-Thr-Tyr-Phe-Cys-Val-Arg (residues 84-98 of SEQ ID NO :2), which is generally tolerant to single and multiple amino acid substitutions, but not tolerant to amino acid insertions, which may have a deleterious effect on expression and assembly. In addition, the data suggests that for the amino acids at positions 86, 91, 93, 94, and 95, it is preferable to have hydrophobic amino acids for an antibody that is efficiently expressed and binds to EpCAM.

Insertion of an amino acid in the V.sub.H CDR3 segment, consisting of Phe-Ile-Ser-Lys-Gly-Asp-Tyr (residues 99-105 of SEQ ID NO:2), is generally deleterious to the EpCAM antigen-binding function of a KS-1/4 antibody, although some insertions can be tolerated with only partial loss of activity. Similarly, substitution of these positions is also generally deleterious to binding of the EpCAM antigen, although some insertions can be tolerated with only partial loss of activity.

4C. Construction of Active Derivatives of KS-1/4 Antibodies with Mouse Surface Residues Converted to Their Human Counterparts Antibodies were prepared by substituting amino acids within the KS-1/4 antibody with amino acids commonly found in human antibodies in order to minimize the immunogenicity of the mouse-derived V regions. Preferred KS derivatives also retained specific binding affinity for human EpCAM.

Construct 1. It was found that the KS-1/4 light chain most closely resembled human consensus subgroup III, and the heavy chain most closely resembled subgroup I. Based on these similarities, a conceptual sequence consisting of the human consensus subgroup amino acids and KS-1/4-derived CDRs and non-consensus amino acids was generated. For this and the following constructs a three-dimensional model was generated using a Silicon Graphics™ Workstation and Biosym molecular modeling software.

Inspection of the three-dimensional model revealed that certain human-derived amino acids were close to the CDRs and were likely to influence their conformation. Based on this analysis, in the light chain, human Ser22, Arg44, and Phe66 were changed back to Thr, Lys, and Tyr, respectively. In the heavy chain, it was believed such changes were unnecessary. In the final design for Construct 1, the light chain had 18 human amino acids not found in the mouse light chain, and the heavy chain had 22 human amino acids not found in the mouse heavy chain.

DNAs for expression of Construct 1 were created using synthetic oligonucleotides. The Construct 1 protein was efficiently expressed but was found to be more than 10-fold less active in an EpCAM binding assay.

Construct 2. A less aggressive approach was then taken, by which only the following changes were introduced:

Light chain: K18R, A79P

Heavy chain: P9A, L11V, A76T, N88S, M91T

DNAs for expression of Construct 2 were created using synthetic oligonucleotides and standard recombinant DNA techniques. The Construct 2 protein was not efficiently expressed. It was further found that the combination of Construct 2 light chain and mouse KS-¼ heavy chain was not efficiently expressed, while the combination of Construct 2 heavy chain and mouse KS-¼ light chain was efficiently expressed. Thus, the expression defect appeared to lie in the Construct 2 light chain.

Construct 3. Based on the apparent expression defect in the Construct 2 light chain, a new light chain was constructed by fusing the N-terminal portion of the light chain of Construct 1 with the C-terminal portion of the mouse light chain. The KpnI site, which encodes the amino acids at positions 35 and 36, was used. When this light chain was combined with the Construct 2 heavy chain, efficient expression and no significant loss of binding was observed.

Because Construct 3 resulted in an antibody with superior properties in terms of protein expression and affinity for the antigen when compared to Construct 1 or 2, DNA sequences of Construct 3 were inserted into pdHL7s-IL2, resulting in pdHL7s-VK8/VH7-IL2, which is disclosed as SEQ ID NO: 40. For expression purposes, this plasmid DNA was electroporated into mouse myeloma cells NS/0 to produce a stably transfected cell line as described in Example 1A. Culture medium taken from stable clones was then assayed for antibody expression in an ELISA coated with human Fc, as described in Example 1B. The amino acid sequences of the heavy and light chain for this antibody fusion protein are shown in SEQ ID NO: 41 and SEQ ID NO: 42, respectively.

In addition, the binding of iodinated VK8/VH7 and VK8/VH7-IL2 to EpCAM expressed on the surface of PC-3 tumor cells was compared to binding of iodinated VK0/VH0-IL2, using methods described in Example 1F. Within experimental error, essentially identical binding affinities were found for VK8/VH7 and VK0/VH0, and for VK8/VH7-IL2 and VK0/VH0-IL2.

4D. Structure-Function Relationships Useful in Constructing Active KS-¼ Antibodies Taken together, the antigen binding activities of KS-¼ antibodies and fusion proteins with the disclosed V region sequences provide guidance in designing sequences of KS-¼ antibodies to EpCAM, as well as for proper expression and secretion of KS-¼ antibodies. In particular, the KS-¼ heavy and light chain V regions can tolerate multiple amino acid substitutions and retain activity, provided that these amino acid substitutions are outside the CDRs. The KS-¼ heavy and light chain V regions do not generally appear to tolerate amino acid insertions, especially within CDRs or in framework regions between CDRs.

For example, if the hybridoma KS-¼ sequence is taken to be a starting, "wild-type" sequence, the data indicate that the heavy chain V region can tolerate amino acid substitutions at positions 9, 11, 16, 17, 38, 40, 69, 70, 71, 72, 76, 79, 80, 83, 88, 91, and 111 with little or no loss of activity. Similarly, the light chain can tolerate amino acid substitutions at positions 1, 3, 10, 11, 12, 13, 17, 18, 19, 21, 41, 42, 59, 71, 73, 75, 77, and 103 with little or no loss of activity. These changes are outside the CDRs of KS-¼ heavy and light chain V regions. The 17 clearly acceptable heavy chain amino acid substitutions represent about 21% of the amino acid positions outside the CDRs, and about 68% of the amino acid positions outside the CDRs for which an amino acid substitution was attempted. Similarly, the eighteen clearly acceptable light chain amino acid substitutions represent about 23% of the amino acid positions outside the CDRs, and about 72% of the amino acid positions outside the CDRs for which an amino acid substitution was attempted. There were only two examples of an amino acid substitution outside of a CDR that resulted in a significantly less useful protein: the substitution Ala79Pro in the light chain, which appeared to have a negative impact on expression; and the substitution Q108T in the heavy chain, which had a negative impact on antigen binding. Thus, an amino acid substitution can be introduced into a KS-¼ antibody heavy chain or light chain sequence outside of a CDR, and there is a high probability that the substitution will result in an active protein.

Mutations involving the substitution of an amino acid in a CDR often have a negative impact on antigen binding. For example, the substitution I100M in the heavy chain reduces binding by about 8-fold. Mutations that involve the insertion of an amino acid generally have a negative impact on the utility of a KS-¼ sequence. For example, the VH-'369 heavy chain V region is unable to assemble into a proper antibody with a light chain, as described herein. The VH2.1 to 2.4 mutations have an insertion of an amino acid in CDR3 of the heavy chain V region, and each of these mutations has a negative impact on antigen binding.

Example 5

Immunogenicity of a KS Antibody (Construct 3)-IL2 Fusion Protein in Humans

In a human clinical trial, twenty two patients received one or more treatment regimes, with each treatment regime comprising three consecutive daily 4-hour intraveous infusions of KS antibody (Construct 3)-IL2. Each treatment regime was separated by a month (Weber et al. (2001). Proc. Am. Soc. Clin. Oncology 20:259a.). Serum samples were harvested from each patient before and after each treatment regime and tested for antibody reactivity against the whole KS Antibody (Construct 3)-IL2 molecule or the Fc-IL2 component (without the Fv region). No reactivity was observed in any of the pre-immune sera. The results indicated that only 4 patients experienced any significant immune response against either the Fv regions alone, or both the Fv regions and the Fc-IL2 component. Furthermore, these responses did not appear to be boosted upon subsequent exposure to huKS-IL2.

It is believed that the use of the antibody-IL2 fusion protein constitutes a particularly stringent test of the immunogenicity of the V region, because the interleukin-2 moiety has an adjuvant effect. Accordingly, the results indicate that the KS Antibody (Construct 3) may be administered to humans with only a small number of recipients apparently developing an antibody response to the KS antibody (Construct 3)-IL2 fusion protein. These results are particularly encouraging in view of the fact that the KS antibody (Construct 3) contains a variable region that is almost entirely murine in origin but with a few amino acid residues replaced with the corresponding human amino acid residues.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes which come within the meaning and range of equivalency of the claims are intended to be embraced therein.

INCORPORATION BY REFERENCE

The disclosure of each of the patent documents and scientific publications disclosed herein, are incorporated by reference into this application in their entirety.

What is claimed is:

1. An anti-EpCAM protein comprising an antibody that binds human EpCAM, said antibody comprising an immunoglobulin light chain variable region comprising (i) amino acid residues 24-31 of SEQ ID NO:1; (ii) amino acid residues 49-55 of SEQ ID NO:1; and (iii) amino acid residues 88-96 of SEQ ID NO:1; and further comprising an amino acid sequence defining an immunoglobulin light chain framework region selected from the group consisting of: (i) amino acid residues 1-23 of SEQ ID NO:8; and (ii) amino acid residues 1-23 of SEQ ID NO:9.

2. The anti-EpCAM protein of claim 1, wherein the antibody comprises amino acids 1-106 of SEQ ID NO:9.

3. The anti-EpCAM protein of claim 1, wherein the antibody has a Kd for EpCAM of at least $10^{-8}$ M.

4. The anti-EpCAM protein of claim 1, wherein the protein comprises a cytokine.

5. The anti-EpCAM protein of claim 4, wherein the cytokine is IL-2.

6. An anti-EpCAM protein, wherein the protein comprises an antibody that binds human EpCAM, said antibody comprising an immunoglobulin heavy chain variable region comprising (i) amino acid residues 26-35 of SEQ ID NO:2; (ii) amino acid residues 50-62 of SEQ ID NO:2; and (iii) amino acid residues 101-105 of SEQ ID NO:2; and further comprising an amino acid sequence defining an immunoglobulin heavy chain framework region selected from the group consisting of: (i) amino acid residues 1-25 of SEQ ID NO:18; and (ii) amino acid residues 67-98 of SEQ ID NO:18.

7. The anti-EpCAM protein of claim 6, wherein the antibody comprises amino acids 1-116 of SEQ ID NO:18.

8. The anti-EpCAM protein of claim 6, wherein the antibody has a Kd for EpCAM of at least $10^{-8}$ M.

9. The anti-EpCAM protein of claim 6, wherein the protein comprises a cytokine.

10. The anti-EpCAM protein of claim 9, wherein the cytokine is IL-2.

11. An anti-EpCAM protein, wherein the protein comprises an antibody that binds human EpCAM, said antibody comprising an antibody light chain comprising the amino acid sequence defined by residues 1-106 of SEQ ID NO:9 and an antibody heavy chain comprising the amino acid sequence defined by residues 1-116 of SEQ ID NO:18.

12. The anti-EpCAM protein of claim 11, wherein the protein comprises a cytokine.

13. The anti-EpCAM protein of claim 12, wherein the cytokine is IL-2.

14. A humanized or deimmunized anti-EpCAM protein suitable for administering into a human patient for treating a disease associated with EpCAM over-expression, wherein the protein comprises an antibody that binds human EpCAM, said antibody comprising an immunoglobulin light chain variable region comprising (i) amino acid residues 24-31 of SEQ ID NO:1; (ii) amino acid residues 49-55 of SEQ ID NO:1; and (iii) amino acid residues 88-96 of SEQ ID NO:1; and further comprising an amino acid sequence defining an immunoglobulin light chain framework region selected from the group consisting of: (i) amino acid residues 1-23 of SEQ ID NO:8; and (ii) amino acid residues 1-23 of SEQ ID NO:9.

15. A humanized or deimmunized anti-EpCAM protein suitable for administering into a human patient for treating a disease associated with EpCAM over-expression, wherein the protein comprises an antibody that binds human EpCAM, said antibody comprising an immunoglobulin heavy chain variable region comprising (i) amino acid residues 26-35 of SEQ ID NO:2; (ii) amino acid residues 50-62 of SEQ ID NO:2; and (iii) amino acid residues 101-105 of SEQ ID NO:2; and further comprising an amino acid sequence defining an immunoglobulin heavy chain framework region selected from the group consisting of: (i) amino acid residues 1-25 of SEQ ID NO:18; and (ii) amino acid residues 67-98 of SEQ ID NO:18.

16. A humanized or deimmunized anti-EpCAM protein suitable for administering into a human patient for treating a disease associated with EpCAM over-expression, wherein the protein comprises an antibody that binds human EpCAM, said antibody comprising an antibody light chain comprising the amino acid sequence defined by residues 1-106 of SEQ ID NO:9 and an antibody heavy chain comprising the amino acid sequence defined by residues 1-116 of SEQ ID NO:18.

* * * * *

```
                         SEQUENCE LISTING

<160> NUMBER OF SEQ ID NOS: 42

<210> SEQ ID NO 1
    <211> LENGTH: 106
    <212> TYPE: PRT
    <213> ORGANISM: Artificial
    <220> FEATURE:
    <223> OTHER INFORMATION: KS VK mouse

<400> SEQUENCE: 1

Gln Ile Leu Leu Thr Gln Ser Pro Ala Ile Met Ser Ala Ser Pro Gly
    1               5                   10                  15

Glu Lys Val Thr Met Thr Cys Ser Ala Ser Ser Ser Val Ser Tyr Met
                20                  25                  30

Leu Trp Tyr Gln Gln Lys Pro Gly Ser Ser Pro Lys Pro Trp Ile Phe
            35                  40                  45

Asp Thr Ser Asn Leu Ala Ser Gly Phe Pro Ala Arg Phe Ser Gly Ser
        50                  55                  60

Gly Ser Gly Thr Ser Tyr Ser Leu Ile Ile Ser Ser Met Glu Ala Glu
    65                  70                  75                  80

Asp Ala Ala Thr Tyr Tyr Cys His Gln Arg Ser Gly Tyr Pro Tyr Thr
                    85                  90                  95

Phe Gly Gly Gly Thr Lys Leu Glu Ile Lys
                100                 105

<210> SEQ ID NO 2
    <211> LENGTH: 116
    <212> TYPE: PRT
    <213> ORGANISM: Artificial
    <220> FEATURE:
    <223> OTHER INFORMATION: KS VH mouse

<400> SEQUENCE: 2

Gln Ile Gln Leu Val Gln Ser Gly Pro Glu Leu Lys Lys Pro Gly Glu
    1               5                   10                  15

Thr Val Lys Ile Ser Cys Lys Ala Ser Gly Tyr Thr Phe Thr Asn Tyr
                20                  25                  30

Gly Met Asn Trp Val Arg Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Glu Thr Ser Ala Ser Thr Ala Phe
    65                  70                  75                  80

Leu Gln Leu Asn Asn Leu Arg Ser Glu Asp Thr Ala Thr Tyr Phe Cys
                    85                  90                  95
```

```
Val Arg Phe Ile Ser Lys Gly Asp Tyr Trp Gly Gln Gly Thr Ser Val
            100                 105                 110

Thr Val Ser Ser
        115

<210> SEQ ID NO 3
<211> LENGTH: 106
<212> TYPE: PRT
<213> ORGANISM: Artificial
<220> FEATURE:
<223> OTHER INFORMATION: variable light chain sequence in the EpCAM
      antibody
<220> FEATURE:
<221> NAME/KEY: misc_feature
<222> LOCATION: (1)..(1)
<223> OTHER INFORMATION: wherein Xaa at position 1 is a glutamic acid or
                        a glutamine
<220> FEATURE:
<221> NAME/KEY: misc_feature
<222> LOCATION: (3)..(3)
<223> OTHER INFORMATION: wherein Xaa at position 3 is a valine or a
      leucine
<220> FEATURE:
<221> NAME/KEY: misc_feature
<222> LOCATION: (10)..(10)
<223> OTHER INFORMATION: wherein Xaa at position 10 is an isoleucine,
      a threonine or a serine
<220> FEATURE:
<221> NAME/KEY: misc_feature
<222> LOCATION: (11)..(11)
<223> OTHER INFORMATION: wherein Xaa at position 11 is a leucine or
      methionine
<220> FEATURE:
<221> NAME/KEY: misc_feature
<222> LOCATION: (12)..(12)
<223> OTHER INFORMATION: wherein Xaa at position 12 is an alanine or a
      serine
<220> FEATURE:
<221> NAME/KEY: misc_feature
<222> LOCATION: (13)..(13)
<223> OTHER INFORMATION: wherein Xaa at position 13 is an alanine, a
      leucine or a valine
<220> FEATURE:
<221> NAME/KEY: misc_feature
<222> LOCATION: (17)..(17)
<223> OTHER INFORMATION: wherein Xaa at position 17 is a glutamine or a
      glutamic acid
<220> FEATURE:
<221> NAME/KEY: misc_feature
<222> LOCATION: (18)..(18)
<223> OTHER INFORMATION: wherein Xaa at position 18 is an arginine or a
      lysine
<220> FEATURE:
<221> NAME/KEY: misc_feature
<222> LOCATION: (19)..(19)
<223> OTHER INFORMATION: wherein Xaa at position 19 is an alanine or a
      valine
<220> FEATURE:
<221> NAME/KEY: misc_feature
<222> LOCATION: (21)..(21)
<223> OTHER INFORMATION: wherein Xaa at position 21 is a methionine, a
      leucine or an isoleucine
<220> FEATURE:
<221> NAME/KEY: misc_feature
<222> LOCATION: (32)..(32)
<223> OTHER INFORMATION: wherein Xaa at position 32 is an isoleucine or
      a methionine
<220> FEATURE:
<221> NAME/KEY: misc_feature
<222> LOCATION: (36)..(36)
<223> OTHER INFORMATION: wherein Xaa at position 36 is a leucine or a
      glutamine
<220> FEATURE:
<221> NAME/KEY: misc_feature
<222> LOCATION: (41)..(41)
<223> OTHER INFORMATION: wherein Xaa at position 41 is a glutamine or a
```

```
      serine
<220> FEATURE:
<221> NAME/KEY: misc_feature
<222> LOCATION: (42)..(42)
<223> OTHER INFORMATION: wherein Xaa at position 42 is a serine, an
      alanine or a proline
<220> FEATURE:
<221> NAME/KEY: misc_feature
<222> LOCATION: (45)..(45)
<223> OTHER INFORMATION: wherein Xaa at position 45 is a leucine or a
      proline
<220> FEATURE:
<221> NAME/KEY: misc_feature
<222> LOCATION: (46)..(46)
<223> OTHER INFORMATION: wherein Xaa at position 46 is a leucine or a
      typtophan
<220> FEATURE:
<221> NAME/KEY: misc_feature
<222> LOCATION: (48)..(48)
<223> OTHER INFORMATION: wherein Xaa at position 48 is a tyrosine or a
      phenylalanine
<220> FEATURE:
<221> NAME/KEY: misc_feature
<222> LOCATION: (57)..(57)
<223> OTHER INFORMATION: wherein Xaa at position 57 is an isoleucine or
      a phenylalanine
<220> FEATURE:
<221> NAME/KEY: misc_feature
<222> LOCATION: (59)..(59)
<223> OTHER INFORMATION: wherein Xaa at position 59 is a serine or an
      alanine
<220> FEATURE:
<221> NAME/KEY: misc_feature
<222> LOCATION: (69)..(69)
<223> OTHER INFORMATION: wherein Xaa at position 69 is a serine, an
      aspartic acid or a threonine
<220> FEATURE:
<221> NAME/KEY: misc_feature
<222> LOCATION: (71)..(71)
<223> OTHER INFORMATION: wherein Xaa at position 71 is a threonine or
      an isoleucine
<220> FEATURE:
<221> NAME/KEY: misc_feature
<222> LOCATION: (73)..(73)
<223> OTHER INFORMATION: wherein Xaa at position 73 is a threonine or an
      isoleucine
<220> FEATURE:
<221> NAME/KEY: misc_feature
<222> LOCATION: (75)..(75)
<223> OTHER INFORMATION: wherein Xaa at position 75 is an asparagine or
      a serine
<220> FEATURE:
<221> NAME/KEY: misc_feature
<222> LOCATION: (77)..(77)
<223> OTHER INFORMATION: wherein Xaa at position 77 is a leucine or a
      methionine
<220> FEATURE:
<221> NAME/KEY: misc_feature
<222> LOCATION: (79)..(79)
<223> OTHER INFORMATION: wherein Xaa at position 79 is a proline or an
      alanine
<220> FEATURE:
<221> NAME/KEY: misc_feature
<222> LOCATION: (82)..(82)
<223> OTHER INFORMATION: wherein Xaa at position 82 is a phenylalanine
      or an alanine
<220> FEATURE:
<221> NAME/KEY: misc_feature
<222> LOCATION: (84)..(84)
<223> OTHER INFORMATION: wherein Xaa at position 84 is a valine or a
      threonine
<220> FEATURE:
<221> NAME/KEY: misc_feature
<222> LOCATION: (103)..(103)
<223> OTHER INFORMATION: wherein Xaa at position 103 is a valine or a
      leucine

<400> SEQUENCE: 3
```

```
Xaa Ile Xaa Leu Thr Gln Ser Pro Ala Xaa Xaa Xaa Xaa Ser Pro Gly
1               5                   10                  15

Xaa Xaa Xaa Thr Xaa Thr Cys Ser Ala Ser Ser Val Ser Thr Xaa
            20              25                  30

Leu Trp Tyr Xaa Gln Lys Pro Gly Xaa Xaa Pro Lys Xaa Xaa Ile Xaa
            35                  40                  45

Asp Thr Ser Asn Leu Ala Ser Gly Xaa Pro Xaa Arg Phe Ser Gly Ser
50                  55                  60

Gly Ser Gly Thr Xaa Tyr Xaa Leu Xaa Ile Xaa Ser Xaa Glu Xaa Glu
65                  70                  75                  80

Asp Xaa Ala Xaa Tyr Tyr Cys His Gln Arg Ser Gly Tyr Pro Tyr Thr
            85                  90                  95

Phe Gly Gly Gly Thr Lys Xaa Glu Ile Lys
                100                 105
```

<210> SEQ ID NO 4
<211> LENGTH: 116
<212> TYPE: PRT
<213> ORGANISM: Artificial
<220> FEATURE:
<223> OTHER INFORMATION: variable heavy chain sequence in the EpCAM
      antibody
<220> FEATURE:
<221> NAME/KEY: misc_feature
<222> LOCATION: (2)..(2)
<223> OTHER INFORMATION: wherein Xaa at position 2 is an isoleucine or a
      valine
<220> FEATURE:
<221> NAME/KEY: misc_feature
<222> LOCATION: (9)..(9)
<223> OTHER INFORMATION: wherein Xaa at position 9 is a proline or an
      alanine
<220> FEATURE:
<221> NAME/KEY: misc_feature
<222> LOCATION: (11)..(11)
<223> OTHER INFORMATION: wherein Xaa at position 11 is a leucine or a
      valine
<220> FEATURE:
<221> NAME/KEY: misc_feature
<222> LOCATION: (16)..(16)
<223> OTHER INFORMATION: wherein Xaa at position 16 is a glutamic acid
      or a serine
<220> FEATURE:
<221> NAME/KEY: misc_feature
<222> LOCATION: (17)..(17)
<223> OTHER INFORMATION: wherein Xaa at position 17 is a threonine or a
      serine
<220> FEATURE:
<221> NAME/KEY: misc_feature
<222> LOCATION: (38)..(38)
<223> OTHER INFORMATION: wherein Xaa at position 38 is a lysine or an
      arginine
<220> FEATURE:
<221> NAME/KEY: misc_feature
<222> LOCATION: (40)..(40)
<223> OTHER INFORMATION: wherein Xaa at position 40 is a threonine or an
      alanine
<220> FEATURE:
<221> NAME/KEY: misc_feature
<222> LOCATION: (43)..(43)
<223> OTHER INFORMATION: wherein Xaa at position 43 is a lysine or a
      glutamine
<220> FEATURE:
<221> NAME/KEY: misc_feature
<222> LOCATION: (46)..(46)
<223> OTHER INFORMATION: wherein Xaa at position 46 is a lysine or a
      glutamic acid
<220> FEATURE:
<221> NAME/KEY: msic_feature
<222> LOCATION: (63)..(63)
<223> OTHER INFORMATION: wherein Xaa at position 63 is an aspartic acid
      or a lysine

```
<220> FEATURE:
<221> NAME/KEY: misc_feature
<222> LOCATION: (65)..(65)
<223> OTHER INFORMATION: wherein Xaa at position 65 is a lysine or a
      glutamine
<220> FEATURE:
<221> NAME/KEY: misc_feature
<222> LOCATION: (68)..(68)
<223> OTHER INFORMATION: wherein Xaa at position 68 is a phenylalanine
      or a valine
<220> FEATURE:
<221> NAME/KEY: misc_feature
<222> LOCATION: (69)..(69)
<223> OTHER INFORMATION: wherein Xaa at position 69 is an alanine, a
      threonine or a valine
<220> FEATURE:
<221> NAME/KEY: misc_feature
<222> LOCATION: (70)..(70)
<223> OTHER INFORMATION: wherein Xaa at position 70 is a phenylalanine
      or an isoleucine
<220> FEATURE:
<221> NAME/KEY: misc_feature
<222> LOCATION: (71)..(71)
<223> OTHER INFORMATION: wherein Xaa at position 71 is a serine or a
      threonine
<220> FEATURE:
<221> NAME/KEY: misc_feature
<222> LOCATION: (72)..(72)
<223> OTHER INFORMATION: wherein Xaa at position 72 is a leucine or an
      alanine
<220> FEATURE:
<221> NAME/KEY: misc_feature
<222> LOCATION: (73)..(73)
<223> OTHER INFORMATION: wherein Xaa at position 73 is a glutamic acid
      or an aspartic acid
<220> FEATURE:
<221> NAME/KEY: misc_feature
<222> LOCATION: (76)..(76)
<223> OTHER INFORMATION: wherein Xaa at position 76 is an alanine or a
      threonine
<220> FEATURE:
<221> NAME/KEY: misc_feature
<222> LOCATION: (79)..(79)
<223> OTHER INFORMATION: wherein Xaa at position 79 is an alanine or a
      leucine
<220> FEATURE:
<221> NAME/KEY: misc_feature
<222> LOCATION: (80)..(80)
<223> OTHER INFORMATION: wherein Xaa at position 80 is a phenylalanine
      or a tyrosine
<220> FEATURE:
<221> NAME/KEY: misc_feature
<222> LOCATION: (83)..(83)
<223> OTHER INFORMATION: wherein Xaa at position 83 is an isoleucine or
      a leucine
<220> FEATURE:
<221> NAME/KEY: misc_feature
<222> LOCATION: (84)..(84)
<223> OTHER INFORMATION: wherein Xaa at position 84 is an asparagine or
      a serine
<220> FEATURE:
<221> NAME/KEY: misc_feature
<222> LOCATION: (85)..(85)
<223> OTHER INFORMATION: wherein Xaa at position 85 is an asparagine or
      a serine
<220> FEATURE:
<221> NAME/KEY: misc_feature
<222> LOCATION: (88)..(88)
<223> OTHER INFORMATION: wherein Xaa at position 88 is an asparagine, an
      alanine or a serine
<220> FEATURE:
<221> NAME/KEY: misc_feature
<222> LOCATION: (91)..(91)
<223> OTHER INFORMATION: wherein Xaa at position 91 is a methionine or
      a threonine
<220> FEATURE:
<221> NAME/KEY: misc_feature
<222> LOCATION: (93)..(93)
<223> OTHER INFORMATION: wherein Xaa at position 93 is a threonine or
```

-continued

```
      a valine
<220> FEATURE:
<221> NAME/KEY: misc_feature
<222> LOCATION: (100)..(100)
<223> OTHER INFORMATION: wherein Xaa at position 100 is an isoleucine or
      a methionine
<220> FEATURE:
<221> NAME/KEY: misc_feature
<222> LOCATION: (108)..(108)
<223> OTHER INFORMATION: wherein Xaa at position 108 is a glutamine or a
      threonine
<220> FEATURE:
<221> NAME/KEY: misc_feature
<222> LOCATION: (111)..(111)
<223> OTHER INFORMATION: wherein Xaa at position 111 is a serine or a
      threonine

<400> SEQUENCE: 4

Gln Xaa Gln Leu Val Gln Ser Gly Xaa Glu Xaa Lys Lys Pro Gly Xaa
1               5                  10                  15

Xaa Val Lys Ile Ser Cys Lys Ala Ser Gly Tyr Thr Phe Thr Asn Tyr
            20                  25                  30

Gly Met Asn Trp Val Xaa Gln Xaa Pro Gly Xaa Gly Leu Xaa Trp Met
        35                  40                  45

Gly Trp Ile Asn Thr Tyr Thr Gly Glu Pro Thr Tyr Ala Asp Xaa Phe
    50                  55                  60

Xaa Gly Arg Xaa Xaa Xaa Xaa Xaa Thr Ser Xaa Ser Thr Xaa Xaa
65                  70                  75                  80

Leu Gln Xaa Xaa Xaa Leu Arg Xaa Glu Asp Xaa Ala Xaa Tyr Phe Cys
                85                  90                  95

Val Arg Phe Xaa Ser Lys Gly Asp Tyr Trp Gly Xaa Gly Thr Xaa Val
            100                 105                 110

Thr Val Ser Ser
        115

<210> SEQ ID NO 5
<211> LENGTH: 106
<212> TYPE: PRT
<213> ORGANISM: Artificial
<220> FEATURE:
<223> OTHER INFORMATION: light sequence consensus
<220> FEATURE:
<221> NAME/KEY: misc_feature
<222> LOCATION: (1)..(1)
<223> OTHER INFORMATION: wherein xaa at position 1 is a glutamine or a
      glutamic acid
<220> FEATURE:
<221> NAME/KEY: misc_feature
<222> LOCATION: (3)..(3)
<223> OTHER INFORMATION: wherein Xaa at position 3 is a leucine or a
      valine
<220> FEATURE:
<221> NAME/KEY: misc_feature
<222> LOCATION: (10)..(10)
<223> OTHER INFORMATION: wherein Xaa at position 10 is an isoleucine or
      a threonine
<220> FEATURE:
<221> NAME/KEY: misc_feature
<222> LOCATION: (11)..(11)
<223> OTHER INFORMATION: wherein Xaa at position 11 is a methionine or
      a leucine
<220> FEATURE:
<221> NAME/KEY: misc_feature
<222> LOCATION: (13)..(13)
<223> OTHER INFORMATION: wherein Xaa at position 13 is an alanine or a
      leucine
<220> FEATURE:
<221> NAME/KEY: misc_feature
<222> LOCATION: (18)..(18)
<223> OTHER INFORMATION: wherein Xaa at position 18 is a lysine or an
``` arginine
<220> FEATURE:
<221> NAME/KEY: misc_feature
<222> LOCATION: (21)..(21)
<223> OTHER INFORMATION: wherein Xaa at position 21 is a methionine or
      a leucine
<220> FEATURE:
<221> NAME/KEY: misc_feature
<222> LOCATION: (41)..(41)
<223> OTHER INFORMATION: wherein Xaa at position 41 is a serine or a
      glutamine
<220> FEATURE:
<221> NAME/KEY: misc_feature
<222> LOCATION: (42)..(42)
<223> OTHER INFORMATION: wherein Xaa at position 42 is a serine or an
      alanine
<220> FEATURE:
<221> NAME/KEY: misc_feature
<222> LOCATION: (45)..(45)
<223> OTHER INFORMATION: wherein Xaa at position 45 is a proline or a
      leucine
<220> FEATURE:
<221> NAME/KEY: misc_feature
<222> LOCATION: (46)..(46)
<223> OTHER INFORMATION: wherein Xaa at position 46 is a tryptophan or a
      leucine
<220> FEATURE:
<221> NAME/KEY: misc_feature
<222> LOCATION: (57)..(57)
<223> OTHER INFORMATION: wherein Xaa at position 57 is a phenylalanine
      or an isoleucine
<220> FEATURE:
<221> NAME/KEY: misc_feature
<222> LOCATION: (69)..(69)
<223> OTHER INFORMATION: wherein Xaa at position 69 is a serine or an
      aspartic acid
<220> FEATURE:
<221> NAME/KEY: misc_feature
<222> LOCATION: (71)..(71)
<223> OTHER INFORMATION: wherein Xaa at position 71 is a serine or a
      threonine
<220> FEATURE:
<221> NAME/KEY: misc_feature
<222> LOCATION: (73)..(73)
<223> OTHER INFORMATION: wherein Xaa at position 73 is an isoleucine or
      a threonine
<220> FEATURE:
<221> NAME/KEY: misc_feature
<222> LOCATION: (77)..(77)
<223> OTHER INFORMATION: wherein Xaa at position 77 is a methionine or a
      leucine
<220> FEATURE:
<221> NAME/KEY: misc_feature
<222> LOCATION: (79)..(79)
<223> OTHER INFORMATION: wherein Xaa at position 79 is an alanine or a
      proline
<220> FEATURE:
<221> NAME/KEY: misc_feature
<222> LOCATION: (82)..(82)
<223> OTHER INFORMATION: wherein Xaa at position 82 is an alanine or a
      phenylalanine
<220> FEATURE:
<221> NAME/KEY: misc_feature
<222> LOCATION: (84)..(84)
<223> OTHER INFORMATION: wherein Xaa at position 84 is a threonine or
      a valine

<400> SEQUENCE: 5

Xaa Ile Xaa Leu Thr Gln Ser Pro Ala Xaa Xaa Ser Xaa Ser Pro Gly
1               5                   10                  15

Glu Xaa Val Thr Xaa Thr Cys Ser Ala Ser Ser Ser Val Ser Thr Met
            20                  25                  30

Leu Trp Tyr Gln Gln Lys Pro Gly Xaa Xaa Pro Lys Xaa Xaa Ile Phe
        35                  40                  45

Asp Thr Ser Asn Leu Ala Ser Gly Xaa Pro Ala Arg Phe Ser Gly Ser

```
                50              55              60
Gly Ser Gly Thr Xaa Tyr Xaa Leu Xaa Ile Ser Ser Xaa Glu Xaa Glu
 65              70              75              80

Asp Xaa Ala Xaa Tyr Tyr Cys His Gln Arg Ser Gly Tyr Pro Tyr Thr
             85              90              95

Phe Gly Gly Gly Thr Lys Leu Glu Ile Lys
            100             105
```

```
<210> SEQ ID NO 6
<211> LENGTH: 116
<212> TYPE: PRT
<213> ORGANISM: Artificial
<220> FEATURE:
<223> OTHER INFORMATION: heavy sequence consensus
<220> FEATURE:
<221> NAME/KEY: misc_feature
<222> LOCATION: (2)..(2)
<223> OTHER INFORMATION: wherein Xaa at position 2 is an isoleucine or a
      valine
<220> FEATURE:
<221> NAME/KEY: misc_feature
<222> LOCATION: (9)..(9)
<223> OTHER INFORMATION: wherein Xaa at position 9 is a proline or an
      alanine
<220> FEATURE:
<221> NAME/KEY: misc_feature
<222> LOCATION: (11)..(11)
<223> OTHER INFORMATION: wherein Xaa at position 11 is a leucine or a
      valine
<220> FEATURE:
<221> NAME/KEY: misc_feature
<222> LOCATION: (17)..(17)
<223> OTHER INFORMATION: wherein Xaa at position 17 is a threonine or a
      serine
<220> FEATURE:
<221> NAME/KEY: misc_feature
<222> LOCATION: (38)..(38)
<223> OTHER INFORMATION: wherein Xaa at position 38 is a lysine or an
      arginine
<220> FEATURE:
<221> NAME/KEY: misc_feature
<222> LOCATION: (40)..(40)
<223> OTHER INFORMATION: wherein Xaa at position 40 is a threonine or an
      alanine
<220> FEATURE:
<221> NAME/KEY: misc_featrue
<222> LOCATION: (46)..(46)
<223> OTHER INFORMATION: wherein Xaa at position 46 is a lysine or a
      glutamic acid
<220> FEATURE:
<221> NAME/KEY: misc_feature
<222> LOCATION: (63)..(63)
<223> OTHER INFORMATION: wherein Xaa at position 63 is an aspartic acid
      or a lysine
<220> FEATURE:
<221> NAME/KEY: misc_feature
<222> LOCATION: (65)..(65)
<223> OTHER INFORMATION: wherein Xaa at position 65 is a lysine or a
      glutamine
<220> FEATURE:
<221> NAME/KEY: misc_feature
<222> LOCATION: (68)..(68)
<223> OTHER INFORMATION: wherein Xaa at position 68 is a phenylalanine
      or a valine
<220> FEATURE:
<221> NAME/KEY: misc_feature
<222> LOCATION: (69)..(69)
<223> OTHER INFORMATION: wherein Xaa at position 69 is an alanine or a
      threonine
<220> FEATURE:
<221> NAME/KEY: misc_feature
<222> LOCATION: (70)..(70)
<223> OTHER INFORMATION: wherein Xaa at position 70 is a phenylalanine
      or an isoleucine
<220> FEATURE:
```

-continued

```
<221> NAME/KEY: misc_feature
<222> LOCATION: (73)..(73)
<223> OTHER INFORMATION: wherein Xaa at position 73 is a glutamic acid
      or an aspartic acid
<220> FEATURE:
<221> NAME/KEY: misc_feature
<222> LOCATION: (76)..(76)
<223> OTHER INFORMATION: wherein Xaa at position 76 is an alanine or a
      threonine
<220> FEATURE:
<221> NAME/KEY: misc_feature
<222> LOCATION: (80)..(80)
<223> OTHER INFORMATION: wherein Xaa at position 80 is a phenylalanine
      or a tyrosine
<220> FEATURE:
<221> NAME/KEY: misc_feature
<222> LOCATION: (83)..(83)
<223> OTHER INFORMATION: wherein Xaa at position 83 is an isoleucine or
      a leucine
<220> FEATURE:
<221> NAME/KEY: misc_feature
<222> LOCATION: (84)..(84)
<223> OTHER INFORMATION: wherein Xaa at position 84 is an asparagine or
      a serine
<220> FEATURE:
<221> NAME/KEY: misc_feature
<222> LOCATION: (85)..(85)
<223> OTHER INFORMATION: wherein Xaa at position 85 is an asparagine or
      a serine
<220> FEATURE:
<221> NAME/KEY: misc_feature
<222> LOCATION: (88)..(88)
<223> OTHER INFORMATION: wherein Xaa at position 88 is an asparagine, an
      alanine or a serine
<220> FEATURE:
<221> NAME/KEY: misc_feature
<222> LOCATION: (91)..(91)
<223> OTHER INFORMATION: wherein Xaa at position 91 is a methionine or a
      threonine
<220> FEATURE:
<221> NAME/KEY: misc_feature
<222> LOCATION: (93)..(93)
<223> OTHER INFORMATION: wherein Xaa at position 93 is a threonine or a
      valine
<220> FEATURE:
<221> NAME/KEY: misc_feature
<222> LOCATION: (108)..(108)
<223> OTHER INFORMATION: wherein Xaa at position 108 is a glutamine or a
      threonine

<400> SEQUENCE: 6

Gln Xaa Gln Leu Val Gln Ser Gly Xaa Glu Xaa Lys Lys Pro Gly Glu
 1               5                  10                  15

Xaa Val Lys Ile Ser Cys Lys Ala Ser Gly Tyr Thr Phe Thr Asn Tyr
            20                  25                  30

Gly Met Asn Trp Val Xaa Gln Xaa Pro Gly Lys Gly Leu Xaa Trp Met
        35                  40                  45

Gly Trp Ile Asn Thr Tyr Thr Gly Glu Pro Thr Tyr Ala Asp Xaa Phe
    50                  55                  60

Xaa Gly Arg Xaa Xaa Xaa Ser Leu Xaa Thr Ser Xaa Ser Thr Ala Xaa
65                  70                  75                  80

Leu Gln Xaa Xaa Xaa Leu Arg Xaa Glu Asp Xaa Ala Xaa Tyr Phe Cys
                85                  90                  95

Val Arg Phe Ile Ser Lys Gly Asp Tyr Trp Gly Xaa Gly Thr Ser Val
            100                 105                 110

Thr Val Ser Ser
        115

<210> SEQ ID NO 7
<211> LENGTH: 106
```

```
<212> TYPE: PRT
<213> ORGANISM: Artificial
<220> FEATURE:
<223> OTHER INFORMATION: Vk6 light chain

<400> SEQUENCE: 7

Glu Ile Val Leu Thr Gln Ser Pro Ala Thr Leu Ser Leu Ser Pro Gly
1               5                   10                  15

Glu Arg Val Thr Leu Thr Cys Ser Ala Ser Ser Val Ser Tyr Met
            20                  25                  30

Leu Trp Tyr Gln Gln Lys Pro Gly Gln Ala Pro Lys Leu Leu Ile Phe
        35                  40                  45

Asp Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys His Gln Arg Ser Gly Tyr Pro Tyr Thr
                85                  90                  95

Phe Gly Gly Gly Thr Lys Leu Glu Ile Lys
            100                 105

<210> SEQ ID NO 8
<211> LENGTH: 106
<212> TYPE: PRT
<213> ORGANISM: Artificial
<220> FEATURE:
<223> OTHER INFORMATION: VK7 light chain

<400> SEQUENCE: 8

Gln Ile Leu Leu Thr Gln Ser Pro Ala Ile Met Ser Ala Ser Pro Gly
1               5                   10                  15

Glu Arg Val Thr Met Thr Cys Ser Ala Ser Ser Ser Val Ser Tyr Met
            20                  25                  30

Leu Trp Tyr Gln Gln Lys Pro Gly Ser Ser Pro Lys Pro Trp Ile Phe
        35                  40                  45

Asp Thr Ser Asn Leu Ala Ser Gly Phe Pro Ala Arg Phe Ser Gly Ser
    50                  55                  60

Gly Ser Gly Thr Ser Tyr Ser Leu Ile Ile Ser Ser Met Glu Pro Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Leu Glu Ile Lys
            100                 105

<210> SEQ ID NO 9
<211> LENGTH: 106
<212> TYPE: PRT
<213> ORGANISM: Artificial
<220> FEATURE:
<223> OTHER INFORMATION: VK8 light chain

<400> SEQUENCE: 9

Glu Ile Val Leu Thr Gln Ser Pro Ala Thr Leu Ser Leu Ser Pro Gly
1               5                   10                  15

Glu Arg Val Thr Leu Thr Cys Ser Ala Ser Ser Ser Val Ser Tyr Met
            20                  25                  30

Leu Trp Tyr Gln Gln Lys Pro Gly Ser Ser Pro Lys Pro Trp Ile Phe
        35                  40                  45

Asp Thr Ser Asn Leu Ala Ser Gly Phe Pro Ala Arg Phe Ser Gly Ser
```

```
            50                  55                  60
Gly Ser Gly Thr Ser Tyr Ser Leu Ile Ile Ser Ser Met Glu Ala Glu
 65                  70                  75                  80

Asp Ala Ala Thr Tyr Tyr Cys His Gln Arg Ser Gly Tyr Pro Tyr Thr
                 85                  90                  95

Phe Gly Gly Gly Thr Lys Leu Glu Ile Lys
            100                 105

<210> SEQ ID NO 10
<211> LENGTH: 106
<212> TYPE: PRT
<213> ORGANISM: Artificial
<220> FEATURE:
<223> OTHER INFORMATION: KS VK veneered

<400> SEQUENCE: 10

Gln Ile Leu Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Met
                 20                  25                  30

Leu Trp Tyr Gln Gln Lys Pro Gly Gln Pro Pro Lys Pro Trp Ile Phe
             35                  40                  45

Asp Thr Ser Asn Leu Ala Ser Gly Phe Pro Ala Arg Phe Ser Gly Ser
         50                  55                  60

Gly Ser Gly Thr Ser Tyr Thr Leu Thr Ile Asn Ser Leu Glu Ala Glu
 65                  70                  75                  80

Asp Ala Ala Thr Tyr Tyr Cys His Gln Arg Ser Gly Tyr Pro Tyr Thr
                 85                  90                  95

Phe Gly Gly Gly Thr Lys Val Glu Ile Lys
            100                 105

<210> SEQ ID NO 11
<211> LENGTH: 106
<212> TYPE: PRT
<213> ORGANISM: Artificial
<220> FEATURE:
<223> OTHER INFORMATION: KS de-immunized VK1

<400> SEQUENCE: 11

Gln Ile Val Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Ile
                 20                  25                  30

Leu Trp Tyr Gln Gln Lys Pro Gly Gln Pro Pro Lys Pro Trp Ile Phe
             35                  40                  45

Asp Thr Ser Asn Leu Ala Ser Gly Phe Pro Ser Arg Phe Ser Gly Ser
         50                  55                  60

Gly Ser Gly Thr Ser Tyr Thr Leu Thr Ile Asn Ser Leu Glu Ala Glu
 65                  70                  75                  80

Asp Ala Ala Thr Tyr Tyr Cys His Gln Arg Ser Gly Tyr Pro Tyr Thr
                 85                  90                  95

Phe Gly Gly Gly Thr Lys Val Glu Ile Lys
            100                 105

<210> SEQ ID NO 12
<211> LENGTH: 106
<212> TYPE: PRT
<213> ORGANISM: Artificial
<220> FEATURE:
```

<223> OTHER INFORMATION: KS de-immunized VK2

<400> SEQUENCE: 12

Gln Ile Val Leu Thr Gln Ser Pro Ala Ser Leu Ala Val Ser Pro Gly
1               5                   10                  15

Gln Arg Ala Thr Ile Thr Cys Ser Ala Ser Ser Ser Val Ser Tyr Met
                20                  25                  30

Leu Trp Tyr Gln Gln Lys Pro Gly Gln Pro Pro Lys Pro Trp Ile Phe
            35                  40                  45

Asp Thr Ser Asn Leu Ala Ser Gly Phe Pro Ser Arg Phe Ser Gly Ser
        50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105

<210> SEQ ID NO 13
<211> LENGTH: 106
<212> TYPE: PRT
<213> ORGANISM: Artificial
<220> FEATURE:
<223> OTHER INFORMATION: KS-deimmunized VK3

<400> SEQUENCE: 13

Gln Ile Leu Leu Thr Gln Ser Pro Ala Ser Leu Ala Val Ser Pro Gly
1               5                   10                  15

Gln Arg Ala Thr Ile Thr Cys Ser Ala Ser Ser Ser Val Ser Tyr Met
                20                  25                  30

Leu Trp Tyr Gln Gln Lys Pro Gly Gln Pro Pro Lys Pro Trp Ile Phe
            35                  40                  45

Asp Thr Ser Asn Leu Ala Ser Gly Phe Pro Ser Arg Phe Ser Gly Ser
        50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105

<210> SEQ ID NO 14
<211> LENGTH: 106
<212> TYPE: PRT
<213> ORGANISM: Artificial
<220> FEATURE:
<223> OTHER INFORMATION: KS de-immunized VK4

<400> SEQUENCE: 14

Gln Ile Leu Leu Thr Gln Ser Pro Ala Ser Leu Ala Val Ser Pro Gly
1               5                   10                  15

Gln Arg Ala Thr Ile Thr Cys Ser Ala Ser Ser Ser Val Ser Tyr Met
                20                  25                  30

Leu Trp Tyr Gln Gln Lys Pro Gly Gln Pro Pro Lys Pro Trp Ile Phe
            35                  40                  45

Asp Thr Ser Asn Leu Ala Ser Gly Phe Pro Ala Arg Phe Ser Gly Ser
        50                  55                  60

Gly Ser Gly Thr Ser Tyr Thr Leu Thr Ile Asn Ser Leu Glu Ala Glu

-continued

```
                 65                  70                  75                  80
Asp Ala Thr Tyr Tyr Cys His Gln Arg Ser Gly Tyr Pro Tyr Thr
                     85                  90                  95

Phe Gly Gly Gly Thr Lys Val Glu Ile Lys
            100                 105

<210> SEQ ID NO 15
<211> LENGTH: 106
<212> TYPE: PRT
<213> ORGANISM: Artificial
<220> FEATURE:
<223> OTHER INFORMATION: KS de-immunized VK5

<400> SEQUENCE: 15

Gln Ile Leu Leu Thr Gln Ser Pro Ala Ser Leu Ala Val Ser Pro Gly
1               5                   10                  15

Gln Arg Ala Thr Ile Thr Cys Ser Ala Ser Ser Ser Val Ser Tyr Met
                20                  25                  30

Leu Trp Tyr Gln Gln Lys Pro Gly Ser Ser Pro Lys Pro Trp Ile Tyr
            35                  40                  45

Asp Thr Ser Asn Leu Ala Ser Gly Phe Pro Ala Arg Phe Ser Gly Ser
        50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105

<210> SEQ ID NO 16
<211> LENGTH: 106
<212> TYPE: PRT
<213> ORGANISM: Artificial
<220> FEATURE:
<223> OTHER INFORMATION: KS VK mouse

<400> SEQUENCE: 16

Gln Ile Val Leu Thr Gln Ser Pro Ala Thr Leu Ser Ala Ser Pro Gly
1               5                   10                  15

Glu Arg Val Thr Ile Thr Cys Ser Ala Ser Ser Ser Val Ser Tyr Met
                20                  25                  30

Leu Trp Tyr Leu Gln Lys Pro Gly Ser Ser Pro Lys Pro Trp Ile Phe
            35                  40                  45

Asp Thr Ser Asn Leu Ala Ser Gly Phe Pro Ser Arg Phe Ser Gly Ser
        50                  55                  60

Gly Ser Gly Thr Thr Tyr Ser Leu Ile Ile Ser Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Leu Glu Ile Lys
            100                 105

<210> SEQ ID NO 17
<211> LENGTH: 116
<212> TYPE: PRT
<213> ORGANISM: Artificial
<220> FEATURE:
<223> OTHER INFORMATION: VH6 heavy chain

<400> SEQUENCE: 17
```

Gln Val Gln Leu Val Gln Ser Gly Ala Glu Val Lys Lys Pro Gly Glu
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Pro Thr Tyr Ala Gln Lys Phe
    50                  55                  60

Gln Gly Arg Val Thr Ile Ser Leu Asp Thr Ser Thr Ser Thr Ala Tyr
65                  70                  75                  80

Leu Gln Leu Ser Ser Leu Arg Ala Glu Asp Thr Ala Val Tyr Phe Cys
                85                  90                  95

Val Arg Phe Ile Ser Lys Gly Asp Tyr Trp Gly Gln Gly Thr Ser Val
            100                 105                 110

Thr Val Ser Ser
        115

<210> SEQ ID NO 18
<211> LENGTH: 116
<212> TYPE: PRT
<213> ORGANISM: Artificial
<220> FEATURE:
<223> OTHER INFORMATION: VH7 heavy chain

<400> SEQUENCE: 18

Gln Ile Gln Leu Val Gln Ser Gly Ala Glu Val Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Thr Ser Thr Ala Phe
65                  70                  75                  80

Leu Gln Ile Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Ser Val
            100                 105                 110

Thr Val Ser Ser
        115

<210> SEQ ID NO 19
<211> LENGTH: 116
<212> TYPE: PRT
<213> ORGANISM: Artificial
<220> FEATURE:
<223> OTHER INFORMATION: VH2.5 heavy chain

<400> SEQUENCE: 19

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe

-continued

```
                50                  55                  60
Lys Gly Arg Phe Thr Ile Thr Ala Glu Thr Ser Thr Ser Thr Leu Tyr
 65                  70                  75                  80

Leu Gln Leu Asn Asn Leu Arg Ser Glu Asp Thr Ala Thr Tyr Phe Cys
                 85                  90                  95

Val Arg Phe Ile Ser Lys Gly Asp Tyr Trp Gly Thr Gly Thr Thr Val
            100                 105                 110

Thr Val Ser Ser
        115

<210> SEQ ID NO 20
<211> LENGTH: 116
<212> TYPE: PRT
<213> ORGANISM: Artificial
<220> FEATURE:
<223> OTHER INFORMATION: KS VH veneered

<400> SEQUENCE: 20

Gln Ile Gln Leu Val Gln Ser Gly Pro Glu Leu Lys Lys Pro Gly Ser
  1               5                  10                  15

Ser Val Lys Ile Ser Cys Lys Ala Ser Gly Tyr Thr Phe Thr Asn Tyr
                 20                  25                  30

Gly Met Asn Trp Val Lys Gln Ala Pro Gly Gln Gly Leu Lys Trp Met
             35                  40                  45

Gly Trp Ile Asn Thr Tyr Thr Gly Glu Pro Thr Tyr Ala Asp Asp Phe
         50                  55                  60

Lys Gly Arg Phe Thr Phe Thr Ile Glu Thr Ser Ser Thr Ala Tyr
 65                  70                  75                  80

Leu Gln Leu Asn Asn Leu Arg Ser Glu Asp Met Ala Thr Tyr Phe Cys
                 85                  90                  95

Val Arg Phe Ile Ser Lys Gly Asp Tyr Trp Gly Gln Gly Thr Thr Val
            100                 105                 110

Thr Val Ser Ser
        115

<210> SEQ ID NO 21
<211> LENGTH: 116
<212> TYPE: PRT
<213> ORGANISM: Artificial
<220> FEATURE:
<223> OTHER INFORMATION: KS de-immunized VH1

<400> SEQUENCE: 21

Gln Ile Gln Leu Val Gln Ser Gly Pro Glu Leu Lys Lys Pro Gly Ser
  1               5                  10                  15

Ser Val Lys Ile Ser Cys Lys Ala Ser Gly Tyr Thr Phe Thr Asn Tyr
                 20                  25                  30

Gly Met Asn Trp Val Arg Gln Ala Pro Gly Lys Gly Leu Lys Trp Met
             35                  40                  45

Gly Trp Ile Asn Thr Tyr Thr Gly Glu Pro Thr Tyr Ala Asp Asp Phe
         50                  55                  60

Lys Gly Arg Phe Thr Ile Thr Ala Glu Thr Ser Ser Thr Leu Tyr
 65                  70                  75                  80

Leu Gln Leu Asn Asn Leu Arg Ser Glu Asp Thr Ala Thr Tyr Phe Cys
                 85                  90                  95

Val Arg Phe Met Ser Lys Gly Asp Tyr Trp Gly Gln Gly Thr Thr Val
            100                 105                 110
```

Thr Val Ser Ser
        115

<210> SEQ ID NO 22
<211> LENGTH: 116
<212> TYPE: PRT
<213> ORGANISM: Artificial
<220> FEATURE:
<223> OTHER INFORMATION: KS de-immunized VH2

<400> SEQUENCE: 22

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Ala Glu Thr Ser Thr Ser Thr Leu Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115

<210> SEQ ID NO 23
<211> LENGTH: 116
<212> TYPE: PRT
<213> ORGANISM: Artificial
<220> FEATURE:
<223> OTHER INFORMATION: KS de-immunized VH3

<400> SEQUENCE: 23

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115

<210> SEQ ID NO 24
<211> LENGTH: 116
<212> TYPE: PRT
<213> ORGANISM: Artificial
<220> FEATURE:
<223> OTHER INFORMATION: KS- deimmunized VH4

<400> SEQUENCE: 24

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115

<210> SEQ ID NO 25
<211> LENGTH: 116
<212> TYPE: PRT
<213> ORGANISM: Artificial
<220> FEATURE:
<223> OTHER INFORMATION: KS de-immunized VH5

<400> SEQUENCE: 25

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115

<210> SEQ ID NO 26
<211> LENGTH: 116
<212> TYPE: PRT
<213> ORGANISM: Artificial
<220> FEATURE:
<223> OTHER INFORMATION: KS VH mouse

<400> SEQUENCE: 26

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

```
Gly Trp Ile Asn Thr Tyr Thr Gly Glu Pro Thr Tyr Ala Asp Asp Phe
 50                  55                  60

Lys Gly Arg Phe Val Phe Ser Leu Glu Thr Ser Ala Ser Thr Ala Phe
 65                  70                  75                  80

Leu Gln Leu Asn Asn Leu Arg Ser Glu Asp Thr Ala Thr Tyr Phe Cys
                 85                  90                  95

Val Arg Phe Ile Ser Lys Gly Asp Tyr Trp Gly Gln Gly Thr Ser Val
            100                 105                 110

Thr Val Ser Ser
        115
```

<210> SEQ ID NO 27
<211> LENGTH: 25
<212> TYPE: DNA
<213> ORGANISM: Artificial
<220> FEATURE:
<223> OTHER INFORMATION: KSA sense primer

<400> SEQUENCE: 27
tctagagcag catggcgccc ccgca                                       25

<210> SEQ ID NO 28
<211> LENGTH: 24
<212> TYPE: DNA
<213> ORGANISM: Artificial
<220> FEATURE:
<223> OTHER INFORMATION: KSA antisense primer

<400> SEQUENCE: 28
ctcgagttat gcattgagtt ccct                                        24

<210> SEQ ID NO 29
<211> LENGTH: 17
<212> TYPE: DNA
<213> ORGANISM: Artificial
<220> FEATURE:
<223> OTHER INFORMATION: linker-adapter

<400> SEQUENCE: 29
aattctcaat gcagggc                                                17

<210> SEQ ID NO 30
<211> LENGTH: 17
<212> TYPE: DNA
<213> ORGANISM: Artificial
<220> FEATURE:
<223> OTHER INFORMATION: linker-adapter

<400> SEQUENCE: 30
gagttacgtc ccgaatt                                                17

<210> SEQ ID NO 31
<211> LENGTH: 25
<212> TYPE: DNA
<213> ORGANISM: Artificial
<220> FEATURE:
<223> OTHER INFORMATION: VH forward primer

<400> SEQUENCE: 31
gactcgagcc caagtcttag acatc                                       25

<210> SEQ ID NO 32
<211> LENGTH: 33
<212> TYPE: DNA

```
<213> ORGANISM: Artificial
<220> FEATURE:
<223> OTHER INFORMATION: VH reverse primer

<400> SEQUENCE: 32
caagcttacc tgaggagacg gtgactgacg ttc                          33

<210> SEQ ID NO 33
<211> LENGTH: 27
<212> TYPE: DNA
<213> ORGANISM: Artificial
<220> FEATURE:
<223> OTHER INFORMATION: VK forward primer

<400> SEQUENCE: 33
gatctagaca agatggattt tcaagtg                                 27

<210> SEQ ID NO 34
<211> LENGTH: 29
<212> TYPE: DNA
<213> ORGANISM: Artificial
<220> FEATURE:
<223> OTHER INFORMATION: VK reverse primer

<400> SEQUENCE: 34
gaagatctta cgttttattt ccagcttgg                               29

<210> SEQ ID NO 35
<211> LENGTH: 117
<212> TYPE: PRT
<213> ORGANISM: Artificial
<220> FEATURE:
<223> OTHER INFORMATION: VH369 heavy chain

<400> SEQUENCE: 35

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Gln Gln Pro Gln Asn Met Arg Thr Met Ala Thr Tyr Phe
                85                  90                  95

Cys Val Arg Phe Ile Ser Lys Gly Asp Tyr Trp Gly Gln Gly Thr Ser
            100                 105                 110

Val Thr Val Ser Ser
        115

<210> SEQ ID NO 36
<211> LENGTH: 19
<212> TYPE: PRT
<213> ORGANISM: Artificial
<220> FEATURE:
<223> OTHER INFORMATION: VH2.1 partial  sequence

<400> SEQUENCE: 36

Ala Thr Tyr Phe Cys Val Arg Phe Ile Ile Ser Lys Gly Asp Tyr Trp
1               5                   10                  15
```

<210> SEQ ID NO 37
<211> LENGTH: 19
<212> TYPE: PRT
<213> ORGANISM: Artificial
<220> FEATURE:
<223> OTHER INFORMATION: VH2.2 partial sequence

<400> SEQUENCE: 37

Ala Thr Tyr Phe Cys Val Arg Phe Ile Val Ser Lys Gly Asp Tyr Trp
1               5                   10                  15

Gly Gln Gly

<210> SEQ ID NO 38
<211> LENGTH: 19
<212> TYPE: PRT
<213> ORGANISM: Artificial
<220> FEATURE:
<223> OTHER INFORMATION: VH2.3 partial sequence

<400> SEQUENCE: 38

Ala Thr Tyr Phe Cys Val Arg Phe Ile Ser Ala Lys Gly Asp Tyr Trp
1               5                   10                  15

Gly Gln Gly

<210> SEQ ID NO 39
<211> LENGTH: 19
<212> TYPE: PRT
<213> ORGANISM: Artificial
<220> FEATURE:
<223> OTHER INFORMATION: VH2.4 partial sequence

<400> SEQUENCE: 39

Ala Thr Tyr Phe Cys Val Arg Phe Ile Ser Lys Thr Gly Asp Tyr Trp
1               5                   10                  15

Gly Gln Gly

<210> SEQ ID NO 40
<211> LENGTH: 10494
<212> TYPE: DNA
<213> ORGANISM: Artificial
<220> FEATURE:
<223> OTHER INFORMATION: pdHL7s-VK8/VH7-IL2  sequence

<400> SEQUENCE: 40
gtcgacattg attattgact agttattaat agtaatcaat tacggggtca ttagttcata      60
gtcgacattg attattgact agttattaat agtaatcaat tacggggtca ttagttcata     120
gcccatatat ggagttccgc gttacataac ttacggtaaa tggcccgcct ggctgaccgc     180
ccaacgaccc ccgcccattg acgtcaataa tgacgtatgt tcccatagta acgccaatag     240
ggactttcca ttgacgtcaa tgggtggagt atttacggta aactgcccac ttggcagtac     300
atcaagtgta tcatatgcca agtacgcccc ctattgacgt caatgacggt aaatggcccg     360
cctggcatta tgcccagtac atgaccttat gggactttcc tacttggcag tacatctacg     420
tattagtcat cgctattacc atggtgatgc ggttttggca gtacatcaat gggcgtggat     480
agcggtttga ctcacgggga tttccaagtc tccaccccat tgacgtcaat gggagtttgt     540
tttggcacca aaatcaacgg gactttccaa aatgtcgtaa caactccgcc ccattgacgc     600
aaatgggcgg taggcgtgta cggtgggagg tctatataag cagagctctc tggctaacta     660

```
cagaacccac tgcttactgg cttatcgaaa ttaatacgac tcactatagg gagaccctct    720
agaatgaagt tgcctgttag gctgttggtg ctgatgttct ggattcctgg tgaggagaga    780
gggaagtgag ggaggagaat ggacagggag caggagcact gaatcccatt gctcattcca    840
tgtatctggc atgggtgaga agatgggtct tatcctccag catggggcct ctgggtgaa     900 tacttgttag agggaggttc cagatgggaa catgtgctat aatgaagatt atgaaatgga    960
tgcctgggat ggtctaagta atgccttaga agtgactaga cacttgcaat tcactttttt   1020
tggtaagaag agattttag gctataaaaa aatgttatgt aaaaataaac gatcacagtt    1080
gaaataaaaa aaaatataa ggatgttcat gaattttgtg tataactatg tatttctctc    1140
tcattgtttc agcttcctta agcgagatcg tgctgaccca gtccccgcc accctgtccc    1200 tgtccccgg cgagcgcgtg accctgacct gctccgcctc ctcctccgtg tcctacatgc     1260
tgtggtacca gcagaagcca ggatcctcgc ccaaaccctg attttttgac acatccaacc    1320
tggcttctgg attccctgct cgcttcagtg gcagtgggtc tgggacctct tactctctca    1380
taatcagcag catggaggct gaagatgctg ccacttatta ctgccatcag cggagtggtt    1440
acccgtacac gttcggaggg gggaccaagc tggaaataaa acgtaagatc cgcaattct     1500 aaactctgag ggggtcggat gacgtggcca ttctttgcct aaagcattga gtttactgca    1560
aggtcagaaa agcatgcaaa gccctcagaa tggctgcaaa gagctccaac aaaacaattt    1620
agaactttat taaggaatag ggggaagcta ggaagaaact caaaacatca gatttttaaa    1680
tacgcttctt ggtctccttg ctataattat ctgggataag catgctgttt tctgtctgtc    1740
cctaacatgc cctgtgatta tccgcaaaca acacacccaa gggcagaact ttgttactta    1800
aacaccatcc tgtttgcttc tttcctcagg aactgtggct gcaccatctg tcttcatctt    1860
cccgccatct gatgagcagt tgaaatctgg aactgcctct gttgtgtgcc tgctgaataa    1920
cttctatccc agagaggcca aagtacagtg gaaggtggat aacgccctcc aatcgggtaa    1980
ctcccaggag agtgtcacag agcaggacag caaggacagc acctacagcc tcagcagcac    2040
cctgacgctg agcaaagcag actacgagaa acacaaagtc tacgcctgcg aagtcaccca    2100
tcagggcctg agctcgcccg tcacaaagag cttcaacagg ggagagtgtt agagggagaa    2160
gtgcccccac ctgctcctca gttccagcct gaccccctcc catcctttgg cctctgaccc    2220 ttttccaca ggggacctac ccctattgcg gtcctccagc tcatctttca cctcaccccc     2280
ctcctcctcc ttggctttaa ttatgctaat gttggaggag aatgaataaa taaagtgaat    2340
ctttgcacct gtggtttctc tctttcctca atttaataat tattatctgt tgtttaccaa    2400
ctactcaatt tctcttataa gggactaaat atgtagtcat cctaaggcgc ataaccattt    2460
ataaaaatca tccttcattc tattttaccc tatcatcctc tgcaagacag tcctccctca    2520
aacccacaag ccttctgtcc tcacagtccc ctgggccatg gtaggagaga cttgcttcct    2580
tgttttcccc tcctcagcaa gccctcatag tccttttaa gggtgacagg tcttacggtc     2640
atatatcctt tgattcaatt ccctgggaat caaccaaggc aaattttca aaagaagaaa     2700 cctgctataa agagaatcat tcattgcaac atgatataaa ataacaacac aataaaagca    2760
attaaataaa caaacaatag ggaaatgttt aagttcatca tggtacttag acttaatgga    2820
atgtcatgcc ttatttacat ttttaaacag gtactgaggg actcctgtct gccaagggcc    2880
gtattgagta ctttccacaa cctaatttaa tccacactat actgtgagat taaaaacatt    2940
cattaaaatg ttgcaaaggt tctataaagc tgagagacaa atatattcta taactcagca    3000
atcccacttc tagggtcgac gttgacattg attattgact agttattaat agtaatcaat    3060
```

-continued

```
tacggggtca ttagttcata gcccatatat ggagttccgc gttacataac ttacggtaaa    3120
tggcccgcct ggctgaccgc ccaacgaccc ccgcccattg acgtcaataa tgacgtatgt    3180
tcccatagta acgccaatag ggactttcca ttgacgtcaa tgggtggagt atttacggta    3240
aactgcccac ttggcagtac atcaagtgta tcatatgcca agtacgcccc ctattgacgt    3300
caatgacggt aaatggcccg cctggcatta tgcccagtac atgaccttat ggactttcc    3360 tacttggcag tacatctacg tattagtcat cgctattacc atggtgatgc ggttttggca    3420
gtacatcaat gggcgtggat agcggtttga ctcacgggga tttccaagtc tccacccat    3480 tgacgtcaat gggagtttgt tttggcacca aaatcaacgg gactttccaa aatgtcgtaa    3540
caactccgcc ccattgacgc aaatgggcgg taggcgtgta cggtgggagg tctatataag    3600
cagagctctc tggctaacta cagaacccac tgcttactgg cttatcgaaa ttaatacgac    3660
tcactatagg gagacccaag ctcctcgagg ctagaatgaa gttgcctgtt aggctgttgg    3720
tgctgatgtt ctggattcct ggtgaggaga gagggaagtg agggaggaga atggacaggg    3780
agcaggagca ctgaatccca ttgctcattc catgtatctg gcatgggtga aagatgggt    3840 cttatcctcc agcatggggc ctctggggtg aatacttgtt agagggaggt tccagatggg    3900
aacatgtgct ataatgaaga ttatgaaatg gatgcctggg atggtctaag taatgcctta    3960
gaagtgacta gacacttgca attcactttt tttggtaaga agagattttt aggctataaa    4020
aaaatgttat gtaaaaataa acgatcacag ttgaaataaa aaaaaatat aaggatgttc    4080 atgaattttg tgtataacta tgtatttctc tctcattgtt tcagcttcct taagccagat    4140
ccagttggtg cagtctggag ctgaggtgaa gaagcctgga gagacagtca agatctcctg    4200
caaggcttct gggtatacct tcacaaacta tggaatgaac tgggtgaagc agactccagg    4260
aaagggttta agtggatgg gctggataaa cacctacact ggagaaccaa catatgctga    4320
tgacttcaag gacgggttg ccttctcttt ggaaacctct accagcactg ccttttttgca    4380 gatcaacaat ctcagaagtg aggacacggc tacatatttc tgtgtaagat ttatttctaa    4440
gggggactac tggggtcaag gaacgtcagt caccgtctcc tcaggtaagc tttctggggc    4500
aggccaggcc tgaccttggc tttggggcag ggaggggct aaggtgaggc aggtggcgcc    4560
agccaggtgc acacccaatg cccatgagcc cagacactgg acgctgaacc tcgcggacag    4620
ttaagaaccc aggggcctct gcgccctggg cccagctctg tcccacaccg cggtcacatg    4680
gcaccacctc tcttgcagcc tccaccaagg gcccatcggt cttccccctg gcaccctcct    4740
ccaagagcac ctctgggggc acagcggccc tgggctgcct ggtcaaggac tacttccccg    4800
aaccggtgac ggtgtcgtgg aactcaggcg ccctgaccag cggcgtgcac accttcccgg    4860
ctgtcctaca gtcctcagga ctctactccc tcagcagcgt ggtgaccgtg ccctccagca    4920
gcttgggcac ccagacctac atctgcaacg tgaatcacaa gcccagcaac caaggtgg    4980 acaagagagt tggtgagagg ccagcacagg gagggagggt gtctgctgga agccaggctc    5040
agcgctcctg cctggacgca tcccggctat gcagtcccag tccagggcag caaggcaggc    5100
cccgtctgcc tcttcacccg gaggcctctg cccgccccac tcatgctcag ggagagggtc    5160
ttctggcttt ttccccaggc tctgggcagg cacaggctag gtgcccctaa cccaggccct    5220
gcacacaaag gggcaggtgc tgggctcaga cctgccaaga gccatatccg gaggaccct    5280 gccctgacc taagcccacc ccaaaggcca aactctccac tccctcagct cggacacctt    5340
ctctcctccc agattccagt aactcccaat cttctctctg cagagcccaa atcttgtgac    5400
```

```
aaaactcaca catgcccacc gtgcccaggt aagccagccc aggcctcgcc ctccagctca   5460
aggcgggaca ggtgccctag agtagcctgc atccagggac aggccccagc cgggtgctga   5520
cacgtccacc tccatctctt cctcagcacc tgaactcctg gggggaccgt cagtcttcct   5580 cttccccca aaacccaagg acaccctcat gatctcccgg acccctgagg tcacatgcgt   5640
ggtggtggac gtgagccacg aagaccctga ggtcaagttc aactggtacg tggacggcgt   5700
ggaggtgcat aatgccaaga caaagccgcg ggaggagcag tacaacagca cgtaccgtgt   5760
ggtcagcgtc ctcaccgtcc tgcaccagga ctggctgaat ggcaaggagt acaagtgcaa   5820
ggtctccaac aaagccctcc cagccccat cgagaaaacc atctccaaag ccaaaggtgg   5880
gacccgtggg gtgcgagggc cacatggaca gaggccggct cggcccaccc tctgccctga   5940
gagtgaccgc tgtaccaacc tctgtcccta caggcagcc ccgagaacca caggtgtaca   6000
ccctgccccc atcacgggag gagatgacca gaaccaggt cagcctgacc tgcctggtca   6060
aaggcttcta tcccagcgac atcgccgtgg agtgggagag caatgggcag ccggagaaca   6120
actacaagac cacgcctccc gtgctggact ccgacggctc cttcttcctc tatagcaagc   6180
tcaccgtgga caagagcagg tggcagcagg ggaacgtctt ctcatgctcc gtgatgcatg   6240
aggctctgca caaccactac acgcagaaga gcctctccct gtccccgggt aaagcccaa   6300 cttcaagttc tacaaagaaa acacagctgc aactggagca tctcctgctg gatctccaga   6360
tgattctgaa tggaattaac aactacaaga atcccaaact caccaggatg ctcacattca   6420
agttctacat gcccaagaag gccacagagc tcaaacatct ccagtgtcta gaggaggaac   6480
tcaaacctct ggaggaagtg ctaaacctcg ctcagagcaa aaacttccac ttaagaccta   6540
gggacttaat cagcaatatc aacgtaatag ttctggaact aaagggatcc gaaacaacat   6600
tcatgtgtga atatgctgat gagacagcaa ccattgtaga attcctaaac agatggatta   6660 cctttttgtca aagcatcatc tcaacactaa cttgataatt aagtgctcga gggatccaga   6720
catgataaga tacattgatg agtttggaca aaccacaact agaatgcagt gaaaaaatg   6780 cttatttgt gaaatttgtg atgctattgc tttatttgta accattagaa gctgcaataa   6840
acaagttaac aacaacaatt gcattcattt tatgtttcag gttcaggggg aggtgtggga   6900
ggttttttaa agcaagtaaa acctctacaa atgtggtatg gctgattatg atcctgcctc   6960
gcgcgtttcg gtgatgacgg tgaaaacctc tgacacatgc agctcccgga gacggtcaca   7020
gcttgtctgt aagcggatgc cgggagcaga caagcccgtc agggcgcgtc agcgggtgtt   7080
ggcgggtgtc ggggcgcagc catgacccag tcacgtagcg atagcggagt gtatactggc   7140
ttaactatgc ggcatcagag cagattgtac tgagagtgca ccatatgcgg tgtgaaatac   7200
cgcacagatg cgtaaggaga aaataccgca tcaggcgctc ttccgcttcc tcgctcactg   7260
actcgctgcg ctcggtcgtt cggctgcggc gagcggtatc agctcactca aaggcggtaa   7320
tacggttatc cacagaatca ggggataacg caggaaagaa catgtgagca aaaggccagc   7380
aaaaggccag gaaccgtaaa aaggccgcgt tgctggcgtt tttccatagg ctccgccccc   7440
ctgacgagca tcacaaaaat cgacgctcaa gtcagaggtg cgaaacccg acaggactat   7500 aaagatacca ggcgtttccc cctggaagct ccctcgtgcg ctctcctgtt ccgaccctgc   7560
cgcttaccgg atacctgtcc gcctttctcc cttcgggaag cgtggcgctt tctcaatgct   7620
cacgctgtag gtatctcagt tcggtgtagg tcgttcgctc caagctgggc tgtgtgcacg   7680 aacccccgt tcagcccgac cgctgcgcct tatccggtaa ctatcgtctt gagtccaacc   7740
cggtaagaca cgacttatcg ccactggcag cagccactgg taacaggatt agcagagcga   7800
```

```
ggtatgtagg cggtgctaca gagttcttga agtggtggcc taactacggc tacactagaa   7860
ggacagtatt tggtatctgc gctctgctga agccagttac cttcggaaaa agagttggta   7920
gctcttgatc cggcaaacaa accaccgctg gtagcggtgg ttttttttgtt tgcaagcagc   7980
agattacgcg cagaaaaaaa ggatctcaag aagatccttt gatcttttct acggggtctg   8040
acgctcagtg gaacgaaaac tcacgttaag ggattttggt catgagatta tcaaaaagga   8100
tcttcaccta gatcctttta aattaaaaat gaagttttaa atcaatctaa agtatatatg   8160
agtaaacttg gtctgacagt taccaatgct taatcagtga ggcacctatc tcagcgatct   8220
gtctatttcg ttcatccata gttgcctgac tccccgtcgt gtagataact acgatacggg   8280
agggcttacc atctggcccc agtgctgcaa tgataccgcg agacccacgc tcaccggctc   8340
cagatttatc agcaataaac cagccagccg aagggccga gcgcagaagt ggtcctgcaa   8400
ctttatccgc ctccatccag tctattaatt gttgccggga agctagagta agtagttcgc   8460
cagttaatag tttgcgcaac gttgttgcca ttgctgcagg catcgtggtg tcacgctcgt   8520
cgtttggtat ggcttcattc agctccggtt cccaacgatc aaggcgagtt acatgatccc   8580
ccatgttgtg caaaaaagcg gttagctcct tcggtcctcc gatcgttgtc agaagtaagt   8640
tggccgcagt gttatcactc atggttatgg cagcactgca taattctctt actgtcatgc   8700
catccgtaag atgcttttct gtgactggtg agtactcaac caagtcattc tgagaatagt   8760
gtatgcggcg accgagttgc tcttgcccgg cgtcaacacg gataataccg cgccacata   8820
gcagaacttt aaaagtgctc atcattggaa aacgttcttc ggggcgaaaa ctctcaagga   8880
tcttaccgct gttgagatcc agttcgatgt aacccactcg tgcacccaac tgatcttcag   8940
catcttttac tttcaccagc gtttctgggt gagcaaaaac aggaaggcaa aatgccgcaa   9000
aaaagggaat aagggcgaca cggaaatgtt gaatactcat actcttcctt tttcaatatt   9060
attgaagcat ttatcagggt tattgtctca tgagcggata catatttgaa tgtatttaga   9120
aaaataaaca ataggggtt ccgcgcacat ttccccgaaa agtgccacct gacgtctaag   9180
aaaccattat tatcatgaca ttaacctata aaaataggcg tatcacgagg ccctttcgtc   9240
ttcaagaatt ccgatccaga catgataaga tacattgatg agtttggaca aaccacaact   9300
agaatgcagt gaaaaaaatg ctttatttgt gaaatttgtg atgctattgc tttatttgta   9360
accattagaa gctgcaataa acaagttaac aacaacaatt gcattcattt tatgtttcag   9420
gttcaggggg aggtgtggga ggttttttaa agcaagtaaa acctctacaa atgtggtatg   9480
gctgattatg atctaaagcc agcaaaagtc ccatggtctt ataaaaatgc atagctttcg   9540
gagggagca gagaacttga aagcatcttc ctgttagtct ttcttctcgt agaccttaaa   9600
ttcatacttg attcctttt cctcctggac ctcagagagg acgcctgggt attctgggag   9660
aagtttatat ttccccaaat caatttctgg gaaaaacgtg tcacttttcaa attcctgcat   9720
gatccttgtc acaaagagtc tgaggtggcc tggttgattc atggcttcct ggtaaacaga   9780
actgcctccg actatccaaa ccatgtctac tttacttgcc aattccggtt gttcaataag   9840
tcttaaggca tcatccaaac ttttggcaag aaaatgagct cctcgtggtg gttctttgag   9900
ttctctactg agaactatat taattctgtc ctttaaaggt cgattcttct caggaatgga   9960
gaaccaggtt ttcctaccca taatcaccag attctgttta ccttccactg aagaggttgt  10020
ggtcattctt tggaagtact tgaactcgtt cctgagcgga ggccagggtc ggtctccgtt  10080
cttgccaatc cccatatttt gggacacggc gacgatgcag ttcaatggtc gaaccatgag  10140
```

-continued

```
ggcaccaagc tagctttttg caaaagccta ggcctccaaa aaagcctcct cactacttct    10200
ggaatagctc agaggccgag gcggcctcgg cctctgcata aataaaaaaa attagtcagc    10260
catggggcgg agaatgggcg gaactgggcg gagttagggg cgggatgggc ggagttaggg    10320
gcgggactat ggttgctgac taattgagat gcatgctttg catacttctg cctgctgggg    10380
agcctgggga ctttccacac ctggttgctg actaattgag atgcatgctt tgcatacttc    10440
tgcctgctgg ggagcctggg gactttccac accctaactg acacacattc caca          10494
```

<210> SEQ ID NO 41
<211> LENGTH: 579
<212> TYPE: PRT
<213> ORGANISM: Artificial
<220> FEATURE:
<223> OTHER INFORMATION: heavy chain-IL2

<400> SEQUENCE: 41

```
Gln Ile Gln Leu Val Gln Ser Gly Ala Glu Val Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Thr Ser Thr Ala Phe
65                  70                  75                  80

Leu Gln Ile Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Ala Pro
        435                 440                 445

Thr Ser Ser Thr Lys Lys Thr Gln Leu Gln Leu Glu His Leu Leu Leu
    450                 455                 460

Leu Asp Leu Gln Met Ile Leu Asn Gly Ile Asn Asn Tyr Lys Asn Pro
465                 470                 475                 480

Lys Leu Thr Arg Met Leu Thr Phe Lys Phe Tyr Met Pro Lys Lys Ala
                485                 490                 495

Thr Glu Leu Lys His Leu Gln Cys Leu Glu Glu Glu Leu Lys Pro Leu
            500                 505                 510

Glu Glu Val Leu Asn Leu Ala Gln Ser Lys Asn Phe His Leu Arg Pro
        515                 520                 525

Arg Asp Leu Ile Ser Asn Ile Asn Val Ile Val Leu Glu Leu Lys Gly
    530                 535                 540

Ser Glu Thr Thr Phe Met Cys Glu Tyr Ala Asp Glu Thr Ala Thr Ile
545                 550                 555                 560

Val Glu Phe Leu Asn Arg Trp Ile Thr Phe Cys Gln Ser Ile Ile Ser
                565                 570                 575

Thr Leu Thr

<210> SEQ ID NO 42
<211> LENGTH: 213
<212> TYPE: PRT
<213> ORGANISM: Artificial
<220> FEATURE:
<223> OTHER INFORMATION: light chain

<400> SEQUENCE: 42

Glu Ile Val Leu Thr Gln Ser Pro Ala Thr Leu Ser Leu Ser Pro Gly
1               5                   10                  15

Glu Arg Val Thr Leu Thr Cys Ser Ala Ser Ser Ser Val Ser Tyr Met
            20                  25                  30

Leu Trp Tyr Gln Gln Lys Pro Gly Ser Ser Pro Lys Pro Trp Ile Phe
        35                  40                  45

Asp Thr Ser Asn Leu Ala Ser Gly Phe Pro Ala Arg Phe Ser Gly Ser
    50                  55                  60

Gly Ser Gly Thr Ser Tyr Ser Leu Ile Ile Ser Ser Met Glu Ala Glu
65                  70                  75                  80

Asp Ala Ala Thr Tyr Tyr Cys His Gln Arg Ser Gly Tyr Pro Tyr Thr
```

-continued

```
                85                  90                  95
Phe Gly Gly Thr Lys Leu Glu Ile Lys Arg Thr Val Ala Ala Pro
            100                 105                 110

Ser Val Phe Ile Phe Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210
```